(12) United States Patent
Guilford et al.

(10) Patent No.: US 6,350,761 B1
(45) Date of Patent: Feb. 26, 2002

(54) BENZENAMINE DERIVATIVES AS ANTI-COAGULANTS

(75) Inventors: William J. Guilford, Belmont; Steven T. Sakata, San Diego; Kenneth J. Shaw, San Rafael, all of CA (US); Shung Wu, Princeton, NJ (US); Wei Xu, Danville; Zuchun Zhao, Richmond, both of CA (US)

(73) Assignee: Berlex Laboratories, Inc., Richmond, CA (US)

( * ) Notice: Subject to any disclaimer, the term of this patent is extended or adjusted under 35 U.S.C. 154(b) by 0 days.

(21) Appl. No.: 09/624,519

(22) Filed: Jul. 24, 2000

Related U.S. Application Data

(60) Provisional application No. 60/146,572, filed on Jul. 30, 1999.

(51) Int. Cl.[7] ............... A61K 31/445; A61K 31/30; C07D 211/40; C07D 211/56; C07D 315/00
(52) U.S. Cl. .............. 514/327; 514/329; 514/424; 514/426; 514/432; 514/448; 546/216; 546/223; 548/530; 548/544; 548/559; 549/28; 549/65; 549/68; 549/69; 549/416; 549/419; 549/475; 549/480
(58) Field of Search ................... 549/426, 424, 549/427, 416, 419, 475, 480, 28, 65, 68, 69; 546/216, 223; 548/530, 544, 559; 514/327, 329, 424, 426, 432, 448

(56) References Cited

U.S. PATENT DOCUMENTS

| | | |
|---|---|---|
| 4,064,169 A | 12/1977 | Hamano et al. |
| 4,514,406 A * | 4/1985 | Ohsami et al. ............. 549/426 |
| 4,594,092 A * | 6/1986 | Speltz et al. ................. 549/426 |
| 5,332,822 A | 7/1994 | Misra |
| 5,451,700 A | 9/1995 | Morrissey et al. |
| 5,612,363 A | 3/1997 | Mohan et al. |
| 5,633,381 A | 5/1997 | Dallas et al. |
| 5,691,364 A | 11/1997 | Buckman et al. |
| 5,693,641 A | 12/1997 | Buckman et al. |
| 5,721,214 A | 2/1998 | Marlowe et al. |
| 5,726,173 A | 3/1998 | Mohan et al. |
| 5,726,198 A | 3/1998 | Mohan et al. |
| 5,728,697 A | 3/1998 | Mohan et al. |
| 5,731,308 A | 3/1998 | Mohan et al. |
| 5,731,311 A | 3/1998 | Mohan et al. |
| 5,753,635 A | 5/1998 | Buckman et al. |
| 5,846,970 A | 12/1998 | Buckman et al. |
| 5,846,972 A | 12/1998 | Buckman et al. |
| 5,849,759 A | 12/1998 | Arnaiz et al. |
| 5,859,005 A | 1/1999 | Mohan et al. |
| 5,863,914 A | 1/1999 | Mohan et al. |
| 5,869,501 A | 2/1999 | Hirayama et al. |
| 5,877,181 A | 3/1999 | Buckman et al. |
| 5,883,100 A | 3/1999 | Buckman et al. |
| 5,889,005 A | 3/1999 | Buckman et al. |
| 5,994,375 A | 11/1999 | Kochanny et al. |
| 6,004,981 A | 12/1999 | Buckman et al. |
| 6,004,985 A | 12/1999 | Kochanny et al. |
| 6,008,234 A | 12/1999 | Kochanny et al. |
| 6,034,103 A | 3/2000 | Buckman et al. |
| 6,071,912 A | 6/2000 | Kochanny et al. |
| 6,127,376 A | 10/2000 | Davey et al. |
| 6,140,351 A | 10/2000 | Arnaiz et al. |
| 6,166,088 A | 12/2000 | Kochanny et al. |

FOREIGN PATENT DOCUMENTS

| | | |
|---|---|---|
| EP | 0449195 A2 | 3/1991 |
| EP | 0518818 A2 | 6/1992 |
| EP | 0540051 A1 | 10/1992 |
| EP | 0567966 A1 | 4/1993 |
| EP | 0601459 A2 | 12/1993 |
| GB | 824908 | 12/1959 |
| WO | WO93/15756 | 8/1993 |
| WO | WO94/02470 | 2/1994 |
| WO | WO94/13693 | 6/1994 |
| WO | WO94/17817 | 8/1994 |
| WO | WO96/10022 | 4/1996 |
| WO | WO99/00127 | 1/1999 |
| WO | WO99/00128 | 1/1999 |
| WO | WO99/37643 | 7/1999 |
| WO | WO99/52895 | 10/1999 |

OTHER PUBLICATIONS

Tidwell, R. et al., "Strategies for Anticoagulation with Synthetic Protease Inhibitors, Xa Inhibitors Versus Thrombin Inhibitors," *Thrombosis Research*, (1980) 19:339–349.

Wagner, G. et al., "Synthese von a–a'–Bis[amidinobenzyliden]–und a–a' Bis–[amidinobenzyl]–cycloalkanonen," *Pharmazie*, (1977) 32,141–145.

Stüzebecher, J. et al., "Cyclic Amides of Nα–arysulfonylaminoacylated 4–amidinophenylalanine—Tight Binding Inhibitors of Thrombin," *Thrombosis Research*, (1983) 29:635–642.

Kikumoto, R. et al., "Selective inhibition of Thrombin by (2R,4R)–4–Methyl–1–[N²–[(3–methyl–1,2,3,4–tetrahydro–8–quinolinyl)–sulfonyl]–L–arginyl)]–2piperidinecarboxylic Acid," *Biochemistry*, (1984) 23:85–90.

Stürzebecher, J. et al., "Synthetic Inhibitors of Serine Proteinases XXIII, Inhibition of Factor Xa by Diamidines", *Thrombosis Research*, (1980) 17:545–548.

(List continued on next page.)

*Primary Examiner*—D. Margaret Seaman
*Assistant Examiner*—Raymond Covington
(74) *Attorney, Agent, or Firm*—Carol J. Roth

(57) ABSTRACT

This invention is directed to benzenamine derivatives of formula (I):

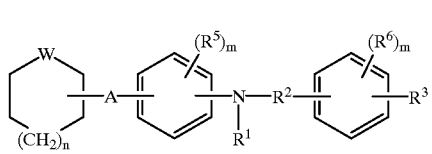

wherein A, W, m, n, $R^1$, $R^2$, $R^3$, $R^4$, $R^5$ and $R^6$ are defined herein. These compounds are useful as anti-coagulants.

15 Claims, No Drawings

OTHER PUBLICATIONS

Chauhan, P. et al., "Effect a new diamidines against *Leishmania donovani* infection," *Indian Journal of Experimental Biology*, (1993) 31:196–198.

Ashley, J. et al., "The Search for Chemotherapeutic Amidines. Part XVI. Amidinoanilino–1,3,5–triazines and Related Compounds", *J. of the Chemical Society*, (1960) 4525:4532.

Geratz, J. et al., "The Inhibition of Urokinase by Aromatic Diamidines" *Thrombos. Diathes haemorrh.* (Stuttg.), (1975)33:230–243.

Geratz, J. et al. "Novel Bis (benzamidino) Compounds with an Aromatic Central Link. Inhibitors of Thrombin, Pancreatic Kallikrein, Trypsin, and Complement" *J. of Medicinal Chemistry*, (1976) 19(5):634–639.

Chauhan, P. et al., "Antiparasitic Agents: Part VI—Synthesis of 1,2–,1,3–&1,4–Bis(4–substituted aryloxy)benzenes & Their Biological Activities",*Indian Journal of Chemistry*, (1988) 27B:38–42.

Delia, T. et al., "Ring–Based Analogues of Pentamidine Versus *P. Carinii* Pneumonia In Culture", *Bioorganic & Medicinal Chemistry Letters*, (1996) 6(19):2267–2370.

U.S. Patent Application Serial No. 09/196,921, filed Nov. 19, 1998, entitled: *Polyhydroxylated Monocyclic N–Heterocyclic Derivatives as Anti–Coagulants.*

* cited by examiner

BENZENAMINE DERIVATIVES AS ANTI-COAGULANTS

This application claims the benefit of U.S. Provisional Application No. 60/146,572, filed Jul. 30, 1999, which is incorporated herein in full by reference.

FIELD OF THE INVENTION

The present invention is directed to benzenamine derivatives and their pharmaceutically acceptable salts, which inhibit the enzyme, factor Xa, thereby being useful as anti-coagulants. It also relates to pharmaceutical compositions containing the derivatives or their pharmaceutically acceptable salts, and methods of their use.

BACKGROUND OF THE INVENTION

Factor Xa is a member of the trypsin-like serine protease class of enzymes. A one-to-one binding of factors Xa and Va with calcium ions and phospholipid forms the prothrombinase complex which converts prothrombin to thrombin. Thrombin, in turn, converts fibrinogen to fibrin which polymerizes to form insoluble fibrin.

In the coagulation cascade, the prothrombinase complex is the convergent point of the intrinsic (surface activated) and extrinsic (vessel injury-tissue factor) pathways (*Biochemistry* (1991), Vol. 30, p. 10363; and *Cell* (1988), Vol. 53, pp. 505–518). The model of the coagulation cascade has been refined further with the discovery of the mode of action of tissue factor pathway inhibitor (TFPI) (*Seminars in Hematology* (1992), Vol. 29, pp. 159–161). TFPI is a circulating multi-domain serine protease inhibitor with three Kunitz-type domains which competes with factor Va for free factor Xa. Once formed, the binary complex of factor Xa and TFPI becomes a potent inhibitor of the factor VIIa and tissue factor complex.

Factor Xa can be activated by two distinct complexes, by tissue factor-VIIa complex on the "Xa burst" pathway and by the factor IXa-VIIIa complex (TENase) of the "sustained Xa" pathway in the coagulation cascade. After vessel injury, the "Xa burst" pathway is activated via tissue factor (TF). Up regulation of the coagulation cascade occurs via increased factor Xa production via the "sustained Xa" pathway. Down regulation of the coagulation cascade occurs with the formation of the factor Xa-TFPI complex, which not only removes factor Xa but also inhibits further factor formation via the "Xa burst" pathway. Therefore, the coagulation cascade is naturally regulated by factor Xa.

The primary advantage of inhibiting factor Xa over thrombin in order to prevent coagulation is the focal role of factor Xa versus the multiple functions of thrombin. Thrombin not only catalyzes the conversion of fibrinogen to fibrin, factor VIII to VIIIA, factor V to Va, and factor XI to XIa, but also activates platelets, is a monocyte chemotactic factor, and mitogen for lymphocytes and smooth muscle cells. Thrombin activates protein C, the in vivo anti-coagulant inactivator of factors Va and VIIIa, when bound to thrombomodulin. In circulation, thrombin is rapidly inactivated by antithrombin III (ATIII) and heparin cofactor II (HCII) in a reaction which is catalyzed by heparin or other proteoglycan-associated glycosaminoglycans, whereas thrombin in tissues is inactivated by the protease, nexin. Thrombin carries out its multiple cellular activation functions through a unique "tethered ligand" thrombin receptor (*Cell* (1991), Vol. 64, p. 1057), which requires the same anionic binding site and active site used in fibrinogen binding and cleavage and by thrombomodulin binding and protein C activation. Thus, a diverse group of in vivo molecular targets compete to bind thrombin and the subsequent proteolytic events will have very different physiological consequences depending upon which cell type and which receptor, modulator, substrate or inhibitor binds thrombin.

Published data with the proteins antistasin and tick anti-coagulant peptide (TAP) demonstrate that factor Xa inhibitors are efficacious anti-coagulants (*Thrombosis and Haemostasis* (1992), Vol. 67, pp. 371–376; and *Science* (1990), Vol. 248, pp. 593–596).

The active site of factor Xa can be blocked by either a mechanism-based or a tight binding inhibitor (a tight binding inhibitor differs from a mechanism-based inhibitor by the lack of a covalent link between the enzyme and the inhibitor). Two types of mechanism-based inhibitors are known, reversible and irreversible, which are distinguished by ease of hydrolysis of the enzyme-inhibitor link (*Thrombosis Res.* (1992), Vol. 67, pp. 221–231; and *Trends Pharmacol. Sci.* (1987), Vol. 8, pp. 303–307). A series of guanidino compounds are examples of tight-binding inhibitors (*Thrombosis Res.* (1980), Vol.19, pp. 339–349). Arylsulfonyl-arginine-piperidine-carboxylic acid derivatives have also been shown to be tight-binding inhibitors of thrombin (*Biochem.* (1984), Vol. 23, pp. 85–90), as well as a series of arylamidine-containing compounds, including 3-amidinophenylaryl derivatives (*Thrombosis Res.* (1983), Vol. 29, pp. 635–642) and bis(amidino)benzyl cycloketones (*Thrombosis Res.* (1980), Vol. 17, pp. 545–548). However, these compounds demonstrate poor selectivity for factor Xa.

RELATED DISCLOSURES

European Published Patent Application 0 540 051 (Nagahara et al.) describes aromatic amidine derivatives. These derivatives are stated to be capable of showing a strong anticoagulant effect through reversible inhibition of factor Xa.

The synthesis of α,α'-bis(amidinobenzylidene)cycloalkanones and α,α'-bis(amidinobenzyl)cycloalkanones is described in *Pharmazie* (1977), Vol. 32, No. 3, pp. 141–145. These compounds are disclosed as being serine protease inhibitors.

U.S. Pat. No. 5,451,700 (Morrissey et al.) describes amidino compounds. These compounds are stated to be useful as selective $LTB_4$ receptor antagonists.

U.S. Pat. No. 5,612,363 (Mohan et al.) describes N,N-di(aryl) cyclic urea derivatives. These compounds are stated to be factor Xa inhibitors, thereby being useful as anticoagulants.

U.S. Pat. No. 5,633,381 (Dallas et al.) describes (Z,Z), (Z,E) and (E,Z) isomers of substituted bis(phenylmethylene) cycloketones. These compounds are disclosed as being factor Xa inhibitors, thereby being useful as anticoagulants.

PCT Published Patent Application WO/96/28427 (Buckman et al.) describes benzamidine derivatives. These compounds are stated to be factor Xa inhibitors, thereby being useful as anticoagulants.

PCT Published Patent Application WO/96/28427 (Arnaiz et al.) describes naphthyl-substituted benzimidazole derivatives. These compounds are disclosed as being factor Xa inhibitors, thereby being useful as anticoagulants.

PCT Published Patent Application WO/97/29067 (Kochanny et al.) describes benzamidine derivatives that are substituted by amino acid and hydroxy acid derivatives. These compounds are stated to be factor Xa inhibitors, thereby being useful as anticoagulants.

U.S. Pat. No. 5,869,501 (Hirayama et al.) describes amidinonaphthyl derivatives and their use as factor Xa inhibitors.

The above references, published patent applications and U.S. patents are herein incorporated in full by reference.

SUMMARY OF THE INVENTION

This invention is directed to compounds or their pharmaceutically acceptable salts which inhibit human factor Xa and are therefore useful as pharmacological agents for the treatment of disease-states characterized by thrombotic activity.

Accordingly, in one aspect, this invention provides compounds of formula (I):

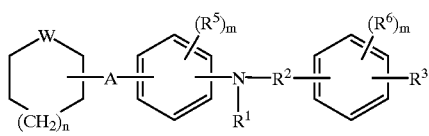

(I)

wherein:

A is —O— or —N($R^7$)—;

W is —N($R^4$)—, —S— or —O—;

each m is independently 0, 1, 2, 3 or 4;

n is 0 or 1;

$R^1$ is hydrogen, alkyl, alkylcarbonyl, phenylalylidenyl (wherein the phenyl group is optionally substituted by alkyl, halo, alkoxy, aralkoxy, —C(NH)—$NH_2$, —C(NH)N(H)O$R^7$, —C(NH)N(H)C(O)O$R^8$, —C(NH)N(H)C(O)$R^9$, —C(NH)N(H)S(O)$_2R^9$, or —C(NH)N(H)C(O)N(H)$R^7$), alkoxycarbonylalkyl, carboxyalkyl, aminocarbonylalkyl, monoalkylaminocarbonylalkyl, dialkylaminocarbonylalkyl, alkoxycarbonyl, phenylcarbonyl (wherein the phenyl group is optionally substituted by carboxy or alkoxycarbonyl), carboxyalkylcarbonyl, alkoxycarbonylalkylcarbonyl, aminocarbonylalkylcarbonyl, benzyl (wherein the phenyl group is optionally substituted by alkyl, halo, alkoxy, aralkoxy, —C(NH)—$NH_2$, —C(NH)N(H)O$R^7$, —C(NH)N(H)C(O)O$R^9$, —C(NH)N(H)C(O)$R^9$, —C(NH)N(H)S(O)$_2R^9$, or —C(NH)N(H)C(O)N(H)$R^7$), mono[dialkoxycarbonyl]alkylaminocarbonyl, mono[dicarboxy]alkylaminocarbonyl; alkylsulfonyl, arylsulfonyl or dialkylaminosulfonyl;

$R^2$ is —[C($R^7$)$_2$]$_m$—, —[C($R^7$)$_2$]$_m$—C(O)—N($R^8$)—, or —[C($R^7$)$_2$]$_m$—[C($R^8$)]=CH—; or $R^2$ is

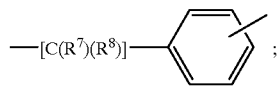

$R^3$ is —C(NH)$NH_2$, —C(NH)N(H)O$R^7$, —C(NH)N(H)C(O)O$R^9$, —C(NH)N(H)C(O)$R^9$, —C(NH)N(H)S(O)$_2R^9$, or —C(NH)N(H)C(O)N(H)$R^7$;

$R^4$ is hydrogen, alkyl, alkylcarbonyl, aminocarbonyl, monoalkylaminocarbonyl, dialkylaminocarbonyl, aminosulfonyl, alkoxycarbonyl, carboxyalkyl, alkoxycarbonylalkyl, or —C(NH)$CH_3$.

each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl;

$R^6$ is hydrogen, alkyl, hydroxy, alkoxy, aralkoxy (wherein the aryl group is optionally substituted by alkyl, halo or alkoxy);

each $R^7$ and $R^8$ is independently hydrogen, alkyl, aryl, or aralkyl; and each $R^9$ is alkyl or aralkyl;

as a single stereoisomer or a mixture thereof; or a pharmaceutically acceptable salt thereof.

In another aspect, this invention provides a method of treating a human having a disease-state characterized by thrombotic activity, which method comprises administering to a human in need thereof a therapeutically effective amount of a compound of formula (I) as described above.

In another aspect, this invention provides a method of treating a human having a disease-state alleviated by the inhibition of factor Xa, which method comprises administering to a human in need thereof a therapeutically effective amount of a compound of formula (I) as described above.

In another aspect, this invention provides a method of inhibiting human factor Xa in vitro by the administration of a compound of formula (I).

DETAILED DESCRIPTION OF THE INVENTION

Definitions

As used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkylcarbonyl" refers to a radical of the formula —C(O)$R_a$ where $R_a$ is an alkyl radical as defined above, e.g., acetyl, ethylcarbonyl, n-propylcarbonyl, and the like.

"Alkoxy" refers to a radical of the formula —O$R_a$ where $R_a$ is an alkyl radical as defined above, e.g., methoxy, ethoxy, n-propoxy, 1-methylethoxy (iso-propoxy), n-butoxy, n-pentoxy, 1,1-dimethylethoxy (t-butoxy), and the like.

"Alkoxycarbonyl" refers to a radical of the formula —C(O)O$R_a$ where $R_a$ is an alkyl radical as defined above, e.g., methoxycarbonyl, ethoxycarbonyl, n-propoxycarbonyl, 1-methylethoxycarbonyl (iso-propoxycarbonyl), n-butoxycarbonyl, n-pentoxycarbonyl, 1,1-dimethylethoxycarbonyl (t-butoxycarbonyl), and the like.

"Alkoxycarbonylalkyl" refers to a radical of the formula —$R_a$C(O)O$R_a$ where each $R_a$ is independently an alkyl radical as defined above, e.g., methoxycarbonylmethyl, 2-(ethoxycarbonyl)ethyl, (n-propoxycarbonylmethyl), 1-methylethoxycarbonylmethyl (iso-propoxycarbonylmethyl), n-butoxycarbonylmethyl, n-pentoxycarbonylmethyl, 1,1-dimethylethoxycarbonylmethyl (t-butoxycarbonylmethyl), and the like.

"Alkoxycarbonylalkylcarbonyl" refers to a radical of the formula —C(O)$R_a$C(O)O$R_a$ where each $R_a$ is independently an alkyl radical as defined above, e.g., methoxycarbonylmethylcarbonyl, 2-(ethoxycarbonyl)

ethylcarbonyl, (n-propoxycarbonylmethylcarbonyl, 1-methylethoxycarbonylmethylcarbonyl (iso-propoxycarbonylmethylcarbonyl), n-butoxycarbonylmethylcarbonyl, n-pentoxycarbonylmethylcarbonyl, 1,1-dimethylethoxycarbonylmethylcarbonyl (t-butoxycarbonylmethyl)carbonyl, and the like.

"Aryl" refers to a phenyl or naphthyl radical.

"Aralkyl" refers to a radical of the formula —$R_a R_b$ where $R_a$ is an alkyl radical as defined above, substituted by $R_b$, an aryl radical, as defined above, e.g., benzyl.

"Aralkoxy" refers to a radical of the formula —$OR_c$ where $R_c$ is an aralkyl radical as defined above, e.g., benzyloxy, and the like.

"Amidino" refers to the radical —$C(NH)NH_2$.

"Aminocarbonyl" refers to the radical —$C(O)NH_2$.

"Aminosulfonyl" refers to the radical —$S(O)_2NH_2$.

"Aminocarbonylalkyl" refers to the radical —$R_a C(O)NH_2$, where $R_a$ is an alkyl radical as defined above, e.g., aminocarbonylmethyl, 2-(aminocarbonyl)ethyl, and the like.

"Aminocarbonylalkylcarbonyl" refers to the radical —$C(O)R_a C(O)NH_2$, where $R_a$ is an alkyl radical as defined above, e.g., aminocarbonylmethylcarbonyl, 2-(aminocarbonyl)ethylcarbonyl, and the like.

"Alkylsulfonyl" refers to a radical of the formula —$S(O)_2$—$R_a$ where $R_a$ is an alkyl radical as defined above, e.g., methylsulfonyl, ethylsulfonyl, t-butylsulfonyl, and the like.

"Arylsulfonyl" refers to a radical of the formula —$S(O)_2$—$R_b$ where $R_b$ is an aryl radical as defined above, e.g., phenylsulfonyl or naphthylsulfonyl.

"Carboxy" refers to the radical —$C(O)OH$.

"Carboxyalkyl" refers to a radical of the formula —$R_a C(O)OH$, where $R_a$ is an alkyl radical as defined above, e.g., carboxymethyl, 2-(carboxy)ethyl, 3-(carboxy)propyl, and the like.

"Carboxyalkylcarbonyl" refers to a radical of the formula —$C(O)R_a C(O)OH$, where $R_a$ is an alkyl radical as defined above, e.g., carboxymethylcarbonyl, 2-(carboxy)ethylcarbonyl, 3-(carboxy)propylcarbonyl, and the like.

"Dialkylamino" refers to a radical of the formula —$N(R_a)R_a$ where each $R_a$ is independently an alkyl radical as defined above, e.g., dimethylamino, methylethylamino, diethylamino, dipropylamino, ethylpropylamino, and the like.

"Dialkylaminocarbonyl" refers to a radical of the formula —$C(O)N(R_a)R_a$ where each $R_a$ is independently an alkyl radical as defined above, e.g., dimethylaminocarbonyl, methylethylaminocarbonyl, diethylaminocarbonyl, dipropylaminocarbonyl, ethylpropylaminocarbonyl, and the like.

"Dialkylaminosulfonyl" refers to a radical of the formula —$S(O)_2$—$N(R_a)R_a$ where each $R_a$ is independently an alkyl radical as defined above, e.g., dimethylaminosulfonyl, methylethylaminosulfonyl, diethylaminosulfonyl, dipropylaminosulfonyl, ethylpropylaminosulfonyl, and the like.

"Dialkylaminocarbonylalkyl" refers to a radical of the formula —$R_a C(O)N(R_a)R_a$ where each $R_a$ is independently an alkyl radical as defined above, e.g., dimethylaminocarbonylmethyl, 2-(methylethylaminocarbonyl)ethyl, diethylaminocarbonylmethyl, 3-(dipropylaminocarbonyl)propyl, 4-(ethylpropylaminocarbonyl)butyl, and the like.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Monoalkylamino" refers to a radical of the formula —$NHR_a$ where $R_a$ is an alkyl radical as defined above, e.g., methylamino, ethylamino, propylamino, and the like.

"Monoalkylaminocarbonyl" refers to a radical of the formula —$C(O)NHR_a$ where $R_a$ is an alkyl radical as defined above, e.g., methylaminocarbonyl, ethylaminocarbonyl, propylaminocarbonyl, and the like.

"Mono[dialkoxycarbonyl]alkylaminocarbonyl" refers to a radical of the formula —$C(O)N(H)[R_a(C(O)OR_a)_2]$ where each $R_a$ is independently an alkyl radical as defined above, e.g., [1,2-diethoxycarbonyl)ethyl]aminocarbonyl, and the like.

"Mono[dicarboxy]alkylaminocarbonyl" refers to a radical of the formula —$C(O)N(H)[R_a(C(O)OH)_2]$ where $R_a$ is an alkyl radical as defined above, e.g., [1,2-dicarboxy)ethyl]aminocarbonyl, and the like.

"Monoalkylaminocarbonylalkyl" refers to a radical of the formula —$R_a C(O)NHR_a$ where each $R_a$ is independently an alkyl radical as defined above, e.g., methylaminocarbonylmethyl, 2-(ethylaminocarbonyl)ethyl, 3-(propylaminocarbonyl)propyl, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Phenylalkylidenyl" refers to a radical of the formula —$R_e R_d$ where $R_d$ is a phenyl radical and $R_e$ is a straight or branched chain unsaturated divalent radical consisting solely of carbon and hydrogen atoms, having from one to six carbon atoms, wherein the unsaturation is present only as double bonds and wherein a double bond can exist between the first carbon of the chain and the rest of the molecule, e.g., ethylidene, propylidene, n-butylidene, and the like.

"Phenylcarbonyl" refers to a radical of the formula —$C(O)R_d$ where $R_d$ is a phenyl radical.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Therapeutically effective amount" refers to that amount of a compound of the invention which, when administered to a human in need thereof, is sufficient to effect treatment, as defined below, for disease-states characterized by thrombotic activity. The amount of a compound of the invention which constitutes a "therapeutically effective amount" will vary depending on the compound, the disease-state and its severity, and the age of the human to be treated, but can be determined routinely by one of ordinary skill in the art having regard to his own knowledge and to this disclosure.

"Treating" or "treatment" as used herein covers the treatment of a disease-state in a human, which disease-state is characterized by thrombotic activity, and includes:

(i) preventing the disease-state from occurring in a human, in particular, when such human is predisposed to the disease-state but has not yet been diagnosed as having it;

(ii) inhibiting the disease-state, i.e., arresting its development; or (iii) relieving the disease-state, i.e., causing regression of the disease-state.

The yield of each of the reactions described herein is expressed as a percentage of the theoretical yield.

The compounds of the invention, or their pharmaceutically acceptable salts, may have asymmetric carbon atoms, oxidized sulfur atoms or quatemized nitrogen atoms in their structure. The compounds of the invention and their pharmaceutically acceptable salts may therefore exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

The nomenclature used herein is a modified form of the I.U.P.A.C. system wherein the compounds of the invention are named as benzenamine derivatives: For example, a compound of formula (I) wherein A is —O—, W is —N($R^4$)—, n is 1, $R^1$ is 2-(carboxy)ethylcarbonyl, $R^2$ is —CH$_2$—CH=CH—, $R^3$ is —C(NH)NH$_2$, $R^4$ is methyl, $R^5$ is trifluoromethyl, and $R^6$ is hydroxy, i.e., a compound of the following formula:

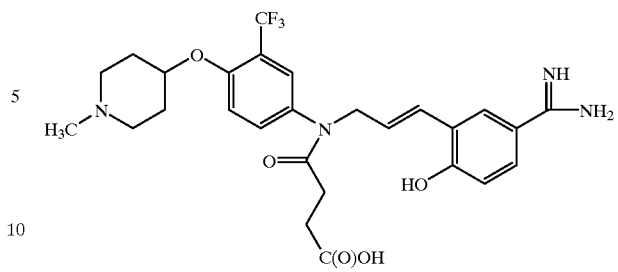

is named herein as 4-(N'-(methyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine.

Utility and Administration

A. Utility

The compounds of the invention are inhibitors of the serine protease, factor Xa, and are therefore useful in disease-states characterized by thrombotic activity based on factor Xa's role in the coagulation cascade (see Background of the Invention above). A primary indication for the compounds is prophylaxis for long term risk following myocardial infarction. Additional indications are prophylaxis of deep vein thrombosis (DVT) following orthopedic surgery or prophylaxis of selected patients following a transient ischemic attack. The compounds of the invention may also be useful for indications in which coumadin is currently used, such as for DVT or other types of surgical intervention such as coronary artery bypass graft and percutaneous transluminal coronary angioplasty. The compounds are also useful for the treatment of thrombotic complications associated with acute promyelocytic leukemia, diabetes, multiple myelomas, disseminated intravascular coagulation associated with septic shock, purpura fulminanas associated infection, adult respiratory distress syndrome, unstable angina, and thrombotic complications associated with aortic valve or vascular prosthesis. The compounds are also useful for prophylaxis for thrombotic diseases, in particular in patients who have a high risk of developing such disease.

In addition, the compounds of the invention are useful as in vitro and in vivo diagnostic reagents for selectively inhibiting factor Xa without inhibiting other components of the coagulation cascade.

B. Testing

The primary bioassays used to demonstrate the inhibitory effect of the compounds of the invention on factor Xa are simple chromogenic assays involving only serine protease, the compound of the invention to be tested, substrate and buffer (see, e.g., *Thrombosis Res.* (1979), Vol. 16, pp. 245–254). For example, four tissue human serine proteases can be used in the primary bioassay, free factor Xa, prothrombinase, thrombin (IIa) and tissue plasminogen activator (tPA). The assay for tPA has been successfully used before to demonstrate undesired side effects in the inhibition of the fibrinolytic process (see, e.g., *J. Med. Chem.* (1993), Vol. 36, pp. 314–319).

Another bioassay useful in demonstrating the utility of the compounds of the invention in inhibiting factor Xa demonstrates the potency of the compounds against free factor Xa in citrated plasma. For example, the anticoagulant efficacy of the compounds of the invention will be tested using either the prothrombin time (PT), or activated partial thromboplastin time (aPTT) while selectivity of the compounds is checked with the thrombin clotting time (TCT) assay. Correlation of the $K_i$ in the primary enzyme assay with the $K_i$ for free factor Xa in citrated plasma will screen against compounds which interact with or are inactivated by other plasma components. Correlation of the $K_i$ with the extension of the PT is a necessary in vitro demonstration that potency in the free factor Xa inhibition assay translates into potency in a clinical coagulation assay. In addition, extension of the PT in citrated plasma can be used to measure duration of action in subsequent pharmacodynamic studies.

For further information on assays to demonstrate the activity of the compounds of the invention, see R. Lottenberg et al., *Methods in Enzymology* (1981), Vol. 80, pp. 341–361, and H. Ohno et al., *Thrombosis Research* (1980), Vol. 19, pp. 579–588.

C. General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as thelan active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state alleviated by the inhibition of factor Xa in accordance with the teachings of this invention.

The compounds of the invention, or their pharmaceutically acceptable salts, are administered in a therapeutically effective amount which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-states; and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

PREFERRED EMBODIMENTS

Of the compounds of formula (I) as described in the Summary of the Invention, one preferred group of compounds are those compounds wherein A is —O—; W is —N($R^4$)—; each m is independently 0, 1 or 2; n is 1; $R^2$ is —[C($R^7$)$_2$]$_m$—C(O)—N($R^8$)—; and $R^3$ is —C(NH)NH$_2$.

Of this group of compounds, more preferred compounds are selected from the group consisting of the following:

4-(N"-(1-iminoethyl)piperidin-4-yl)oxy-N-(N'-(3-amidinophenyl)aminocarbonyl)methylbenzenamine;

4-(piperidin-4-yl)oxy-N-(N'-(6-hydroxy-3-amidinophenyl) aminocarbonyl)methylbenzenamine;

4-(N"-(1-iminoethyl)piperidin-4-yl)oxy-N-(N'-(6-hydroxy-3-amidinophenyl)aminocarbonyl)methylbenzenamine;

4-(N"-(acetyl)piperidin-4-yl)oxy-N-(N'-(6-hydroxy-3-amidinophenyl)aminocarbonyl)methylbenzenamine;

4-(N"-(1-iminoethyl)piperidin-4-yl)oxy-N-(aminocarbonylmethyl)-N-((N'-(3-amidinophenyl) amino)carbonyl)methylbenzenamine;

4-(N"-(1-iminoethyl)piperidin-4-yl)oxy-N-(1-(N'-(3-amidinophenyl)aminocarbonyl)ethyl)benzenamine;

4-(N"-(1-iminoethyl)piperidin-4-yl)oxy-N-(ethoxycarbonylmethyl)-N-((N'-(3-amidinophenyl) amino)carbonyl)methylbenzenamine;

4-(N"-(1-iminoethyl)piperidin-4-yl)oxy-N-(methyl)-N-((N'-(3-amidinophenyl)amino)carbonyl)methylbenzenamine;

4-(N"-(1-iminoethyl)piperidin-4-yl)oxy-N-(ethoxycarbonylmethyl)-N-(N'-(6-hydroxy-3-amidinophenyl)aminocarbonyl)-methylbenzenamine;

4-(N"-(1-iminoethyl)piperidin-4-yl)oxy-N-(methyl)-N-(N'-(6-hydroxy-3-amidinophenyl)aminocarbonyl)-methylbenzenamine;

4-(piperidin-4-yl)oxy-3-trifluoromethyl-N-(N'-(6-hydroxy-3-amidinophenyl)aminocarbonyl)methylbenzenamine;

4-(N"-(1-iminoethyl)piperidin-4-yl)oxy-3-carboxy-N-(N'-(6-hydroxy-3-amidinophenyl)aminocarbonyl)methylbenzenamine;

4-(N"-(1-iminoethyl)piperidin-4-yl)oxy-3-trifluoromethyl-N-(2-(carboxy)ethylcarbonyl)-N-(N'-(3-amidinophenyl)aminocarbonyl)methylbenzenamine;

4-(N"-(1-iminoethyl)piperidin-4-yl)oxy-3-trifluoromethyl-N-(2-(carboxy)ethylcarbonyl)-N-(N'-(6-hydroxy-3-amidinophenyl)aminocarbonyl)methylbenzenamine;

4-(N"-(methyl)piperidin-4-yl)oxy-N-(N'-(6-hydroxy-3-amidinophenyl)aminocarbonyl)methylbenzenamine;

4-(N"-(methyl)piperidin-4-yl)oxy-3-trifluoromethyl-N-(N'-(6-hydroxy-3-amidinophenyl)aminocarbonyl)methylbenzenamine;

4-(N"-(methyl)piperidin-4-yl)oxy-N-(1-methylethyl)-N-(N'-(6-benzyloxy-3-amidinophenyl)aminocarbonyl)methylbenzenamine;

4-(N"-(methyl)piperidin-4-yl)oxy-N-(1-methylethyl)-N-(N'-(6-hydroxy-3-amidinophenyl)aminocarbonyl)methylbenzenamine;

4-(N"-(methyl)piperidin-4-yl)oxy-3-trifluoromethyl-N-(1-methylethyl)-N-(N'-(6-hydroxy-3-amidinophenyl)aminocarbonyl)methylbenzenamine; and 4-(N"-(methyl)piperidin-4-yl)oxy-3-trifluoromethyl-N-(N'-(6-hydroxy-3-amidinophenyl)aminocarbonyl)methylbenzenamine.

Another preferred group of compounds of the compounds of formula (I) as defined above in the Summary of the Invention is the group of compounds wherein A is —O—; W is —N($R^4$)—; each m is independently 0, 1 or 2; n is 1; $R^2$ is —[C($R^7$)$_2$]$_m$—; and $R^3$ is —C(NH)NH$_2$.

Of this group of compounds, more preferred compounds are those compounds selected from the list consisting of the following:

4-(piperidin-4-yl)oxy-N-(3-(6-hydroxy-3-amidinophenyl)propyl)benzenamine;

4-(N'-(1-iminoethyl)piperidin-4-yl)oxy-3-trifuoromethyl-N-(2-(carboxy)ethylcarbonyl)-N-(3-(6-hydroxy-3-amidinophenyl)propyl)benzenamine;

4-(N'-methylpiperidin-4-yl)oxy-N-(3-(6-hydroxy-3-amidinophenyl)propyl)benzenamine;

4-(piperidin-4-yl)oxy-3-trifluoromethyl-N-(3-(6-hydroxy-3-amidinophenyl)propyl)benzenamine;

4-(N'-(1-iminoethyl)piperidin-4-yl)oxy-3-trifluoromethyl-N-(3-(6-hydroxy-3-amidinophenyl)propyl)benzenamine;

4-(piperidin-4-yl)oxy-N-(2-methyl-3-amidinophenyl)prop-1-yl)benzenamine;

4-(N'-(1-iminoethyl)piperidin-4-yl)oxy-N-(2-methyl-3-(6-hydroxy-3-amidinophenyl)prop-1-yl)benzenamine;

4-(N'-(actyl)piperidin-4-yl)oxy-3-trifluoromethyl-N-(2-(ethoxycarbonyl)ethylcarbonyl)-N-(2-methyl-3-(6-hydroxy-3-amidinophenyl)prop-1-yl)benzenamine; and 4-(N'-(actyl)piperidin-4-yl)oxy-3-trifluoromethyl-N-(2-(carboxy)ethylcarbonyl)-N-(2-methyl-3-(6-hydroxy-3-amidinophenyl)prop-1-yl)benzenamine.

Another preferred group of compounds of the compounds of formula (I) as defined above in the Summary of the Invention is the group of compounds wherein A is —O—; W is —N($R^4$)—; each m is independently 0, 1 or 2; n is 1; $R^2$ is —[C($R^7$)$_2$]$_m$—[C($R^8$)]=CH—; $R^3$ is —C(NH)NH$_2$; and $R^8$ is hydrogen.

Of this group of compounds, more preferred compounds are those compounds selected from the list consisting of the following:

4-(N'-(1-iminoethyl)piperidin-4-yl)oxy-3-nitro-N-(3-(3-amidinophenyl)prop-2-en-1-yl)benzenamine;

4-(N'-(1-iminoethyl)piperidin-4-yl)oxy-N-(3-(3-amidinophenyl)prop-2-en-1-yl)benzenamine;

4-(N'-(1-iminoethyl)piperidin-4-yl)oxy-N-(3-(3-amidinophenyl)prop-2-en-1-yl)-N-(3-(3-amidinophenyl)prop-2-en-1-yl)benzenamine;

4-(N'-(1-iminoethyl)piperidin-4-yl)oxy-3-nitro-N-(carboxymethyl)-N-(3-(3-amidinophenyl)prop-2-en-1-yl)benzenamine;

4-(N'-(1-iminoethyl)piperidin-4-yl)oxy-3-trifluoromethyl-N-(3-(3-amidinophenyl)prop-2-en-1-yl)benzenamine;

4-(N'-(1-iminoethyl)piperidin-4-yl)oxy-3-ethoxycarbonyl-N-(3-(3-amidinophenyl)prop-2-en-1-yl)benzenamine;

4-(N'-(1-iminoethyl)piperidin-4-yl)oxy-3-ethoxycarbonyl-N-(3-(3-amidinophenyl)prop-2-en-1-yl)-N-(3-(3-amidinophenyl)prop-2-en-1-yl)benzenamine;

4-(N'-(1-iminoethyl)piperidin-4-yl)oxy-3-fluoro-N-(3-(3-amidinophenyl)prop-2-en-1-yl)benzenamine;

4-(N'-(1-iminoethyl)piperidin-4-yl)oxy-N-(2-(ethoxycarbonyl)propyl)-N-(3-(3-amidinophenyl)prop-2-en-1-yl)benzenamine;

4-(piperidin-4-yl)oxy-3-(ethoxycarbonyl)-N-(3-(3-amidinophenyl)prop-2-en-1-yl)benzenamine;

4-(piperidin-4-yl)oxy-3-(ethoxycarbonyl)-N-(3-(3-amidinophenyl)prop-2-en-1-yl)-N-(3-(3-amidinophenyl)prop-2-en-1-yl)benzenamine;

4-(N'-(1-iminoethyl)piperidin-4-yl)oxy-3-ethoxycarbonyl-N-(ethoxycarbonylmethyl)-N-(3-(3-amidinophenyl)prop-2-en-1-yl)benzenamine;

4-(piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3,5-difluoro-N-(3-(3-amidinophenyl)prop-2-en-1-yl)benzenamine;

4-(N'-acetylpiperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-trifluoromethyl-N-(3-(6-hydroxy-3-amidinophenyl)prop-2-en-1-yl)benzenamine;

4-(piperidin-4-yl)oxy-3-trifluoromethyl-N-(3-(6-benzyloxy-3-amidinophenyl)prop-2-en-1-yl)benzenamine;

4-(piperidin-4-yl)oxy-N-(3-(6-hydroxy-3-amidinophenyl)prop-2-en-1-yl)benzenamine;

4-(N'-(1-iminoethyl)piperidin-4-yl)oxy-3,5-difluoro-N-(3-(3-amidinophenyl)prop-2-en-1-yl)benzenamine;

4-(N'-(1-iminoethyl)piperidin-4-yl)oxy-N-(1-methylethyl)-N-(3-(3-amidinophenyl)prop-2-en-1-yl)benzenamine;

4-(N'-(1-iminoethyl)piperidin-4-yl)oxy-N-(3-(6-hydroxy-3-amidinophenyl)prop-2-en-1-yl)benzenamine;

4-(N'-(1-iminoethyl)piperidin-4-yl)oxy-3-fluoro-N-(methoxycarbonylmethyl)-N-(3-(3-amidinophenyl)prop-2-en-1-yl)benzenamine;

4-(N'-(1-iminoethyl)piperidin-4-yl)oxy-3-trifluoromethyl-N-(methoxycarbonylmethyl)-N-(3-(3-amidinophenyl)prop-2-en-1-yl)benzenamine;

4-(N'-(1-iminoethyl)piperidin-4-yl)oxy-3-trifluoromethyl-N-(methyl)-N-(3-(3-amidinophenyl)prop-2-en-1-yl)benzenamine;

4-(N'-(1-iminoethyl)piperidin-4-yl)oxy-3-trifluoromethyl-N-(aminocarbonylmethyl)-N-(3-(3-amidinophenyl)prop-2-en-1-yl)benzenamine;

4-(N'-(1-iminoethyl)piperidin-4-yl)oxy-3-fluoro-N-(aminocarbonylmethyl)-N-(3-(3-amidinophenyl)prop-2-en-1-yl)benzenamine;

4-(N'-(1-iminoethyl)piperidin-4-yl)oxy-3-nitro-N-(2-(carboxy)ethylcarbonyl)-N-(3-(3-amidinophenyl)prop-2-en-1-yl)benzenamine;

4-(piperidin-4-yl)oxy-3-carboxy-N-(3-(3-amidinophenyl)prop-2-en-1-yl)benzenamine;

4-(piperidin-4-yl)oxy-3-methoxycarbonyl-N-(3-(3-amidinophenyl)prop-2-en-1-yl)benzenamine;

4-(N'-(1-iminoethyl)piperidin-4-yl)oxy-3-carboxy-N-(3-(3-amidinophenyl)prop-2-en-1-yl)benzenamine;

4-(N'-(1-iminoethyl)piperdin-4-yl)oxy-3-methoxycarbonyl-N-(3-(3-amidinophenyl)prop-2-en-1-yl)benzenamine;

4-(N'-(methyl)piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-trifluoromethyl-N-acetyl-N-(3-(6-hydroxy-3-amidinophenyl)prop-2-en-1-yl)benzenamine;

4-(N'-(methyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-carboxy-N-((1-methylethyl)carbonyl)-N-(3-(6-hydroxy-3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(6-hydroxy-3-amidinophenyl)prop-2-en-1-yl)benzenamine;

4-(piperidin-4-yl)oxy-3-trifluoromethyl-N-(benzyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-((1-methylethyl)carbonyl)-N-(3-(6-hydroxy-3-amidinophenyl)prop-2-en-1-yl)benzenamine;

4-(N'-(1-iminoethyl)piperidin-4-yl)oxy-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(benzyl)-N-(3-(6-hydroxy-3-amidinophenyl)prop-2-en-1-yl)benzenamine;

4-(piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(piperidin-4-yl)oxy-3-trifluoromethyl-N-acetyl-N-(3-(6-hydroxy-3-amidinophenyl)prop-2-en-1-yl)benzenamine;

4-(N'-(1-iminoethyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(acetyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(methyl)piperidin-4-yl)oxy-3-trifluoromethyl-N-(2-(methoxycarbonyl)ethylcarbonyl)-N-(3-(6-hydroxy-3-amidinophenyl)prop-2-en-1-yl)benzenamine;

4-(N'-(methyl)piperdin-4-yl)oxy-3-trifluoromethyl-N-acetyl-N-(3-(6-hydroxy-3-amidinophenyl)prop-2-en-1-yl)benzenamine;

4-(N'-(1-iminoethyl)piperidin-4-yl)oxy-3-trifuoromethyl-N-(methoxycarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(benzyl)-N-(3-(6-hydroxy-3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(3-amidinophenyl)prop-2-en-1-yl)benzenamine;

4-(N'-(1-iminoethyl)piperidin-4-yl)oxy-3-carboxy-N-((1-methylethyl)carbonyl)-N-(3-(3-amidinophenyl)prop-2-en-1-yl)benzenamine;

4-(N'-(aminocarbonyl)piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-(methoxycarbonyl)-N-(2-(methoxycarbonyl)ethylcarbonyl)-N-(3-(6-hydroxy-3-amidinophenyl)prop-2-en-1-yl)benzenamine;

4-(N'-(1-iminoethyl)piperidin-4-yl)oxy-3-carboxy-N-(2-(aminocarbonyl)ethylcarbonyl)-N-(3-(6-hydroxy-3-amidinophenyl)prop-2-en-1-yl)benzenamine;

4-(N'-(methylsulfonyl)piperidin-4-yl)oxy-3-trifluoromethyl-N-(3-(6-hydroxy-3-amidinophenyl)prop-2-en-1-yl)benzenamine;

4-(N'-(methylsulfonyl)piperidin-4-yl)oxy-3-trifluoromethyl-N-((1-methylethyl)carbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(2-(ethoxycarbonyl)ethylcarbonyl)-N-(3-(3-amidinophenyl)prop-2-en-1-yl)benzenamine;

4-(N'-(methyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(acetyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(ethoxycarbonyl)piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-(nitro)-N-(aminocarbonylmethyl)-N-(3-(3-amidinophenyl)prop-2-en-1-yl)benzenamine;

4-(N'-(ethoxycarbonylmethyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-((1,2-di(ethoxycarbonyl)ethyl)aminocarbonyl)-N-(3-(3-amidinophenyl)prop-2-en-1-yl)benzenamine;

4-(N'-(1-iminoethyl)piperidin-4-yl)oxy-3-trifluoromethyl-N-((1,2-di(carboxy)ethyl)aminocarbonyl)-N-(3-(3-amidinophenyl)prop-2-en-1-yl)benzenamine;

4-(piperidin-4-yl)oxy-3-carboxy-N-(2-(carboxy)ethylcarbonyl)-N-(3-(3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(3-amidinophenyl)prop-2-en-1-yl)benzenamine;

4-(N'-(acetyl)piperidin-4-yl)oxy-3-trifluoromethyl-N-((1,2-di(ethoxycarbonyl)ethyl)aminocarbonyl)-N-(3-(3-amidinophenyl)prop-2-en-1-yl)benzenamine;

4-(N'-(acetyl)piperidin-4-yl)oxy-3-trifluoromethyl-N-((3,4-di(ethoxycarbonyl)phenyl)carbonyl)-N-(3-(3-amidinophenyl)prop-2-en-1-yl)benzenamine;

4-(N'-(carboxymethyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(acetyl)piperidin-4-yl)oxy-3-trifluoromethyl-N-((1,2-di(carboxy)ethyl)aminocarbonyl)-N-(3-(3-amidinophenyl)prop-2-en-1-yl)benzenamine;

4-(N'-(1-iminoethyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(methyl)piperidin-4-yl)oxy-3-trifluoromethyl-N-((1,2-di(carboxy)ethyl)aminocarbonyl)-N-(3-(3-amidinophenyl)prop-2-en-1-yl)benzenamine;

4-(N'-(acetyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(1-iminoethyl)piperidin-4-yl)oxy-3-trifluoromethyl-N-((3,4-di(ethoxycarbonyl)phenyl)carbonyl)-N-(3-(3-amidinophenyl)prop-2-en-1-yl)benzenamine;

4-(N'-(methyl)piperidine-4-yl)oxy-3-trifluoromethyl-N-((3,4-di(carboxy)phenyl)carbonyl)-N-(3-(3-amidinophenyl)prop-2-en-1-yl)benzenamine;

4-(N'-(methyl)piperidin-4-yl)oxy-3-trifluoromethyl-N-((3,4-di(ethoxycarbonyl)phenyl)carbonyl)-N-(3-(3-amidinophenyl)prop-2-en-1-yl)benzenamine;

4-(N'-(carboxymethyl)piperidin-4-yl)oxy-3-trifluoromethyl-N-(2-(carboxy)ethylcarbonyl)-N-(3-(3-amidinophenyl)prop-2-en-1-yl)benzenamine;

4-(N'-(carboxymethyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(carboxymethyl)piperidin-4-yl)oxy-3-trifluoromethyl-N-(3-(3-amidinophenyl)prop-2-en-1-yl)benzenamine;

4-(piperidin-4-yl)oxy-3-(ethoxycarbonyl)-N-(3-(3-amidinophenyl)prop-2-en-1-yl)-N-(3-(3-amidinophenyl)prop-2-en-1-yl)benzenamine; and 4-(piperidin-4-yl)oxy-3-trifluoromethyl-N-(3-(6-benzyloxy-3-amidinophenyl)prop-2-en-1-yl)-N-(3-(6-benzyloxy-3-amidinophenyl)prop-2-en-1-yl)benzenamine.

Another preferred group of compounds of the compounds of formula (I) as defined above in the Summary of the Invention is the group of compounds wherein A is —O—; W is —N(R⁴)—; each m is independently 0, 1 or 2; n is 1; R² is —[C(R⁷)₂]ₘ—[C(R⁸)]=CH—; R³ is —C(NH)NH₂; and R⁸ is methyl.

Of this group of compounds, more preferred compounds are those compounds selected from the list consisting of the following:

4-(N'-(1-iminoethyl)piperidin-4-yl)oxy-3-(nitro)-N-(2-methyl-3-(3-amidinophenyl)prop-2-en-1-yl)benzenamine;

4-(piperidin-4-yl)oxy-N-(2-methyl-3-(6-hydroxy-3-amidinophenyl)prop-2-en-1-yl)benzenamine;

4-(piperidin-4-yl)oxy-N-(2-methyl-3-(6-benzyloxy-3-amidinophenyl)prop-2-en-1-yl)benzenamine;

4-(N'-(1-iminoethyl)piperidin-4-yl)oxy-N-(2-methyl-3-(6-hydroxy-3-amidinophenyl)prop-2-en-1-yl)benzenamine;

4-(N'-(acetyl)piperidin-4-yl)oxy-N-(2-methyl-3-(6-hydroxy-3-amidinophenyl)prop-2-en-1-yl)benzenamine;

4-(N'-(1-iminoethyl)piperidin-4-yl)oxy-N-(2-methyl-3-(6-benzyloxy-3-amidinophenyl)prop-2-en-1-yl)benzenamine;

4-(piperidin-4-yl)oxy-3-carboxy-N-(2-(carboxy)ethylcarbonyl)-N-(2-methyl-3-(3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(2-methyl-3-(6-hydroxy-3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(2-methyl-3-(3-amidinophenyl)prop-2-en-1-yl)benzenamine; and 4-(N'-(carboxymethyl)piperidin-4-yl)oxy-3-trifluoromethyl-N-(2-(carboxy)ethylcarbonyl)-N-(2-methyl-3-(6-hydroxy-3-amidinophenyl)prop-2-en-1-yl)benzenamine.

Another preferred group of compounds of the compounds of formula (I) as defined above in the Summary of the Invention is the group of compounds wherein A is —O—; W is —N(R⁴)—; each m is independently 0, 1 or 2; n is 1; R² is

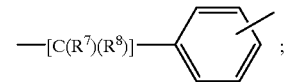

and R³ is —C(NH)NH₂.

Of this group of compounds, more preferred compounds are those compounds selected from the list consisting of the following:

4-(N'-(1-iminoethyl)piperidin-4-yl)oxy-3-nitro-N-(3-(3-amidinophenyl)benzyl)benzenamine;

4-(N'-(acetyl)piperidin-4-yl)oxy-3-methoxy-N-(3-(3-amidinophenyl)benzyl)benzenamine;

4-(N'-(1-iminoethyl)piperidin-4-yl)oxy-N-(3-(3-amidinophenyl)benzyl)benzenamine;

4-(piperidin-4-yl)oxy-3-(ethoxycarbonyl)-N-(3-(3-amidinophenyl)benzyl)benzenamine;

4-(N'-(1-iminoethyl)piperidin-4-yl)oxy-3-(ethoxycarbonyl)-N-(3-(3-amidinophenyl)benzyl)benzenamine;

4-(N'-(1-iminoethyl)piperidin-4-yl)oxy-3-carboxy-N-(3-(3-amidinophenyl)benzyl)benzenamine;

4-(piperidin-4-yl)oxy-3-(ethoxycarbonyl)-N-(ethoxycarbonylmethyl)-N-(3-(3-amidinophenyl)benzyl)benzenamine;

4-(N'-(1-iminoethyl)piperidin-4-yl)oxy-3-(ethoxycarbonyl)-N-(ethoxycarbonylmethyl)-N-(3-(3-amidinophenyl)benzyl)benzenamine;

4-(N'-(1-iminoethyl)piperidin-4-yl)oxy-3-carboxy-N-(carboxymethyl)-N-(3-(3-amidinophenyl)benzyl)benzenamine;

4-(N'-(1-iminoethyl)piperidin-4-yl)oxy-3-trifluoromethyl-N-(3-(3-amidinophenyl)benzyl)benzenamine;

4-(piperidin-4-yl)oxy-3-trifluoromethyl-N-(3-(3-amidinophenyl)benzyl)benzenamine;

4-(N'-(1-iminoethyl)piperidin-4-yl)oxy-3-trifluoromethyl-N-(ethoxycarbonylmethyl)-N-(3-(3-amidinophenyl)benzyl)benzenamine;

4-(N'-(1-iminoethyl)piperidin-4-yl)oxy-3-(ethoxycarbonyl)-N-(3-(3-amidinophenyl)benzyl)-N-(3-(3-amidinophenyl)benzyl)benzenamine; and 4-(N'-(1-iminoethyl)piperidin-4-yl)oxy-3-carboxy-N-(3-(3-amidinophenyl)benzyl)-N-(3-(3-amidinophenyl)benzyl)benzenamine.

Another preferred group of compounds of the compounds of formula (I) as defined above in the Summary of the Invention is the group of compounds wherein A is —O—; W is —O— or —S—; each m is independently 0, 1 or 2; n is 1; R² is —[C(R⁷)₂]ₘ—[C(R⁸)]=CH—; and R³ is —C(NH)NH₂.

Of this group of compounds, more preferred compounds are those compounds selected from the list consisting of the following:

4-(tetrahydropyran-4-yl)oxy-3-trifluoromethyl-N-(3-(6-hydroxy-3-amidinophenyl)prop-2-en-1-yl)benzenamine; and 4-(thian-4-yl)oxy-3-trifluoromethyl-N-(3-(6-hydroxy-3-amidinophenyl)prop-2-en-1-yl)benzenamine.

Of the preferred compounds named above, the most preferred compounds are selected from the group consisting of the following:

4-(N'-(1-iminoethyl)piperidin-4-yl)oxy-3-nitro-N-(carboxymethyl)-N-(3-(3-amidinophenyl)prop-2en-1-yl)benzenamine;

4-(N'-(1-iminoethyl)piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-nitro-N-(2-(carboxy)ethylcarbonyl)-N-(3-(3-amidinophenyl)prop-2-en-1-yl)benzenamine;

4-(N'-(methyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-((1,2-di(carboxy)ethyl)aminocarbonyl)-N-(3-(3-amidinophenyl)prop-2-en-1-yl)benzenamine;

4-(N'-(carboxymethyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(carboxymethyl)piperidin-4-yl)oxy-3-trifluoromethyl-N-(2-(carboxy)ethylcarbonyl)-N-(3-(3-amidinophenyl)prop-2-en-1-yl)benzenamine;

4-(N'-(carboxymethyl)piperidin-4-yl)oxy-3-trifluoromethyl-N-(2-(carboxy)ethylcarbonyl)-N-(2-methyl-3-(6-hydroxy-3-amidinophenyl)prop-2-en-1-yl)benzenamine;

4-(N'-(carboxymethyl)piperidin-4-yl)oxy-3-trifluoromethyl-N-((3,4-di(carboxy)phenyl)carbonyl)-N-(3-(3-amidinophenyl)prop-2-en-1-yl)benzenamine, and 4-(N''-(1-iminoethyl)piperidin-4-yl)oxy-3-trifluoromethyl-N-(2-(carboxy)ethylcarbonyl)-N-(N'-(3-amidinophenyl)aminocarbonyl)methylbenzenamine.

PREPARATION OF COMPOUNDS OF THE INVENTION

As a matter of convenience, the following Reaction Schemes are directed to the preparation of compounds of formula (I) where W is —N(R⁴)—. It is also understood that in the following Reaction Schemes combinations of substituents and/or variables (e.g., $R^5$ or $R^6$) on the depicted formulae are permissible only if such combinations result in stable compounds.

In the following Reaction Scheme 1 depicting the preparation of compounds of formula (D), which are intermediates in the preparation of the compounds of the invention, A is —O— or —N(R⁷)—; m is 0 to 4 and each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; Boc is t-butoxycarbonyl; and $R^7$ is hydrogen, alkyl, aryl, or aralkyl.

REACTION SCHEME 1

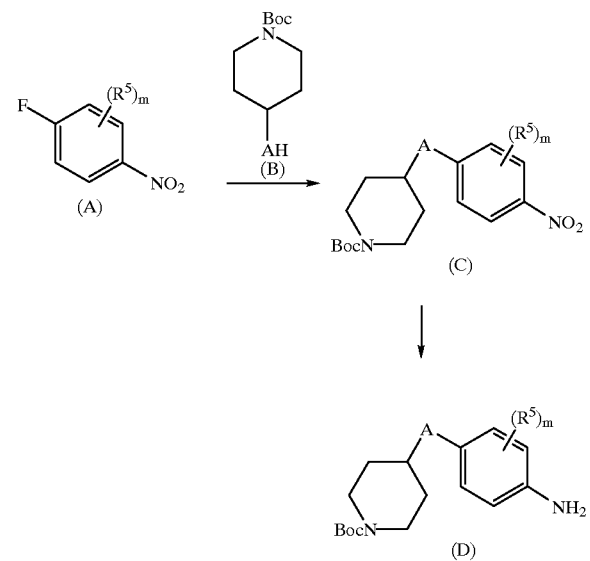

Compounds of formula (A) and formula (B) are commercially available or may be prepared according to methods known to those of ordinary skill in the art.

In general, compounds of formula (D) are prepared by first treating a compound of formula (A) in an aprotic solvent, for example, dimethylformamide, with a base, such as sodium hydride, at ambient temperature. The reaction mixture is allowed to stir at ambient temperature for 1–4 hours, preferably for 2 hours. To the reaction mixture is added a compound of formula B and the resulting reaction mixture is allowed to stir at ambient temperature for 8 to 12 hours. The compound of formula (C) is isolated from the reaction mixture by standard isolation techniques, such as extraction, concentration and purification by flash chromatography.

The compound of formula (C) so formed is then reduced under standard hydrogenation conditions (Pd/C) to form a compound of formula (D).

In the following Reaction Scheme 2 depicting the preparation of compounds of formula (H), which are intermediates in the preparation of the compounds of the invention, m is 0 to 4; and each $R^6$ is hydrogen, alkyl, hydroxy, alkoxy, aralkoxy (wherein the aryl group is optionally substituted by alkyl, halo or alkoxy).

REACTION SCHEME 2

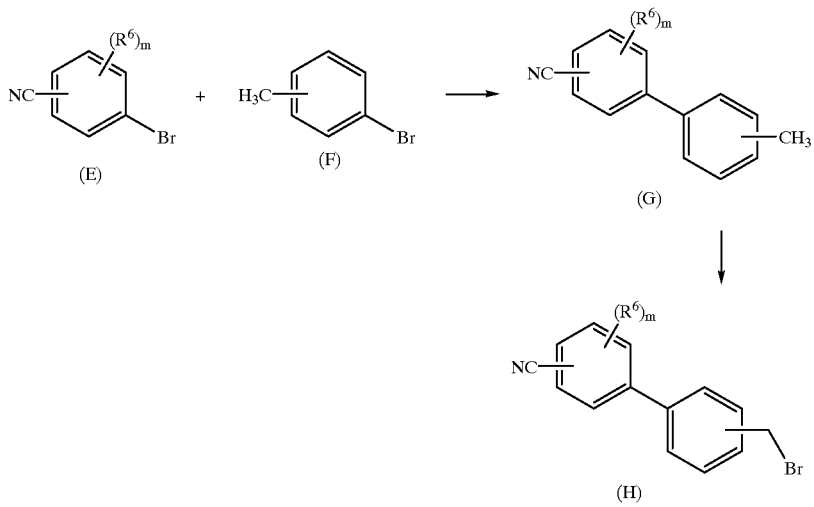

Compounds of formula (E) and formula (F) are commercially available or may be prepared according to methods known to those skilled in the art.

In general, compounds of formula (H) are prepared by first treating a compound of formula (E) in a polar solvent, such as dioxane, with an alkyl tin, such as hexamethylditin, in the presence of a catalyst, such as triphenylphosphine palladium under standard coupling reactions conditions. The compound of formula (F) is then added to the reaction mixture under similar conditions. The compound of formula (G) is then isolated from the reaction mixture by standard isolation techniques, such as extraction, concentration and purification by flash chromatography.

The compound of formula (G) is then treated with a brominating agent, such as NBS, in the presence of a radical initiator, such benzoylperoxide, in an aprotic solvent, such as tetrachloromethane. The resulting solution is heated at reflux for about 10 to 15 hours, preferably for about 15 hours. The solvent is removed and the compound of formula (H) is isolated by flash chromatography.

In the following Reaction Scheme 3 depicting the preparation of compounds of formula (M), which are intermediates in the preparation of the compounds of the invention, A is —O— or —N(R$^7$)—; m is 1 to 4; each R$^5$ is hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; and R$^7$ is hydrogen, alkyl, aryl, or aralkyl.

REACTION SCHEME 3

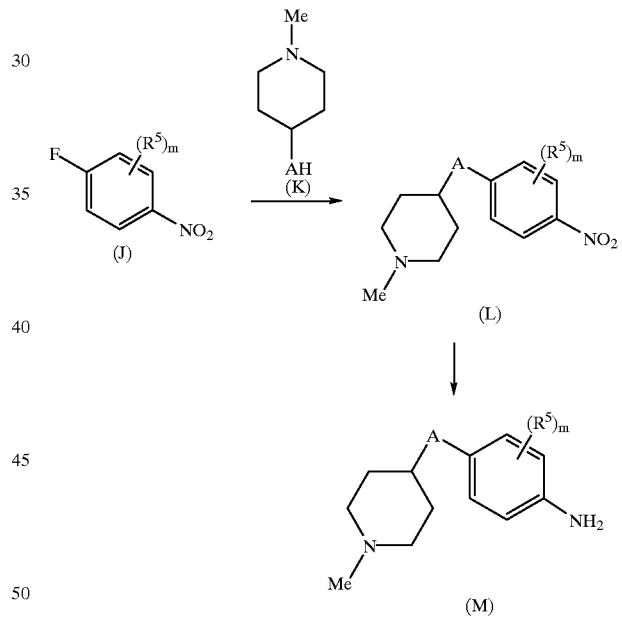

Compounds of formula (J) and formula (K) are commercially available or may be prepared according to methods known to those skilled in the art.

In general, the compounds of formula (M) are made in a similar manner to the compounds of formula (D) as described above in Reaction Scheme 1.

In the following Reaction Scheme 4 depicting the preparation of compounds of formula (Q), which are intermediates in the preparation of the compounds of the invention, m is 1 to 4; each R$^6$ is hydrogen, alkyl, hydroxy, alkoxy, aralkoxy (wherein the aryl group is optionally substituted by alkyl, halo or alkoxy); and $R^8$ is independently hydrogen, alkyl, aryl, or aralkyl.

REACTION SCHEME 4

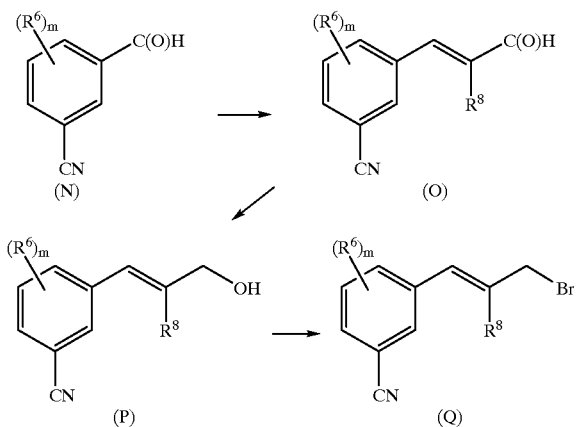

Compounds of formula (N) are commercially available or may be prepared according to methods known to those skilled in the art.

In general, compounds of formula (Q) are prepared by first treating a compound of formula (N) in an organic solvent, such as methylene chloride, with the appropriate Wittig reagent, such as (triphenylphosphoranylidene) acetaldehyde. The reaction mixture is stirred at reflux for 12 to 16 hours, preferably for about 16 hours. The reaction mixture is then cooled, and the compound of formula (O) is isolated from the reaction mixture by standard isolation techniques, such concentration and purification by flash chromatography.

The compound of formula (O) in an organic solvent, such as methanol, is then treated optionally with a chelating agent, such as $CeCl_3$, and the reaction mixture was stirred for 30 minutes to 1 hour, preferaby for about 1 hour, at 0° C. A reducing agent, such as sodium borohydride, is then added, and the resulting mixture is stirred for an additional hour at 0° C. The mixture is concentrated and resulting residue is dissolved in an aqueous basic solution, such as aqueous $NaHCO_3$. The compound of formula (P) is isolated from the solution by extraction, concentrated and purification by flash chromatography.

The compound of formula (P) is then treated with brominating agent, such as triphenyphosphine bromine complex, at ambient temperature. The resulting solution is stirred at 50° C. to about 60° C., preferably at 60° C., for about 30 minutes to an hour, preferably for about 30 minutes. The reaction mixture is cooled to ambient temperature and concentrated. The compound of formula (Q) is isolated from the reaction mixture by trituration, filtration and concentration.

In the following Reaction Scheme 5 depicting the preparation of compounds of formula (W), intermediates in the preparation of compounds of the invention, $R^8$ is independently hydrogen, alkyl, aryl, or aralkyl.

REACTION SCHEME 5

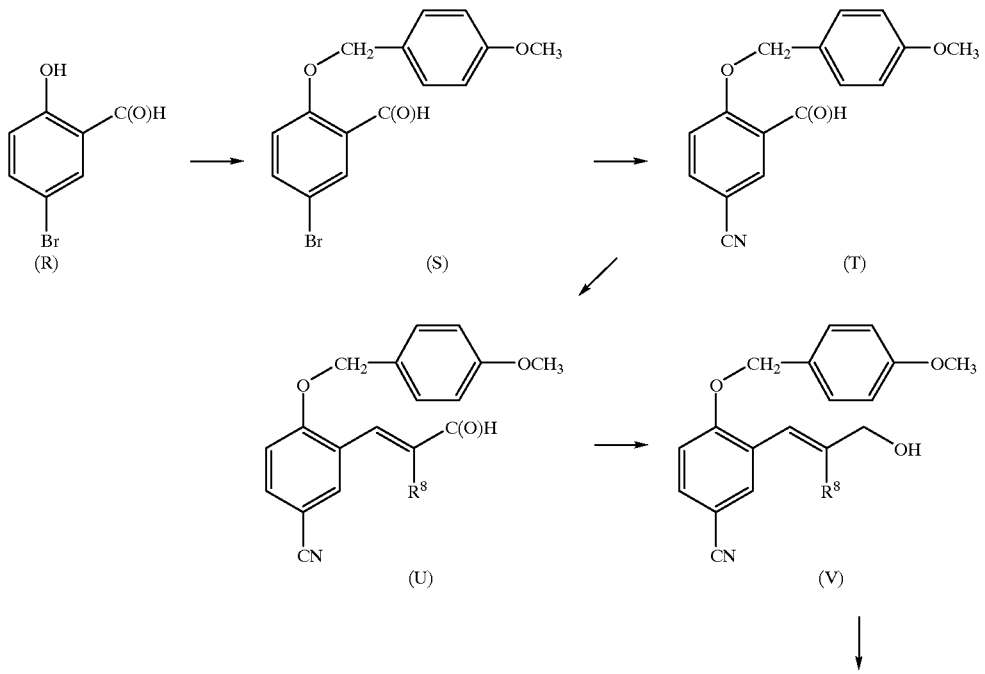

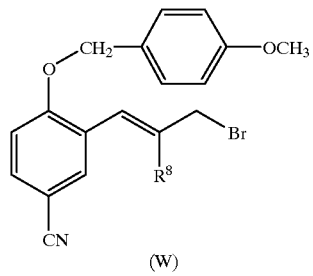

(W)

Compounds of formula (R) are commercially available or may be prepared according to methods known to those skilled in the art.

In general, compounds of formula (W) are prepared by first treating a compound of formula (R) in an aprotic solvent, such as methylene chloride, with a base, such as sodium hydride. The reaction mixture is stirred for 30 minutes to an hour, preferably for about 30 minutes, at ambient temperature. A protecting-group providing agent, such as 4-methoxybenzyl chloride is then added and the resulting reaction mixture is stirred for about 8 to 20 hours, preferably for about 16 hours, at ambient temperature. The mixture is then diluted with water and the organic layer was isolated by extraction. The compound of formula (S) was isolated form the organic layer by concentration and purification by flash chromatgraphy.

The compound of formula (S) so formed is then treated with a cyanide containing agent, such as $Zn(CN)_2$, in the presense of a catalyst, such as $Pd(PPH_3)_4$, in an organic solvent, such as dimethylformamide. The resulting reaction mixture is stirred at around 90° C. for 2 to 4 hours, preferably for about 3 hours, and then cooled to ambient temperature and diluted with an aqueous basic solution, such as 50% $NH_4OH$. The compound of formula (T) is isolated from the reaction mixture by standard isolation techniques, such as extraction, concentration and purification by flash chromatography.

The compound of formula (T) is then treated in a similar manner as described above for the compounds of formula (N) to form a compound of formula (U). The compound of formula (U) is then treated in a similar manner as described above for the compounds of formula (O) to form a compound of formula (V). The compound of formula (V) is then treated in a similar manner as described for compounds of formula (P) to form the compound of formula (W).

In the following Reaction Scheme 6 depicting the preparation of compounds of formula (Y), which are intermediates of the compounds of the invention, each m is independently 0 to 4; A is —O— or —N($R^7$)—; each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; each $R^6$ is hydrogen, alkyl, hydroxy, alkoxy, aralkoxy (wherein the aryl group is optionally substituted by alkyl, halo or alkoxy); Boc is t-butoxycarbonyl; $R^7$ is hydrogen, alkyl, aryl, or aralkyl; $R^8$ is hydrogen, alkyl, aryl, or aralkyl; and $R^1$ is alkyl, alkoxycarbonylalkyl, carboxyalkyl, aminocarbonylalkyl, monoalkylaminocarbonylalkyl, dialkylaminocarbonylalkyl, benzyl (wherein the phenyl group is optionally substituted by alkyl, halo, alkoxy, aralkoxy, cyano).

REACTION SCHEME 6

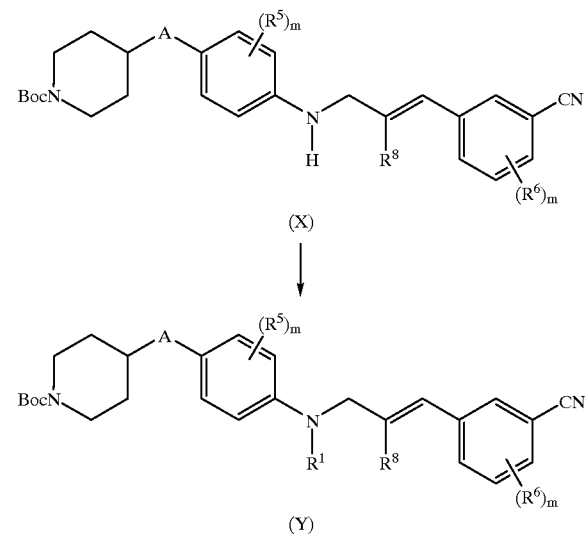

Compounds of formula (X) may be prepared according to methods disclosed herein are may be prepared according to methods known to those skilled in the art.

In general, the preparation of compounds of formula (Y) from compounds of formula (X) is an alkylation procedure. For example, the compound of formula (Y) in an aprotic solvent, such as DMF, in the presence of a base, such as $K_2CO_3$, is treated with an appropriate alkylating agent, such as methyl bromoacetate. The mixture is stirred at 50° C. to about 60° C., preferably at about 55° C., for 4 to 8 hours, preferably for about 6 hours. After the reaction mixture is cooled to ambient temperature, the compound of formula (Y) is isolated from the reaction mixture by standard isolation techniques, such as extraction, concentration and purification by flash chromatography.

In the following Reaction Scheme 6a depicting the preparation of compounds of formula (Yd), which are intermediates of compounds of the invention, A is —O— or N($R^7$)—; $R^7$ is hydrogen, alkyl, aryl or aralkyl; Boc is t-butoxycarbonyl; PG is a nitrogen protecting group, e.g, trifluoromethylcarbonyl; and $R^5$ is nitro or carboxy.

REACTION SCHEME 6a

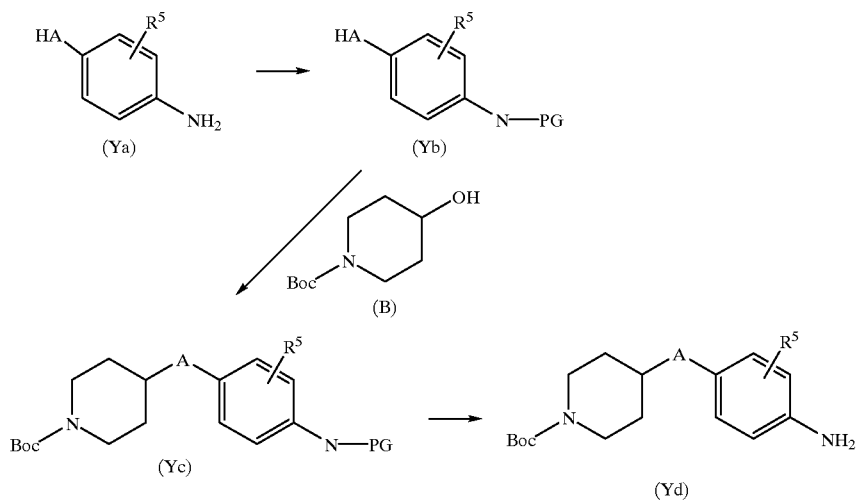

Compounds of formula (Ya) and (B) are commercially available, or can be prepared according to methods known to those of ordinary skill in the art.

In general, compounds of formula (Yd) are prepared by first treating a compound of formula (Ya) with an appropriate protecting group providing agent, such as trifluoroacetic anhydride, in an aprotic solvent, such as methylene chloride in the presence of a base, such as triethylamine, at temperatures between 0° C. and ambient temperature, preferably at 0° C. The reaction mixture is stirred at this temperature for 2 to 4 hours, preferably for about 3 hours. The reaction mixture is then diluted and neutralized and the compound of formula (Yb) is then isolated from the reaction mixture by standard isolation techniques, such as extraction, concentration and purification by flash chromatography.

The compound of formula (Yb) is then treated with a compound of formula (B) under Mitsunobu reaction conditions, i.e., to a mixture of the compound of formula (Yb) and the compound of formula (B) in a polar solvent, such as THF, in the presence of triphenylphosphine, is added DEAD dropwise. The reaction mixture is stirred at ambient temperature for 30 minutes to 1 hour, preferably for about 1 hour. The compound of formula (Yc) is then isolated from the reaction mixture by standard isolation techniques, such as concentration and purification by flash chromatography.

Under basic hydrolysis conditions, such as treating the compound of formula (Yc) in a polar solvent, such as methanol and water, with a base, such as $K_2CO_3$, from ambient temperature to 100° C., preferably at 50° C., for 1 to 20 hours, preferably for 16 hours, the compound of formula (Yd) is formed.

In the following Reaction Scheme 6b depicting the preparation of compounds of formula (Yf), which are intermediates in the preparation of compounds of the invention, A is —O— or —N($R^7$)—; $R^5$ is alkoxycarbonyl; Boc is t-butoxycarbonyl; and $R^7$ is hydrogen, alkyl, aryl or aralkyl.

REACTION SCHEME 6b

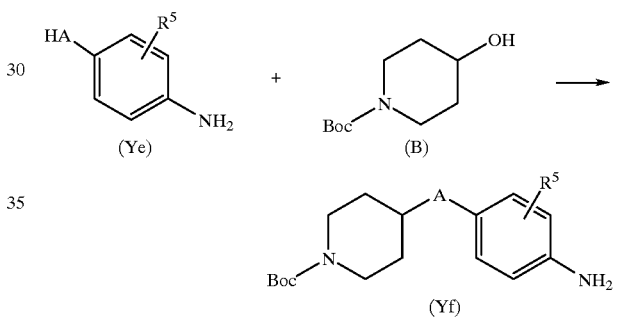

Compounds of formula (Ye) and (B) are commercially available, or may be prepared according to methods known to those skilled in the art.

In general, compounds of formula (Yf) are prepared from compounds of formula (Ye) and compounds of formula (B) in a similar manner, i.e., under Mitsunobu reaction conditions, as the compounds of formula (Yc) above.

In the following Reaction Scheme 7 depicting preparation of compounds of formula (Ie), which are compounds of the invention, A is —O— or —N($R^7$)—; m is 0 to 4 and each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; $R^1$ is alkylcarbonyl, alkoxycarbonyl, phenylcarbonyl, carboxyalkylcarbonyl, alkoxycarbonylalkylcarbonyl, aminocarbonylalkylcarbonyl, mono[dialkoxycarbonyl]alkylamino-carbonyl, mono[dicarboxy]alkylaminocarbonyl, alkylsulfonyl, arylsulfonyl or dialkylaminosulfonyl; Boc is t-butoxycarbonyl; OPMB is 4-methoxybenzyloxy; $R^7$ is hydrogen, alkyl, aryl, or aralkyl; and $R^8$ is hydrogen, alkyl, aryl, or aralkyl.

REACTION SCHEME 7

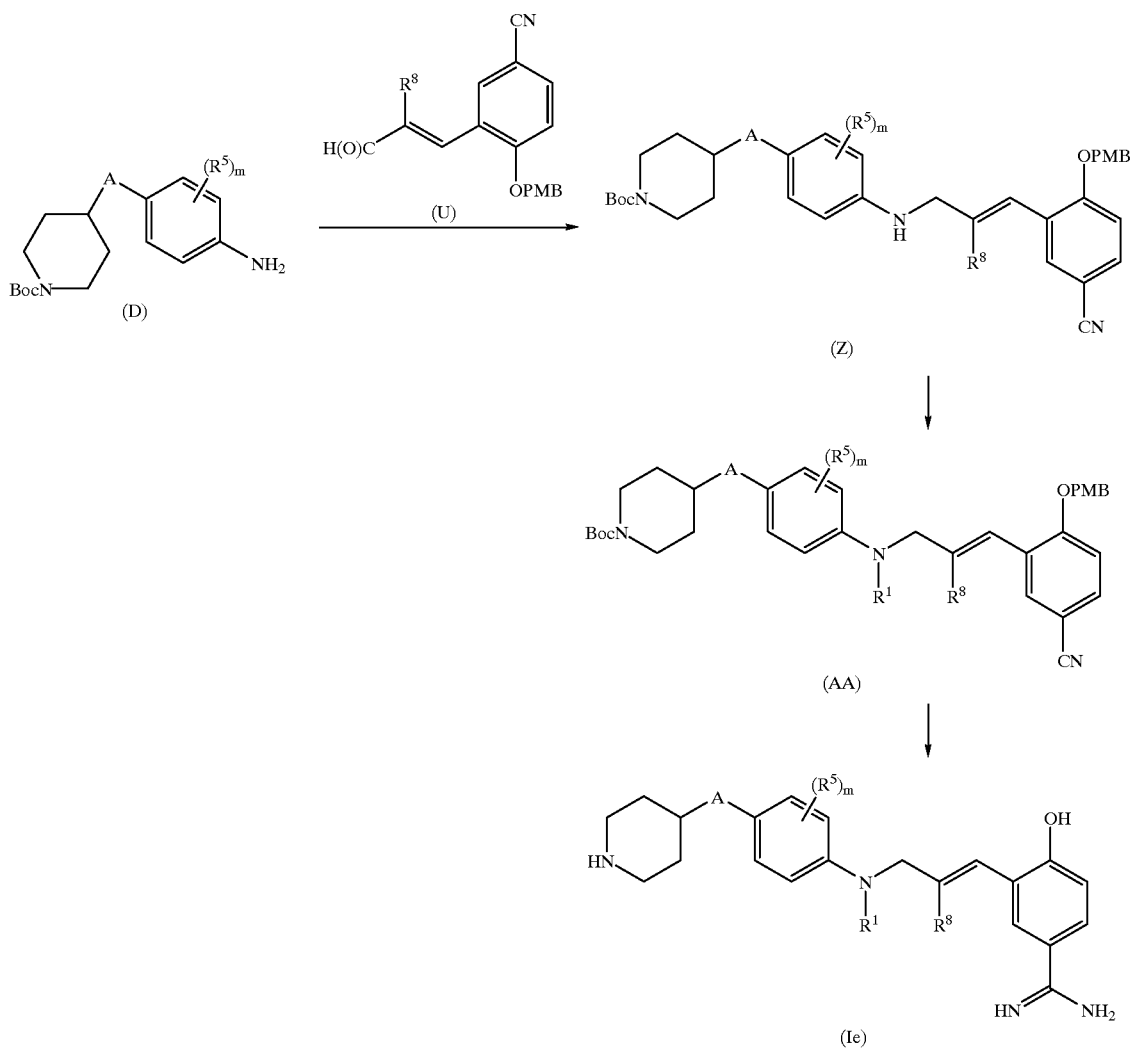

Compounds of formula (D) and (U) may be prepared by methods disclosed herein or by methods known to those skilled in the art.

In general, compounds of formula (Ie) are prepared by first reacting a compound of formula (D) under reductive amination conditions to form a compound of formula (Z). For example, to a mixture of a compound of formula (D) and formula (Z) in a polar solvent, for example, methanol, is added a mild acid, such as acetic acid. The reaction mixture is stirred at ambient temperature for 15 minutes to 1 hour, preferably for 1 hour and then a reducing agent, such as NaCNBH$_3$, is added and the reaction mixture is stirred at ambient temperature for 30 minutes to 1 hour, preferably for 1 hour. The reaction mixture is concentrated and the residue is taken up in a mild base, such as NaHCO$_3$. The compound of formula (Z) is isolated from the reaction mixture by standard isolation techniques, such as extraction, concentration and purification by flash chromatography.

The compound of formula (Z) in an aprotic solvent, such as methylene chloride, is treated with an acylating agent, such as 4-chloro-4-oxobutyrate, in the presence of a base, such as pyridine, at 0° C. The resulting solution is warmed to ambient temperature for 30 minutes to 1 hour, preferably for about 30 minutes. The compound of formula (AA) is then isolated from the reaction mixture.

The compound of formula (AA) is dissolved in an anhydrous alkanol, preferably ethanol, and then anhydrous mineral acid, preferably HCl, is added to the solution over a period of time sufficient to saturate the acid into the solution while maintaining the reaction temperatures at about −78° C. After saturation is complete, the reaction vessel is sealed and the reaction mixture is allowed to warm to ambient temperature and stirred between 12 and 24 hours, preferably for about 16 hours. The solvent is removed in vacuo and the resulting residue is dissolved in fresh anhydrous alkanol, preferably ethanol, and then treated with anhydrous ammonia (gas) at temperatures from between ambient temperature and about 100° C. from about 1 to about 48 hours, preferably at about 60° C. and for about 2 hours. The compound of formula (Ie) is then isolated from the reaction mixture by standard isolation techniques, for example, in vacuo removal of solvent and purification by high performance liquid chromatography (HPLC). During this last step, compounds of formula (AA) any protected oxygen or nitrogen substituent is de-protected.

Alternatively, compounds of formula (D) can be reacted with compounds of formula (Q) under standard alkylating conditions to form corresponding analogs of compounds of formula (Z), which can then be reacted in a similar manner as described above for compounds of formula (Z) and formula (AA) to form compounds of the invention.

Alternatively, compounds of formula (D) can be reacted with compounds of formula (H) under standard alkylating conditions to form corresponding analogs of compounds of formula (Z), which can then be reacted in a similar manner as described above for compounds of formula (Z) and formula (AA) to form compounds of the invention.

Alternatively, compounds of formula (I) wherein $R^2$ is —[C($R^7$)$_2$]$_m$—[C($R^8$)]=CH— (as illustrated above by the compounds of formula (Ie)), can be treated under hydrogenation conditions (e.g., Pd/C) to make compounds of formula (I) wherein $R^2$ is —[C($R^7$)$_2$]$_m$— (saturated).

In the following Reaction Scheme 8 depicting the preparation of compounds of formula (If), which are compounds of the invention, A is —O— or —N($R^7$)—; m is 0 to 4 and each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; $R^7$ is hydrogen, alkyl, aryl, or aralkyl; and $R^8$ is hydrogen, alkyl, aryl, or aralkyl.

REACTION SCHEME 8

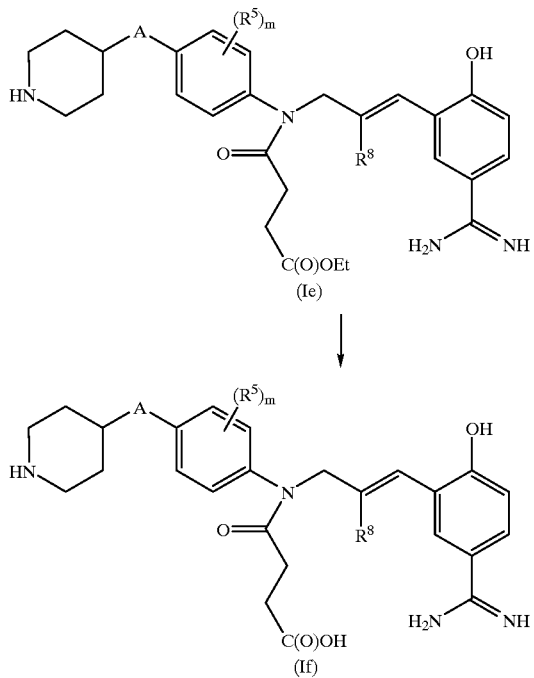

Compounds of formula (Ie) are prepared according to methods disclosed.

In general, compounds of formula (If) are prepared by treating compounds of formula (Ie) under basic hydrolysis conditions, such as adding LiOH to a solution of a compound of formula (Ie) in a polar solvent, such as ethanol/water, and then stirring the reaction mixture at ambient temperature to about 100° C., preferably at ambient temperature, for 2 to 4 hours, preferably for about 4 hours. The compound of formula (If) is isolated from the reaction mixture by standard isolation techniques, such as neutralization of the mixture by the addition of an acid, concentration and separation by HPLC.

In the following Reaction Scheme 9 depicting the preparation of compounds of formula (Ig), which are compounds of the invention, A is —O— or —N($R^7$)—; $R^1$ is alkyl, alkylcarbonyl, phenylalylidenyl (wherein the phenyl group is optionally substituted by alkyl, halo, alkoxy, aralkoxy, —C(NH)—NH$_2$, —C(NH)N(H)O$R^7$, —C(NH)N(H)C(O)O$R^9$, —C(NH)N(H)C(O)$R^9$, —C(NH)N(H)S(O)$_2$$R^9$, or —C(NH)N(H)C(O)N(H)$R^7$), alkoxycarbonylalkyl, carboxyalkyl, aminocarbonylalkyl, monoalkylaminocarbonylalkyl, dialkylaminocarbonylalkyl, alkoxycarbonyl, phenylcarbonyl (wherein the phenyl group is optionally substituted by carboxy or alkoxycarbonyl), carboxyalkylcarbonyl, alkoxycarbonylalkylcarbonyl, aminocarbonylalkylcarbonyl, benzyl (wherein the phenyl group is optionally substituted by alkyl, halo, alkoxy, aralkoxy, —C(NH)—NH$_2$, —C(NH)N(H)O$R^7$, —C(NH)N(H)C(O)O$R^9$, —C(NH)N(H)C(O)$R^9$, —C(NH)N(H)S(O)$_2$$R^9$, or —C(NH)N(H)C(O)N(H)$R^7$), mono[dialkoxycarbonyl]alkylaminocarbonyl, mono[dicarboxy]alkylaminocarbonyl, alkylsulfonyl, arylsulfonyl or dialkylaminosulfonyl; m is 0 to 4 and each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; each $R^7$ is hydrogen, alkyl, aryl, or aralkyl; $R^8$ is hydrogen, alkyl, aryl or aralkyl, and each $R^9$ is alkyl or aralkyl:

REACTION SCHEME 9

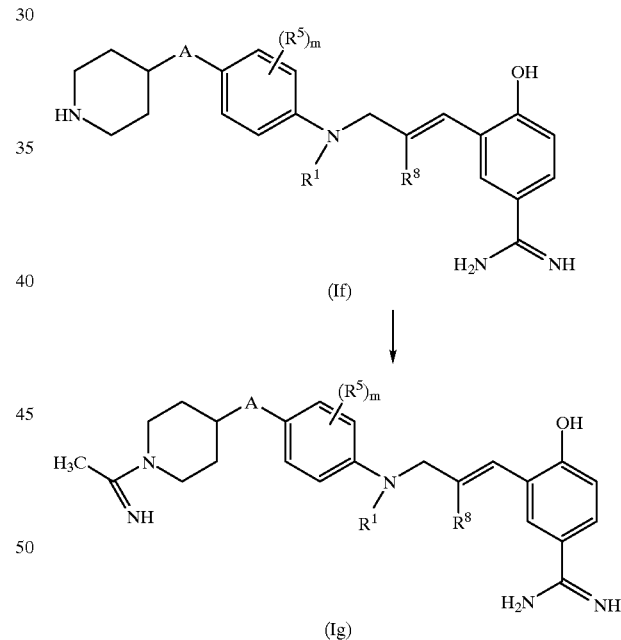

Compounds of formula (If) are prepared according to methods disclosed herein.

In general, compounds of formula (Ig) are prepared from compounds of formula (If) by first treating a compound of formula (If) with ethyl acetimidate in a polar solvent, such as ethanol, in the presence of a base, such as triethylamine. The reaction mixture is stirred at ambient temperature for 2 to 4 hours, preferably for about 4 hours. The mixture is then acidified and concentrated, and the compound of formula (Ig) is isolated from the concentrate by HPLC.

In the following Reaction Scheme 10 depicting the preparation of compounds of formula (Ib), which are compounds of the invention, A is —O— or —N(R⁷)—; R¹ is alkyl, alkylcarbonyl, phenylalylidenyl (wherein the phenyl group is optionally substituted by alkyl, halo, alkoxy, aralkoxy, —C(NH)—NH₂, —C(NH)N(H)OR⁷, —C(NH)N(H)C(O)OR⁹, —C(NH)N(H)C(O)R⁹, —C(NH)N(H)S(O)₂R⁹, or —C(NH)N(H)C(O)N(H)R⁷), alkoxycarbonylalkyl, carboxyalkyl, aminocarbonylalkyl, monoalkylaminocarbonylalkyl, dialkylaminocarbonylalkyl, alkoxycarbonyl, phenylcarbonyl (wherein the phenyl group is optionally substituted by carboxy or alkoxycarbonyl), carboxyalkylcarbonyl, alkoxycarbonylalkylcarbonyl, aminocarbonylalkylcarbonyl, benzyl (wherein the phenyl group is optionally substituted by alkyl, halo, alkoxy, aralkoxy, —C(NH)—NH₂, —C(NH)N(H)OR⁷, —C(NH)N(H)C(O)OR⁹, —C(NH)N(H)C(O)R⁹, —C(NH)N(H)S(O)₂R⁹, or —C(NH)N(H)C(O)N(H)R⁷), mono[dialkoxycarbonyl]alkylaminocarbonyl, mono[dicarboxy]alkylaminocarbonyl, alkylsulfonyl, arylsulfonyl or dialkylaminosulfonyl; m is 0 to 4 and each R⁵ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; each R⁷ is hydrogen, alkyl, aryl, or aralkyl; each R⁸ is hydrogen, alkyl, aryl, or aralkyl, and each R⁹ is alkyl or aralkyl:

REACTION SCHEME 10

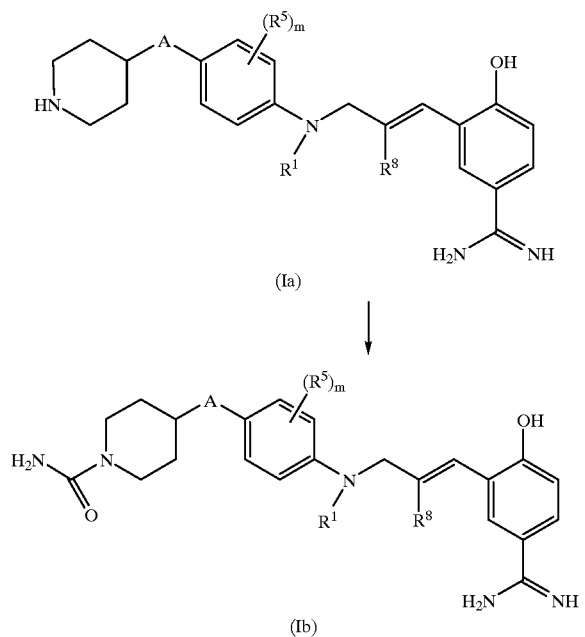

Compounds of formula (Ia) are prepared by methods disclosed herein.

In general, compounds of formula (Ib) are prepared by first treating a compound of formula (Ia) in a polar solvent, such as methanol, with the optionally nitrogen substituted phenyl carbamate in the presence of a base, such as triethylamine. The reaction mixture is stirred at ambient temperature for about 2 to 4 hours, preferably for about 3 hours, acidified with a mild acid and purified on HPLC to afford a compound of formula (Ib).

In the following Reaction Scheme 11 depicting the preparation of compounds of formula (Id), which are compounds of the invention, A is —O— or —N(R⁷)—; R¹ is alkyl, alkylcarbonyl, phenylalylidenyl (wherein the phenyl group is optionally substituted by alkyl, halo, alkoxy, aralkoxy, —C(NH)—NH₂, —C(NH)N(H)OR⁷, —C(NH)N(H)C(O)OR⁹, —C(NH)N(H)C(O)R⁹, —C(NH)N(H)S(O)₂R⁹, or —C(NH)N(H)C(O)N(H)R⁷), alkoxycarbonylalkyl, carboxyalkyl, aminocarbonylalkyl, monoalkylaminocarbonylalkyl, dialkylaminocarbonylalkyl, alkoxycarbonyl, phenylcarbonyl (wherein the phenyl group is optionally substituted by carboxy or alkoxycarbonyl), carboxyalkylcarbonyl, alkoxycarbonylalkylcarbonyl, aminocarbonylalkylcarbonyl, benzyl (wherein the phenyl group is optionally substituted by alkyl, halo, alkoxy, aralkoxy, —C(NH)—NH₂, —C(NH)N(H)OR⁷, —C(NH)N(H)C(O)OR⁹, —C(NH)N(H)C(O)R⁹, —C(NH)N(H)S(O)₂R⁹, or —C(NH)N(H)C(O)N(H)R⁷), mono[dialkoxycarbonyl]alkylaminocarbonyl, mono[dicarboxy]alkylaminocarbonyl, alkylsulfonyl, arylsulfonyl or dialkylaminosulfonyl; m is 0 to 4 and each R⁵ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; each R⁷ is hydrogen, alkyl, aryl, or aralkyl; R⁸ is hydrogen, alkyl, aryl or aralkyl; and each R⁹ is alkyl or aralkyl:

REACTION SCHEME 11

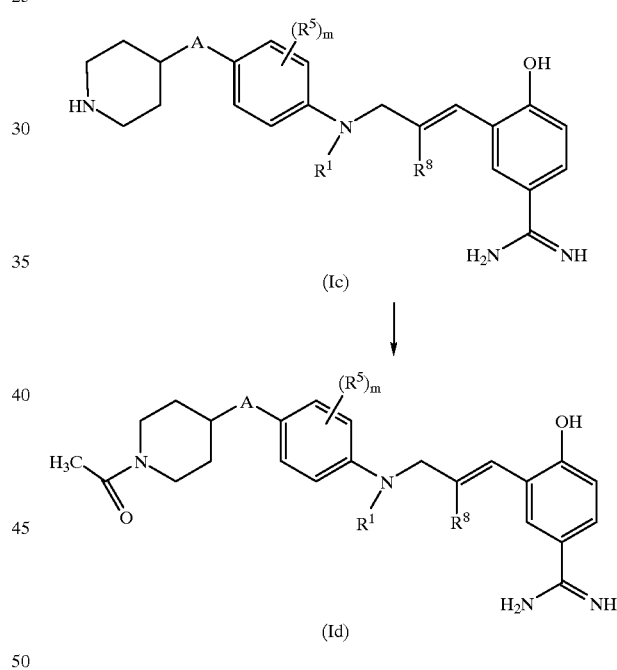

Compounds of formula (Ic) are prepared by methods disclosed herein.

In general, compounds of formula (Id) are prepared by treating a compound of formula (Ic) in an aprotic solvent, such as acetonitrile, with an acylating agent, such as acetyl chloride, at ambient temperature. The resulting mixture is stirred at ambient temperature for about 1 hour to about 4 hours, preferably for 2 hours. A base, such as LiOH in water, is added to the reaction mixture and the mixture is stirred at ambient temperature for 1 to 3 hours, preferably for 2 hours. The reaction mixture is neutralized by addition of an acid, concentrated and purified by HPLC to afford the compound of formula (Id).

In Reaction Scheme 12, which depicts the preparation compounds of formula (EE), which are intermediates in the preparation of the compounds of the invention, each R⁷ is independently hydrogen, alkyl, aryl or aralkyl:

REACTION SCHEME 12

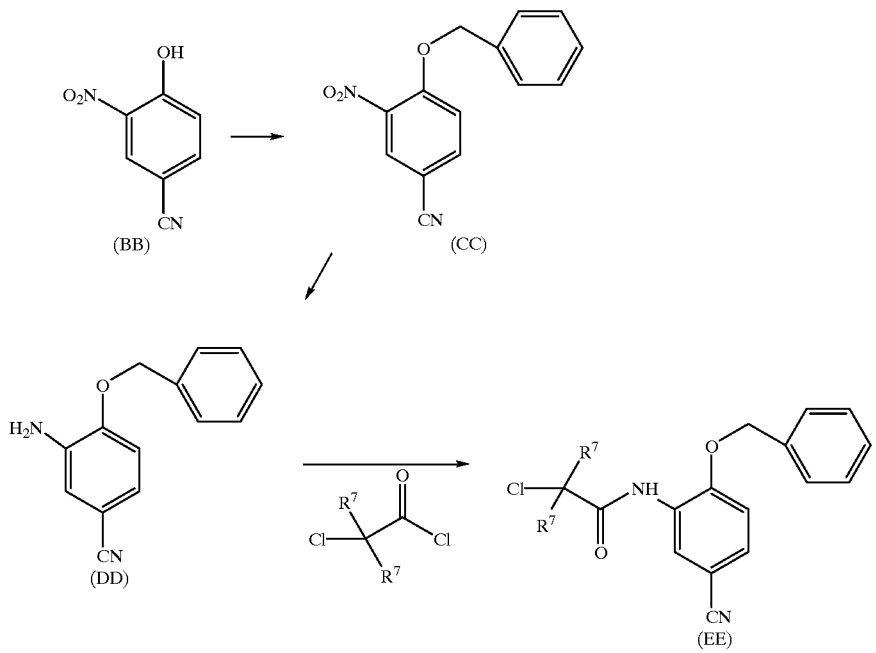

Compounds of formula (BB) are commercially available or may be prepared according to methods known to those skilled in the art.

In general, compounds of formula (EE) are prepared by first treating a compound of formula (BB) in an aprotic solvent, such as a mixture of dimethylformamide and acetonitrile, with a protecting group providing agent, such as benzyl bromide, in the presence of a base, such as potassium carbonate. The reaction mixture is heated at temperatures between ambient temperatures and 100° C., preferably at about 60° C., for about 3 to 6 hours, preferably for about 4 hours. The compound of formula (CC) is isolated from the reaction mixture by standard isolation techniques, such as extraction, concentration and recrystallization.

The compound of formula (CC) is then treated with a reducing agent, such as tin chloride, under standard reducing conditions to form a compound of formula (DD).

The compound of formula (DD) is then treated with an acylating agent, such as choroacetylchloride, in the presence of an anhydrous base in a polar solvent, such as acetone under a nitrogen atmosphere, to afford a compound of formula (EE).

In the following Reaction Scheme 13, depicting the preparation of compounds of formula (HH), which are intermediates in the preparation of compounds of the invention, A is —O— or —N($R^7$)—; m is 0 to 4 and each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; and Boc is t-butoxycarbonyl.

REACTION SCHEME 13

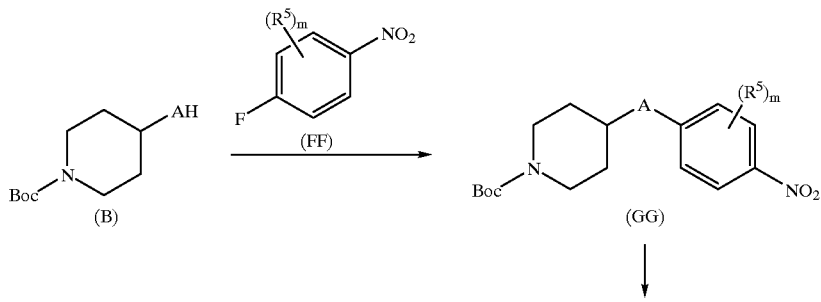

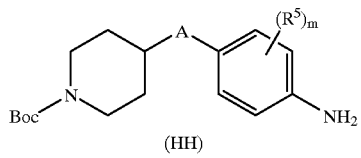

(HH)

Compounds of formula (B) and formula (FF) are commercially available or may be prepared according to methods known to those skilled in the art.

In general, the compounds of formula (HH) are prepared in a similar manner as the compounds of formula (D) described above.

In the following Reaction Scheme 14 depicting the preparation of compounds of formula (Ih), which are compounds of the invention, A is —O— or —N($R^7$)—; m is 0 to 4; each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; Boc is t-butoxycarbonyl; and each $R^7$ is independently hydrogen, alkyl, aryl or aralkyl:

REACTION SCHEME 14

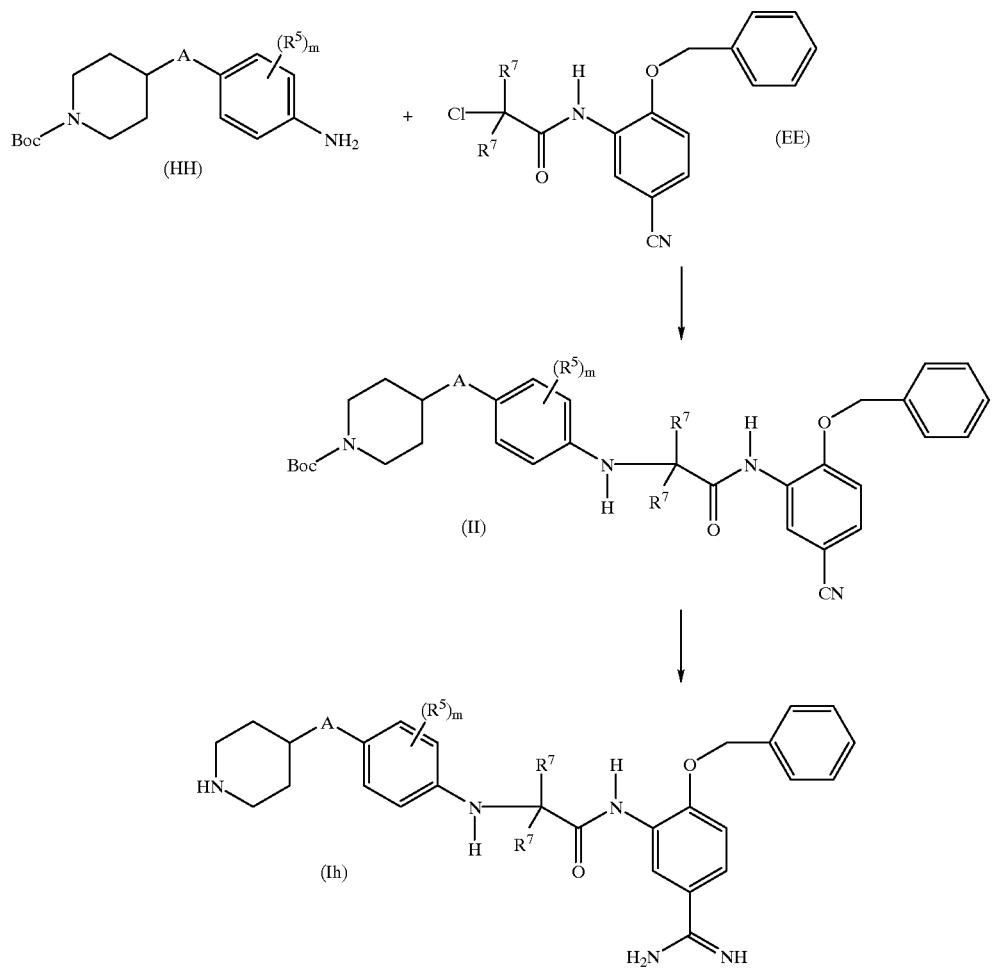

Compounds of formula (EE) and formula (HH) may be prepared according to methods disclosed herein or may be prepared according to methods known to those skilled in the art.

In general, compounds of formula (Ih) are prepared by first treating a compound of formula (HH) in an aprotic solvent, such as dimethyl formamide, and in the presence of a base, such as potassium carbonate, and sodium iodide with a compound of formula (EE). The reaction mixture is heated to about 80° C. for 4 to 6 hours, preferably for about 5.5 hours. The mixture is allowed to cool and then poured onto ice water. The compound of formula (II) was isolated from the resulting slurry by standard isolation techniques, such as extraction, concentration and purification by flash chromatography.

The compound of formula (II) so formed is then treated under similar conditions as the compound of formula (AA) to form the corresponding compound of formula (Ih).

In the following Reaction Scheme 15 depicting the preparation of compounds of formula (Ii), which are compounds of the invention, X is O or NH; A is —O— or —N($R^7$)—; m is 0 to 4; each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; and each $R^7$ is hydrogen, alkyl, aryl or aralkyl:

REACTION SCHEME 15

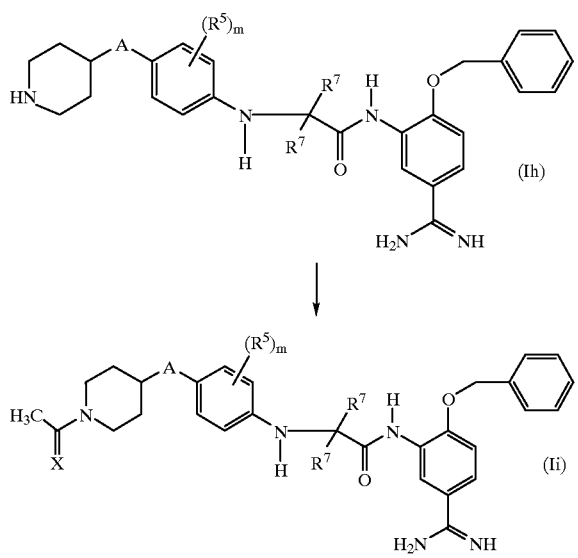

Compounds of formula (Ih) are prepared by methods disclosed herein.

In general, the compounds of formula (Ii) are prepared by similar methods as those described above for compounds of formula (Ig).

In the following Reaction Scheme 16, depicting the preparation of compounds of formula (Ij), which are compounds of the invention, X is O or NH; A is —O— or —N($R^7$)—; m is 0 to 4; each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl; and each $R^7$ is hydrogen, alkyl, aryl or aralkyl:

REACTION SCHEME 16

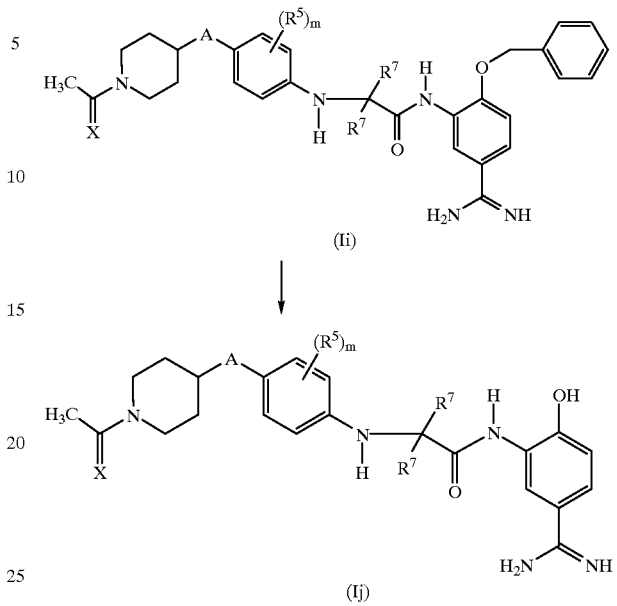

Compounds of formula (Ii) are prepared by methods disclosed herein.

In general, compounds of formula (Ij) are prepared by standard hydrogenating conditions. Alternatively, instead of treating the above compounds of formula (AA) or formula (II) with anhydrous ammonia (gas), the compounds may be treated with a compound of the formula $NH_2OR^9$ to afford the corresponding compound of formula (I) wherein $R^3$ is —C(NH)N(H)O$R^9$.

Compounds of the invention containing an alkoxycarbonyl group may be prepared from the corresponding activated acid, such as an acid halide by techniques known to those of ordinary skill in the art.

Compounds of formula the invention containing an aminocarbonyl group, a monoalkylaminocarbonyl group, or a dialkylaminocarbonyl group may also be hydrolyzed under acidic conditions to prepare corresponding compounds of the invention containing a —C(O)OH group.

Compounds of the invention containing a carboxy group or an alkoxycarbonyl group may also be amidated under standard amidation conditions to form the corresponding compounds of the invention containing an aminocarbonyl group, a monoalkylaminocarbonyl group, or a dialkylaminocarbonyl group.

Compounds of the invention containing a nitro group may also be reduced under standard conditions to produce the corresponding compounds of the invention containing an amino group, which may also be treated with the appropriate alkylating agents or acylating agents to afford the corresponding compounds of the invention containing a monoalkylamino group or a dialkylamino group.

Compounds of the invention may also be further treated with the appropriate acid halide, preferably acid chloride, or with the appropriate acid anhydride or an equivalent, to yield compounds of the invention wherein $R^3$ is —C(NH)N(H)C(O)$R^7$ where $R^7$ is hydrogen, alkyl, aryl or aralkyl.

Alternatively, compounds of the invention may further be treated with a compound of formula Cl—C(O)—O$R^9$ or its functional equivalent to yield compounds of the invention where $R^3$ is —C(NH)N(H)C(O)O$R^9$.

Alternatively, compounds of the invention may also be further treated with compounds of the formula $R^9$—$S(O)_2$-imidazole (where $R^9$ is defined above in the Summary of the Invention) in a polar solvent, such as methylene chloride, at ambient temperature to afford compounds of the invention where $R^9$ is —$C(NH)N(H)S(O)_2R^9$ where $R^9$ is defined above in the Summary of the Invention.

Alternatively, compounds of formula the invention may be further treated with an appropriately N—$R^7$-substituted phenylcarbamate in a polar solvent, preferably methylene chloride, at ambient temperature, for about 6 to 24 hours, preferably for about 12 hours, to afford compounds of the invention where $R^3$ is —$C(NH)N(H)C(O)N(H)R^7$ where $R^7$ is defined above in the Summary of the Invention.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques.

The following specific preparations and examples are provided as a guide to assist in the practice of the invention, and are not intended as a limitation on the scope of the invention.

PREPARATION 1

Compounds of Formula (D)

A. To 4-hydroxy-N-(t-butoxycarbonyl)piperidine (10.0 g) in DMF was added NaH (2.2 g) at ambient temperature. The reaction mixture was stirred at ambient temperature for 2 hours. 4-Flouro-3-trifluoromethyl-1-nitrobenzene (5.3 mL) was added and the reaction mixture was stirred overnight at ambient temperature. The reaction mixture was diluted with water and extracted with ethyl acetate. The organic layer was washed with aqueous $NaHCO_3$ and aqueous HCl, dried over sodium sulfate, concentrated and purified on silica gel column (hexane/ethyl acetate, gradient) to afford a compound of formula (C), 4-(N-(t-butoxycarbonyl)piperidin-4-yl)oxy-3-trifluoromethyl-1-nitrobenzene in 80% yield.

B. In a similar manner, other compounds of formula (C) are prepared.

C. 4-(N-(t-butoxycarbonyl)piperidin-4-yl)oxy-3-trifluoromethyl-1-nitrobenzene was dissolved in methanol in the presence of Pd/C. The solution was hydrogenated at 50 psi for 1 hour until hydrogen intake was completed. The catalyst was filtered off and the filtrate was concentrated to afford 4-[(N-(t-butoxycarbonyl)piperidin-4-yl)oxy]-3-trifluoromethylbenzenamine, >95%.

D. In a similar manner, other compounds of formula (D) are prepared.

PREPARATION 2

Compounds of Formula (H)

A. A mixture of 3-bromobenzonitrile (910 mg), $Pd(Ph_3P)_4$ (290 mg), $(Me_3Sn)_2$ (1.64 g) and dioxane (20 mL) was sealed under argon in a pressure tube. The tube was then heated at 100–110° C. for 3 hours with stirring and another 15 hours at 80° C. To the reaction mixture was added 1-bromo-3-methylbenzene (940 mg), $Pd(PPh_3)_4$ (290 mg) and dioxane (5 mL) under argon. The sealed tube was heated at 135–140° C. with stirring for two days. The catalyst was filtered off and the filtrate was poured into water and extracted with ethyl acetate (3×). The organic layer was washed with brine, dried over $Mg_2SO_4$, concentrated and purified on silica gel column (ethyl acetate/hexane, 1:3) to afford 0.64 g of 3-(3-cyanophenyl)-1-methylbenzene.

B. In a similar manner, other compounds of formula (G) are prepared.

C. A mixture of 3-(3-cyanobenzene)-1-methylbenzene (0.73 g), NBS (0.712 g), and benzoylperoxide (92 mg) in $CCl_4$ was heated at reflux for 15 hours. After removal of the solvent the crude product was separated on silica gel column (ethylacetate/hexane=1:3) to afford 3-(3-cyanophenyl)-1-(bromomethyl)benzene (0.6 g).

D. In a similar manner, other compounds of formula (H) are prepared.

PREPARATION 3

Compounds of Formula (M)

A. To 4-hydroxy-N-methylpiperidine (13.0 g) in DMF was added NaH (4.2 g) at ambient temperature. The reaction mixture was stirred at ambient temperature for 3 hours. 4-fluoro-3-trifluoromethyl-1-nitrobenzene (22 g) was added at –10° C. and the reaction was stirred overnight at ambient temperature. The reaction was diluted with water and extracted with ethyl acetate. The organic layer was washed with brine, dried over sodium sulfate, concentrated and purified on silica gel column (hexane/ethyl acetate.

B. In a similar manner, other compounds of formula (L) are prepared.

C. 4-(N-methylpiperidin-4-yl)oxy-3-trifluoromethyl-1-nitrobenzene was dissolved in methanol in the presence of Pd/C. The solution was hydrogenated at 50 psi for 1 hour until hydrogen intake was completed. The catalyst was filtered off and the filtrate was concentrated to afford 4-(N-methylpiperidin-4-yl)oxy-3-trifluoromethylbenzenamine, >95%.

D. In a similar manner, other compounds of formula (M) are prepared.

PREPARATION 4

Compounds of formula (Q)

A. A mixture of 3-cyanobenzaldehyde (2.0 g) and (triphenylphosphoranylidene) acetaldehyde (5.0 g) in 100 mL $CH_2Cl_2$ was stirred at reflux for 16 hours. The reaction was cooled, concentrated and purified on silica gel column (ethyl acetate/hexane=3/7) to afford 2.2 g of 3-cyano-1-(2-formylethenyl)benzene as a yellow oil.

B. In a similar manner, other compounds of formula (O) are prepared.

C. To 3-cyano-1-(2-formylethenyl)benzene (1 g) in 30 mL of MeOH were added $CeCl_3$ (1.88 g) and the resulting solution was stirred for 30 minutes and cooled to 0° C. To the solution was then added $NaBH_4$ (0.29 g). The resulting solution was stirred for 1 hour at 0° C. and concentrated. The residue was taken up in 100 mL of saturated aqueous $NaHCO_3$ and extracted with ethyl acetate (3×). The organic layer was dried, concentrated and purified on silica gel column (ethyl acetate/hexane, 1:4) to give 0.73 g of 3-cyano-1-(3-hydroxyprop-2-en-1 yl)benzene.

D. In a similar manner, other compounds of formula (P) are prepared.

E. To a suspension of $Ph_3P$ (1.0 g) in 40 mL of MeCN at 0° C. was added bromine (0.6 g) and the mixture was stirred at 0° C. for 15 minutes and then warmed to ambient temperature. To the suspension of $Br_2PPh_3$ was then added 3-cyano-1-(3-hydroxyprop-2-en-1yl)benzene (0.5 g) in 10 mL MeCN dropwise. The resulting solution was stirred at 60° C. for 30 minutes, cooled to ambient temperature and concentrated. The residue was triturated with 10% hexane in ethyl acetate. The mixture was filtered through a silica gel pad and the filtrate was concentrated to afford 0.71 g of 3-cyano-1-(3-bromoprop-2-en-1yl)benzene as a yellow oil.

F. In a similar manner, other compounds of formula (Q) are prepared.

PREPARATION 5

Compounds of Formula (W)

A. To 3-bromo-6-hydroybenzaldehyde (5 g) in 100 mL $CH_2Cl_2$ was added NaH (1.0 g) and it was then stirred for 30 minutes at ambient temperature. 4-methoxybenzyl chloride (4.29 g) was added to the above solution and stirring was continued for 16 hours at ambient temperature. The reaction was diluted with 100 mL of water and the aqueous layer was extracted with ethyl acetate (3×). The organic layer was dried, concentrated and purified on silica gel column (ethyl acetate/hexane, 3:7) to afford 3-bromo-6-((4-methoxybenzyl)oxy)benzaldehyde (6.7 g) as a white solid.

B. A mixture of 3-bromo-6-((4-methoxybenzyl)oxy) benzaldehyde (4 g), $Zn(CN)_2$ (1 g) and $Pd(PPh_3)_4$ (4.32 g) in 40 mL DMF was stirred at 90° C. for 3 hours, cooled to ambient temperature and diluted with 100 mL 50% $NH_4OH$. The aqueous layer was extracted with ethyl acetate (3×). The organic layer was dried, concentrated and purified on silica gel column (ethyl acetate/hexane, 1:4) to afford 2.8 g of 3-cyano-6-((4-methoxybenzyl)oxy)benzaldehyde as a yellow solid.

C. A mixture of 3-cyano-6-((4-methoxybenzyl)oxy) benzaldehyde (2.8 g) and (triphenylphosphoranylidene) acetaldehyde (3.5 g) in 40 mL $CH_2Cl_2$ was stirred at reflux for 16 hours. The solution was cooled to ambient temperature, concentrated and purified on silica gel column (ethyl acetate/hexane/$CH_2Cl_2$, 1:8:3) to give 3-cyano-6-((4-methoxybenzyl)oxy)-1-(2-formylethenyl)benzene (2.8 g) as a yellow solid.

D. To 3-cyano-6-((4-methoxybenzyl)oxy)-1-(2-formylethenyl)benzene (2.30 g) in 100 mL solution of $CH_2Cl_2/MeOH/H_2O$ (2:7:1) was added $NaBH_4$ (0.29 g) at 0° C. The resulting solution was stirred at 0° C. for 1 hour and concentrated. The resulting residue was diluted with 100 mL of saturated aqueous $NaHCO_3$ and extracted with ethyl acetate (3×). The organic layer was dried, concentrated to afford 3-cyano-6-((4-methoxybenzyl)oxy)-1-(3-hydroxyprop-2-en-1-yl)benzene (92.3 g) as a yellow solid.

E. To a suspension of $Ph_3P$ (2.4 g) in 30 mL of MeCN at 0° C. was added bromine (1.5 g) and the mixture was stirred at 0° C. for 15 minutes and then warmed to ambient temperature. To the suspension of $Br_2PPh_3$ was then added 3-cyano-6-((4-methoxybenzyl)oxy)-1-(3-hydroxyprop-2-en-1-yl)benzene (2.3 g) in 20 mL MeCN drop-wise. The resulting solution was stirred at ambient temperature for 1 hour, cooled to ambient temperature and concentrated. The residue was purified on silica gel column (ethyl acetate/hexane, 1:9) to afford 3-cyano-6-((4-methoxybenzyl)oxy)-1-(3-bromoprop-2-en-1-yl)benzene (0.81 g) as a yellow oil.

PREPARATION 6

Compounds of Formula (Y)

A. To 4-(N'-(t-butoxycarbonyl)piperidin-4-yl)oxy-3-nitro-N-(3-(3-cyanophenyl)prop-2-en-1-yl)benzenamine (0.39 g) and $K_2CO_3$ (0.56 g) in DMF was added methyl bromoacetate. The mixture was stirred at 55° C. for 6 hours. The reaction was cooled, diluted with water and extracted with ethyl acetate (3×). The organic layer was concentrated and purified on silica gel column to afford 4-(N'-(t-butoxycarbonyl)piperidin-4-yl)oxy-3-nitro-N-(methoxycarbonylmethyl)-N-(3-(3-cyanophenyl)prop-2-en-1-yl)benzenamine (0.15 g).

B. In a similar manner, other compounds of formula (Y) are prepared.

PREPARATION 6a

Compounds of Formula (Yd)

A. To 4-hydroxy-3-nitrobenzenamine (10.0 g) in methylene chloride (60 mL) was added triethylamine (27 mL) and trifluoroacetic anhydride (10.9 mL) at 0° C. The reaction was stirred at 0° C. for three hours. The reaction was diluted with water, acidified and extracted with ethyl acetate. The organic layer was dried, concentrated and purified on silica gel column (ethyl acetate/hexane, 1:1) to afford 4-hydroxy-3-nitro-N-(trifluoromethylcarbonyl)benzenamine (10.0 g).

B. In a similar manner, other compounds of formula (Yb) are prepared.

C. To 4-hydroxy-3-nitro-N-(trifluoromethylcarbonyl) benzenamine (10.0 g), triphenylphosphine (22.1 g) and 4-hydroxy-N-(t-butoxycarbonyl)piperidine (17.0 g) in THF (30 mL) was added DEAD (13.5 mL) drop-wise. The reaction was stirred at ambient temperature for 1 hour, concentrated and purified on silica gel column (ethyl acetate/hexane, gradient) to afford 4-(N'-(t-butoxycarbonyl) piperidin-4-yl)oxy- 3-nitro-N-(trifluoromethylcarbonyl) benzenamine.

D. In a similar manner, other compounds of formula (Yc) are prepared.

E. To 4-(N'-(t-butoxycarbonyl)piperidin-4-yl)oxy-3-nitro-N-(trifluoromethylcarbonyl)benzenamine in methanol (150 mL) and water (150 mL) was added $K_2CO_3$ (6.0 g) and the reaction was heated to 50° C. for overnight. The reaction was extracted with ethyl acetate. The extract was dried, concentrated and purified on silica gel column (ethyl acetate/ hexane) to afford 4-(N'-(t-butoxycarbonyl)piperidin-4-yl) oxy-3-nitrobenzenamine (11.0 g).

F. In a similar manner, other compounds of formula (Yd) are prepared.

PREPARATION 6b

Compounds of Formula (Yf)

A. To 4-hydroxy-2-(methoxycarbonyl)benzenamine (6.8 g), triphenylphosphine (14.2 g) and 4-hydroxy-N-(t-butoxycarbonyl)piperidine (9.06 g) in THF (200 mL) was added DEAD (9.51 g) drop-wise at ambient temperature. The reaction was stirred at ambient temperature for overnight, concentrated and re-dissolved in ether. The ether layer was washed with 0.5 N NaOH aqueous solution, water and brine. It was then concentrated and purified on silica gel column (ethyl acetate/hexane, gradient) to afford 4-(N'-(t-butoxycarbonyl)piperidin-4-yl)oxy-2-(methoxycarbonyl) benzenamine (7.31 g).

B. In a similar manner, other compounds of formula (Yf) are prepared.

PREPARATION 7

Compounds of Formula (EE)

A. A solution of 3-nitro-4-hydroxybenzonitrile (10 g, 61 mmol) in a mixture of 40 mL of dimethylformamide and 100 mL of acetonitrile was stirred as anhydrous potassium carbonate (10.1 g, 73.2 mmol) and benzyl bromide (10.4 g, 61 mmol) were added. The reaction was heated at 60° C. for about 4 h. The reaction was filtered and the solid was washed with ethyl acetate. The filtrate was washed with water. The organic layers were washed with water and brine, dried and concentrated. The solid was recrystallized from acetone/hexane to give 14 g (90%) of 3-nitro-4-(benzyloxy)benzonitrile, as a white solid.

B. A solution of 3-nitro-4-(benzyloxy)benzonitrile (14 g, 55 mmol) in 300 mL of ethyl acetate was stirred as tin chloride (61 g, 270 mmol) was added. The reaction was heated at reflux for a total of 5 hours. The reaction was allowed to cool and poured into ice water containing 68 g of potassium bicarbonate. The reaction was filtered through celite. The aqueous layer was washed with ethyl acetate (2×). The combined organic layers were washed with water (2×) and brine, dried and concentrated to give 12.5 g of a product. Purification of the product by flash chromatography on silica gel using a step gradient of 20, 40, and 50% ethyl acetate in hexane gave 7.3 g of 3-amino4-(benzyloxy)benzonitrile; NMR (CDCl$_3$, TMS) δ5.16 (s, 2), 6.84 (d, 1), 6.91 (s, 1), 7.04 (d, 1), 7.43 (m, 5) ppm.

C. A slurry of 3-amino-4-(benzyloxy)benzonitrile (7 g, 31.2 mmol) and anhydrous potassium carbonate (8.6 g, 62.4 mmol) in 50 mL of acetone was stirred under nitrogen as chloroacetylchloride (2.6 mL, 33 mmol) was added portionwise. The reaction was stirred overnight. The reaction was poured into ice water and the liquid was neutralized with 6 N hydrochloric acid. The resulting solid was isolated by filtration, washed with water, and dried under reduced pressure to give 3-((chloromethyl)carbonylamino)-4-(benzyloxy)benzonitrile (8.3 g) as a white solid; NMR (CDCl$_3$, TMS) δ4.22 (s, 2), 5.23 (s, 2), 7.03 (d, 1), 7.43 (m, 7), 8.73 (d, 1).

PREPARATION 8

Compounds of Formula (HH)

A. A slurry of hexane-washed sodium hydride (3 g, 75 mmol) in dimethyl formamide (80 mL) was stirred as a solution of N-(t-butoxycarbonyl)4-hydroxypiperidine (10 g, 50 mmol) in dimethyl formamide (10 mL) was added dropwise. Slight heating was used to initiate reaction, but the reaction needed to be cooled in an ice bath to control the reaction rate. Approximately 30 min after the addition was complete, solid 4-fluoro-1-nitrobenzene (7.4 g, 52 mmol) was added at once. The reaction was stirred for about 3 hours. The reaction was poured into ice water. The pH of the resulting liquid was adjusted to neutrality with 1 N hydrochloric acid. The resulting solid was isolated by filtration, washed with water, and dried under reduced pressure to give 16 g of 4-(N-(t-butoxycarbonyl)piperidin-4-yl)oxy-1-nitrobenzene, NMR (CDCl$_3$, TMS) δ1.45 (s, 9), 1.72 (m, 2), 1.98 (m, 2), 3.38 (m, 2), 3.68 (m, 2), 4.62 (m, 1), 6.98 (m, 2), 8.19 (m, 2).

B. In a similar manner, other compounds of formula (GG) are prepared.

C. A slurry of 4-(N-(t-butoxycarbonyl)piperidin-4-yl)oxy-1-nitrobenzene (15.1 g, 46.8 mmol) in absolute ethanol (500 mL) and methanol (200 mL) was purged with nitrogen, treated with 10% palladium on carbon (1.2 g, 50% water by wt.) and placed on a Parr Hydrogenator under 43 psi of hydrogen gas. The catalyst was removed by filtration. Solvent removal under reduced pressure gave a solid after drying. Purification by flash silica gel chromatography using a step gradient of 50 to 85% ethyl acetate in hexane gave 11.7 g of 4-(N-(t-butoxycarbonyl)piperidin-4-yl)oxybenzenamine, NMR (CDCl$_3$, TMS) δ1.45 (s, 9), 1.7 (m, 2), 1.86 (m, 2), 3.25 (m, 2), 3.68 (m, 2), 4.25 (m, 1), 6.63 (m, 2), 6.76 (m, 2).

D. In a similar manner, other compounds of formula (HH) are prepared.

EXAMPLE 1

Compounds of Formula (Ie)

A. To a mixture of 4-[(N-(t-butoxycarbonyl)piperidin-4-yl)oxy]-3-trifluoromethylbenzenamine (4.9 g) and 3-cyano-6-((4-methoxybenzyl)oxy)-1-(2-formylethenyl)benzene (4 g) in MeOH (80 mL) was added acetic acid (0.73 g). The resulting solution was stirred at ambient temperature for 15 minutes and then NaCNBH$_3$ was added. The resulting solution was stirred at ambient temperature for 1 hour and concentrated. The residue was taken up in 100 mL of aqueous NaHCO$_3$ and extracted with ethyl acetate (3×). The organic layer was dried, concentrated and purified on silica gel column (ethyl acetate/hexane, 3:7) to afford 5.7 g of 4-(N(t-butoxycarbonyl)piperidin-4-yl)oxy-3-trifluoromethyl-N-(3-(6-((4-methoxybenzyl)oxy)-3-cyanophenyl)prop-2-en-1-yl)benzenamine as a yellow oil.

B. In a similar manner, other compounds of formula (Z) are prepared.

C. To 4-(N'-(t-butoxycarbonyl)piperidin-4-yl)oxy-3-trifluoromethyl-N-(3-(6-((4-methoxybenzyl)oxy)-3-cyanophenyl)prop-2-en-1-yl)benzenamine (1.39 g) in 20 mL of CH$_2$Cl$_2$ was added ethyl 4-chloro-4-oxobutyrate (0.43 g) and pyridine (1 mL) at 0° C. The resulting solution was allowed to warm to ambient temperature for 30 minutes and then diluted with 100 mL CH$_2$Cl$_2$. The organic layer was washed with saturated copper sulfate, dried and concentrated to afford 4-(N'-(t-butoxycarbonyl)piperidin-4-yl)oxy-3-trifluoromethyl-N-(2-(ethoxycarbonyl)ethylcarbonyl)-N-(3-(6-((4-methoxybenzyl)oxy)-3-cyanophenyi)prop-2-en-1-yl)benzenamine as a blue solid.

D. In a similar manner, other compounds of formula (AA) are prepared.

E. To 4-(N'-(t-butoxycarbonyl)piperidin-4-yl)oxy-3-trifluoromethyl-N-(2-(ethoxycarbonyl)ethylcarbonyl)-N-(3-(6-((4-methoxybenzyl)oxy)-3-cyanophenyl)prop-2-en-1-yl)benzenamine (5.2 g) in 80 mL of ethanol was bubbled in HCl gas at −78° C. until the solution was saturated. The solution was allowed to warm to ambient temperature and stirred for 16 hours. The solvent was removed under reduced pressure and the residue was taken up in 80 mL of ethanol. Ammonia gas was bubbled into the solution for 4 minutes at −78° C. The resulting solution was stirred at 60° C. for 1.5 hours and concentrated. The resulting residue was separated on HPLC (MeCN/H$_2$O, gradient) to afford 4-(piperidin-4-yl)oxy-3-trifluoromethyl-N-(2-(ethoxycarbonyl)ethylcarbonyl)-N-(3-(6-(hydroxy)-3-amidinophenyl)prop-2-en-1-yl)benzenamine after concentration.

F. In a similar manner, other compounds of formula (Ie) are prepared.

EXAMPLE 2

Compounds of Formula (If)

A. To 4-(piperidin-4-yl)oxy-3-trifluoromethyl-N-(2-(ethoxycarbonyl)ethylcarbonyl)-N-(3-(6-(hydroxy)-3-amidinophenyl)prop-2-en-1-yl)benzenamine (2.0 g) in 100 mL ethanol/H₂O (50/50) was added LiOH (0.56 g) at ambient temperature and the resulting solution was stirred at ambient temperature for 4 hours. The reaction was acidified with trifluoroacetic acid, concentrated, separated on HPLC (CH₃CN/H₂O, gradient) and freeze-dried to afford 4-(piperdin-4-yl)oxy-3-trifluoromethyl-N-(2-(carboxy) ethylcarbonyl)-N-(3-(6-(hydroxy)-3-amidinophenyl)prop-2-en-1-yl)benzenamine.

B. In a similar manner, other compounds of formula (If) are prepared.

EXAMPLE 3

Compounds of Formula (Ig)

A. To 4-(piperidin-4-yl)oxy-3-trifluoromethyl-N-(2-(carboxy)ethylcarbonyl)-N-(3-(6-(hydroxy)-3-amidinophenyl)prop-2-en-1-yl)benzenamine (2.5 g) and ethyl acetimidate (2 g) in ethanol (100 mL) was added triethylamine and the solution was stirred at ambient temperature for 4 hours. The solution was acidified with trifluoroacetic acid, concentrated, separated on HPLC (CH₃CN/H₂O, gradient) and freeze-dried to afford 4-(N'-(1-iminoethyl)piperidin-4-yl)oxy-3-trifluoromethyl-N-(2-(carboxy)ethylcarbonyl)-N-(3-(6-(hydroxy)-3-amidinophenyl)prop-2-en-1-yl)benzenamine.

B. In a similar manner, other compounds of formula (Ig) are prepared.

EXAMPLE 4

Compounds of Formula (Ib)

A. To 4-(piperidin-4-yl)oxy-3-trifluoromethyl-N-(3-(6-hydroxy-3-amidinophenyl)prop-2-en-1-yl)benzenamine (75 mg) in MeOH was added phenyl carbamate (37 mg) and Et₃N (0.073 mL). The reaction mixture was stirred at ambient temperature for 3 hours, acidified with trifluoroacetic acid and purified on HPLC (10–40% acetonitrile in water with 0.1% trifluoroacetic acid). The corresponding peak was collected and freezed dried to afford 4-(N'-(aminocarbonyl)piperidin-4-yl)oxy-3-trifluoromethyl-N-(3-(6-hydroxy-3-amidinophenyl)prop-2-en-1-yl)benzenamine.

B. In a similar manner, other compounds of formula (Ib) are prepared.

EXAMPLE 5

Compounds of Formula (Id)

A. To a solution of 4-(piperidin-4-yl)oxy-3-trifluoromethyl-N-(2-(carboxy)ethylcarbonyl)-N-(3-(6-hydroxy-3-amidinophenyl)prop-2-en-1-yl)benzenamine (400 mg) in 100 mL CH₃CN was added acetyl chloride (500 mg) and Et₃N (1.28 g) at ambient temperature. The resulting solution was stirred at ambient temperature for 2 hours. LiOH (500 mg) in water (1.0 mL) was then added to the reaction mixture and the resulting reaction mixture was stirred at ambient temperature for 2 hours. Acidification with trifluoroacetic acid, concentration, purification on HPLC (H₂O/CH₃CN, gradient) and freeze-drying afforded 4-(N'-(acetyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine.

B. In a similar manner, other compounds of formula (Id) are prepared.

EXAMPLE 6

Compounds of Formula (Ih)

A. A solution of 4-(N-(t-butoxycarbonyl)piperidin-4-yl)oxybenzenamine (0.6 g, 2.0 mmol) in dimethyl formamide (25 mL) was treated with anhydrous potassium carbonate (0.56 g, 4.1 mmol), sodium iodide (0.61 g, 4.1 mmol), and 3-((chloromethyl)carbonylamino)-4-(benzyloxy) benzonitrile (0.65 g, 2.15 mmol) and was heated at 80° C. for 5.5 hours. The reaction was allowed to cool and poured onto ice water. The slurry was extracted with ethyl acetate (3×). The combined organic layers were washed with water (2×) and brine, dried and concentrated. Purification by flash chromatography on silica gel using a step gradient of 20 and 50% ethyl acetate in hexane gave, after concentration, 1 g of 4-(N"-(t-butoxycarbonyl)piperidin-4-yl)oxy-N-(N'-(6-benzyloxy-3-cyanophenyl)aminocarbonyl) methylbenzenamine, NMR (CDCl₃, TMS) 67 1.45 (s, 9), 1.66 (m, 2), 1.82 (m, 2), 3.25 (m, 2), 3.68 (m, 2), 3.82 (d, 2), 4.25 (m, 1), 4.35 (m, 1), 5.02 (s, 2), 6.53 (m, 2), 6.8 (m, 2), 6.9 (d, 1), 7.12 (m, 2), 7.28 (m, 4), 8.02 (s, 1), 9.58)s, 1).

B. In a similar manner, other compounds of formula (II) are prepared.

C. A solution of 4-(N"-(t-butoxycarbonyl)piperidin-4-yl) oxy-N-(N'-(6-benzyloxy-3-cyanophenyl)aminocarbonyl) methylbenzenamine (1 g, 1.8 mmol) in absolute ethanol (120 mL) and methylene chloride (20 mL) was placed under a nitrogen atmosphere, cooled in a dry ice/2-propanol bath, and treated with hydrogen chloride gas until a saturated solution was obtained. The flask was sealed with a septum and allowed to warm to ambient temperature overnight. Solvent was removed under reduced pressure. The residue was dissolved in absolute ethanol, treated with ammonia gas, and heated at reflux for about 4 hours. Solvent was removed under reduced pressure. Purification by preparative HPLC using a 15–55% gradient of acetonitrile (0.1% trifluoroacetic acid) in water (0.1% trifluoroacetic acid) gave about 0.3 g of 4-(piperidin-4-yl)oxy-N-(N'-(6-benzyloxy-3-amidinophenyl)aminocarbonyl)methylbenzenamine, NMR (DMSO, TMS) δ1.76 (m, 2H), 1.95 (m, 2H), 3.05 (m, 2H), 3.22 (m, 2H), 3.82 (s, 2H), 4.41 (m, 1H), 5.22 (s, 2H), 6.53 (d, 2H), 6.82 (d, 2H), 7.1 (m, 2H), 7.32 (m, 5H), 7.52 (m, 1H), 8.60 (s, 1H), 9.02 (s, 1H), 9.21 (s, 1H).

D. In a similar manner, other compounds of formula (Ih) are prepared.

EXAMPLE 7

Compounds of Formula (Ii)

A. A solution of 4-(piperidin-4-yl)oxy-N-(N'-(6-benzyloxy-3-cyanophenyl)aminocarbonyl)-methylbenzenamine (0.3 g, 6.3 mmol) in ethanol (25 mL) and triethylamine (5 mL) was treated with ethyl acetimidate hydrochloride (2 g, 16 mmol) and stirred overnight at ambient temperature. The reaction was complete by HPLC analysis [15–55% gradient of acetonitrile (0.1% trifluoroacetic acid) and water (0.1% trifluoroacetic acid)]. Solvent was removed under reduced pressure. Methanol was added and removed to yield a mixture of compounds of formula (Ii), 4-(N"-(acetyl)piperidin-4-yl)oxy-N-(N'-(6-benzyloxy-3-amidinophenyl)aminocarbonyl)methylbenzenamine and 4-(N"-(1-iminoethyl)piperidin-4-yl)oxy-N-(N'-(6-benzyloxy-3-amidinophenyl)-aminocarbonyl) methylbenzenamine.

B. In a similar manner, other compounds of formula (Ii) are prepared.

EXAMPLE 8

Compounds of Formula (Ij)

A. A mixture of compounds of formula (Ii), 4-(N"-(acetyl) piperidin-4-yl)oxy-N-(N'-(6-benzyloxy-3-amidinophenyl)

aminocarbonyl)methylbenzenamine and 4-(N"-(1-iminoethyl)piperidin- 4-yl)oxy-N-(N'-(6-benzyloxy-3-amidinophenyl)aminocarbonyl)-methylbenzenamine (0.3 g, 5.8 mmol) in a mixture of absolute ethanol (100 mL) and acetic acid (5 mL) was degassed with nitrogen and treated with 10% palladium on carbon (0.3 g, 50% water by wt). The reaction was placed on a Parr Hydrogenator under 43 psi of hydrogen gas for approximately 2 hours. Catalyst was removed by filtration and solvent was removed under reduced pressure. Purification by preparative HPLC using a 15–55% gradient of acetonitrile (0.1% trifluoroacetic acid) and water (0.1% trifluoroacetic acid) gave 0.2 g of a compound of formula (Ij) where X is NH, i.e., 4-(N"-(1-iminoethyl)piperidin-4-yl)oxy-N-(N'-(6-hydroxy-3-amidinophenyl)aminocarbonyl)-methylbenzenamine, NMR (DMSO, TMS) δ1.68 (m, 2), 1.95 (m, 2), 2.23 (s, 3), 3.5 (m, 2), 3.72 (m, 2), 3.82 (s, 2), 4.41 (m, 1) 6.57 (d, 2), 6.82 (d, 2), 7.02 (d, 1), 7.38 (d, 1), 8.56 (s, 1), 8.60 (s, 1), 8.8 (m, 2), 9.12 (s, 3), 9.21 (s, 1), 11.3 (m, 1) ppm, Anal. ($C_{22}H_{28}N_6O_3$-$H_2O$-$3.5C_2HF_3O_2$), and 0.04 g of a compound of formula (Ij) where X is O, i.e., 4-(N"-(acetyl)piperidin-4-yl)oxy-N-(N'-(6-hydroxy-3-amidinophenyl)aminocarbonyl) methylbenzenamine, NMR (DMSO, TMS) δ1.48 (m, 2), 1.82 (m, 2), 2.01 (s, 3), 3.2 (m, 2), 3.65 (m, 4), 4.38 (m, 1), 6.57 (d, 2), 6.82 (d, 2), 7.02 (d, 1), 7.38 (d, 1), 8.60 (m, 4), 9.1 (s, 3), 9.42 (s, 1), 9.21 (s, 1), 11.2 (s, 1) ppm, Anal. ($C_{22}H_{27}N_5O_4$-$1.5H_2O$-$2.1C_2HF_3O_2$).

B. In a similar manner, other compounds of formula (Ij) are prepared.

EXAMPLE 9

In methods similar to those described above in Examples 1–8, the following compounds of the invention were prepared:

4-(N"-(1-iminoethyl)piperidin-4-yl)oxy-N-(N'-(3-amidinophenyl)aminocarbonyl)methylbenzenamine;

4-(piperidin-4-yl)oxy-N-(N'-(6-hydroxy-3-amidinophenyl) aminocarbonyl)methylbenzenamine;

4-(N"-(1-iminoethyl)piperidin-4-yl)oxy-N-(N'-(6-hydroxy-3-amidinophenyl)aminocarbonyl)methylbenzenamine;

4-(N"-(acetyl)piperidin-4-yl)oxy-N-(N'-(6-hydroxy-3-amidinophenyl)aminocarbonyl)methylbenzenamine;

4-(N"-(1-iminoethyl)piperidin-4-yl)oxy-N-(aminocarbonylmethyl)-N-((N'-(3-amidinophenyl)amino)carbonyl)methylbenzenamine;

4-(N"-(1-iminoethyl)piperidin-4-yl)oxy-N-(1-(N'-(3-amidinophenyl)aminocarbonyl)ethyl)benzenamine;

4-(N"-(1-iminoethyl)piperidin-4-yl)oxy-N-(ethoxycarbonylmethyl)-N-((N'-(3-amidinophenyl)amino)carbonyl)methylbenzenamine;

4-(N"-(1-iminoethyl)piperidin-4-yl)oxy-N-(methyl)-N-((N'-(3-amidinophenyl)amino)carbonyl)methylbenzenamine;

4-(N"-(1-iminoethyl)piperidin-4-yl)oxy-N-(ethoxycarbonylmethyl)-N-(N'-(6-hydroxy-3-amidinophenyl)aminocarbonyl)-methylbenzenamine;

4-(N"-(1-iminoethyl)piperidin-4-yl)oxy-N-(methyl)-N-(N'-(6-hydroxy-3-amidinophenyl)aminocarbonyl)-methylbenzenamine;

4-(piperidin-4-yl)oxy-3-trifluoromethyl-N-(N'-(6-hydroxy-3-amidinophenyl)aminocarbonyl)methylbenzenamine;

4-(N"-(1-iminoethyl)piperidin-4-yl)oxy-3-carboxy-N-(N'-(6-hydroxy-3-amidinophenyl)aminocarbonyl) methylbenzenamine;

4-(N"-(1-iminoethyl)piperidin-4-yl)oxy-3-trifluoromethyl-N-(2-(carboxy)ethylcarbonyl)-N-(N'-(3-amidinophenyl) aminocarbonyl)methylbenzenamine;

4-(N"-(1-iminoethyl)piperidin-4-yl)oxy-3-trifluoromethyl-N-(2-(carboxy)ethylcarbonyl)-N-(N'-(6-hydroxy-3-amidinophenyl)aminocarbonyl)methylbenzenamine;

4-(N"-(methyl)piperidin-4-yl)oxy-N-(N'-(6-hydroxy-3-amidinophenyl)aminocarbonyl)methylbenzenamine;

4-(N"-(methyl)piperidin-4-yl)oxy-3-trifluoromethyl-N-(N'-(6-hydroxy-3-amidinophenyl)aminocarbonyl) methylbenzenamine;

4-(N"-(methyl)piperidin-4-yl)oxy-N-(1-methylethyl)-N-(N'-(6-benzyloxy-3-amidinophenyl)aminocarbonyl) methylbenzenamine;

4-(N"-(methyl)piperidin-4-yl)oxy-N-(1-methylethyl)-N-(N'-(6-hydroxy-3-amidinophenyl)aminocarbonyl) methylbenzenamine;

4-(N"-(methyl)piperidin-4-yl)oxy-3-trifluoromethyl-N-(1-methylethyl)-N-(N'-(6-hydroxy-3-amidinophenyl) aminocarbonyl)methylbenzenamine;

4-(N"-(methyl)piperidin-4-yl)oxy-3-trifluoromethyl-N-(N'-(6-hydroxy-3-amidinophenyl)aminocarbonyl) methylbenzenamine;

4-(piperidin-4-yl)oxy-N-(3-(6-hydroxy-3-amidinophenyl) propyl)benzenamine;

4-(N'-(1-iminoethyl)piperidin-4-yl)oxy-3-trifluoromethyl-N-(2-(carboxy)ethylcarbonyl)-N-(3-(6-hydroxy-3-amidinophenyl)propyl)benzenamine;

4-(N'-methylpiperidin-4-yl)oxy-N-(3-(6-hydroxy-3-amidinophenyl)propyl)benzenamine;

4-(piperidin-4-yl)oxy-3-trifluoromethyl-N-(3-(6-hydroxy-3-amidinophenyl)propyl)benzenamine;

4-(N'-(1-iminoethyl)piperidin-4-yl)oxy-3-trifluoromethyl-N-(3-(6-hydroxy- 3-amidinophenyl)propyl)benzenamine;

4-(N'-(1-iminoethyl)piperidin-4-yl)oxy-3-nitro-N-(3-(3-amidinophenyl)prop-2-en-1-yl)benzenamine;

4-(N'-(1-iminoethyl)piperidin-4-yl)oxy-N-(3-(3-amidinophenyl)prop-2-en-1-yl)benzenamine;

4-(N'-(1-iminoethyl)piperidin-4-yl)oxy-N-(3-(3-amidinophenyl)prop-2-en-1-yl)-N-(3-(3-amidinophenyl) prop-2-en-1-yl)benzenamine;

4-(N'-(1-iminoethyl)piperidin-4-yl)oxy-3-nitro-N-(carboxymethyl)-N-(3-(3-amidinophenyl)prop-2-en-1-yl) benzenamine;

4-(N'-(1-iminoethyl)piperidin-4-yl)oxy-3-trifluoromethyl-N-(3-(3-amidinophenyl)prop-2-en-1-yl)benzenamine;

4-(N'-(1-iminoethyl)piperidin-4-yl)oxy-3-(ethoxycarbonyl)-N-(3-(3-amidinophenyl)prop-2-en-1-yl)benzenamine;

4-(N'-(1-iminoethyl)piperidin-4-yl)oxy-3-(ethoxycarbonyl)-N-(3-(3-amidinophenyl)prop-2-en-1-yl)-N-(3-(3-amidinophenyl)prop-2-en-1-yl)benzenamine;

4-(N'-(1-iminoethyl)piperidin-4-yl)oxy-3-fluoro-N-(3-(3-amidinophenyl)prop-2-en-1-yl)benzenamine;

4-(N'-(1-iminoethyl)piperidin-4-yl)oxy-N-(2-(ethoxycarbonyl)propyl)-N-(3-(3-amidinophenyl)prop-2-en-1-yl)benzenamine;

4-(piperidin-4-yl)oxy-3-(ethoxycarbonyl)-N-(3-(3-amidinophenyl)prop-2-en-1-yl)benzenamine;

4-(piperidin-4-yl)oxy-3-(ethoxycarbonyl)-N-(3-(3-amidinophenyl)prop-2-en-1-yl)-N-(3-(3-amidinophenyl) prop-2-en-1-yl)benzenamine;

4-(N'-(1-iminoethyl)piperidin-4-yl)oxy-3-(ethoxycarbonyl)-N-(ethoxycarbonylmethyl)-N-(3-(3-amidinophenyl)prop-2-en-1-yl)benzenamine;

4-(piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3,5-difluoro-N-(3-(3-amidinophenyl)prop-2-en-1-yl)benzenamine;

4-(N'-acetylpiperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-trifluoromethyl-N-(3-(6-hydroxy-3-amidinophenyl)prop-2-en-1-yl) benzenamine;

4-(piperidin-4-yl)oxy-3-trifluoromethyl-N-(3-(6-benzyloxy-3-amidinophenyl)prop-2-en-1-yl)benzenamine;

4-(piperidin-4-yl)oxy-N-(3-(6-hydroxy-3-amidinophenyl)prop-2-en-1-yl)benzenamine;

4-(N'-(1-iminoethyl)piperdin-4-yl)oxy-3,5-difluoro-N-(3-(3-amidinophenyl)prop-2-en-1-yl)benzenamine;

4-(N'-(1-iminoethyl)piperidin-4-yl)oxy-N-(1-methylethyl)-N-(3-(3-amidinophenyl)prop-2-en-1-yl)benzenamine;

4-(N'-(1-iminoethyl)piperidin-4-yl)oxy-N-(3-(6-hydroxy-3-amidinophenyl)prop-2-en-1-yl)benzenamine;

4-(N'-(1-iminoethyl)piperidin-4-yl)oxy-3-fluoro-N-(methoxycarbonylmethyl)-N-(3-(3-amidinophenyl)prop-2-en-1-yl)benzenamine;

4-(N'-(1-iminoethyl)piperidin-4-yl)oxy-3-trifluoromethyl-N-(methoxycarbonylmethyl)-N-(3-(3-amidinophenyl)prop-2-en-1-yl)benzenamine;

4-(N'-(1-iminoethyl)piperidin-4-yl)oxy-3-trifluoromethyl-N-(methyl)-N-(3-(3-amidinophenyl)prop-2-en-1-yl)benzenamine;

4-(N'-(1-iminoethyl)piperidin-4-yl)oxy-3-trifluoromethyl-N-(aminocarbonylmethyl)-N-(3-(3-amidinophenyl)prop-2-en-1-yl)benzenamine;

4-(N'-(1-iminoethyl)piperidin-4-yl)oxy-3-fluoro-N-(aminocarbonylmethyl)-N-(3-(3-amidinophenyl)prop-2-en-1-yl)benzenamine;

4-(N'-(1-iminoethyl)piperidin-4-yl)oxy-3-nitro-N-(2-(carboxy)ethylcarbonyl)-N-(3-(3-amidinophenyl)prop-2-en-1-yl)benzenamine;

4-(piperidin-4-yl)oxy-3-carboxy-N-(3-(3-amidinophenyl)prop-2-en-1-yl)benzenamine;

4-(piperidin-4-yl)oxy-3-(methoxycarbonyl)-N-(3-(3-amidinophenyl)prop-2-en-1-yl)benzenamine;

4-(N'-(1-iminoethyl)piperidin-4-yl)oxy-3-carboxy-N-(3-13(3-amidinophenyl)prop-2-en-1-yl)benzenamine;

4-(N'-(1-iminoethyl)piperidin-4-yl)oxy-3-(methoxycarbonyl)-N-(3-(3-1amidinophenyl)prop-2-en-1-yl)benzenamine;

4-(N'-(methyl)piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-trifluoromethyl-N-acetyl-N-(3-(6-hydroxy-3-amidinophenyl)prop-2-en-1-yl)benzenamine;

4-(N'-(methyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-carboxy-N-((1-methylethyl)carbonyl)-N-(3-(6-hydroxy-3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(6-hydroxy-3-amidinophenyl)prop-2-en-1-yl)benzenamine;

4-(piperidin-4-yl)oxy-3-trifluoromethyl-N-(benzyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-((1-methylethyl)carbonyl)-N-(3-(6-hydroxy-3-amidinophenyl)prop-2-en-1-yl)benzenamine;

4-(N'-(1-iminoethyl)piperidin-4-yl)oxy-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(benzyl)-N-(3-(6-hydroxy-3-amidinophenyl)prop-2-en-1-yl)benzenamine;

4-(piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(piperidin-4-yl)oxy-3-trifluoromethyl-N-acetyl-N-(3-(6-hydroxy-3-amidinophenyl)prop-2-en-1-yl)benzenamine;

4-(N'-(1-iminoethyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(acetyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(methyl)piperidin-4-yl)oxy-3-trifluoromethyl-N-(2-(methoxycarbonyl)ethylcarbonyl)-N-(3-(6-hydroxy-3-amidinophenyl)prop-2-en-1-yl)benzenamine;

4-(N'-(methyl)piperidin-4-yl)oxy-3-trifluoromethyl-N-acetyl-N-(3-(6-hydroxy-3-amidinophenyl)prop-2-en-1-yl)benzenamine;

4-(N'-(1-iminoethyl)piperidin-4-yl)oxy-3-trifluoromethyl-N-(methoxycarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(benzyl)-N-(3-(6-hydroxy-3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(3-amidinophenyl)prop-2-en-1-yl)benzenamine;

4-(N'-(1-iminoethyl)piperidin-4-yl)oxy-3-carboxy-N-((1-methylethyl)carbonyl)-N-(3-(3-amidinophenyl)prop-2-en-1-yl)benzenamine;

4-(N'-(aminocarbonyl)piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-(methoxycarbonyl)-N-(2-(methoxycarbonyl)ethylcarbonyl)-N-(3-(6-hydroxy-3-amidinophenyl)prop-2-en-1-yl)benzenamine;

4-(N'-(1-iminoethyl)piperidin-4-yl)oxy-3-carboxy-N-(2-(aminocarbonyl)ethylcarbonyl)-N-(3-(6-hydroxy-3-amidinophenyl)prop-2-en-1-yl)benzenamine;

4-(N'-(methylsulfonyl)piperidin-4-yl)oxy-3-trifluoromethyl-N-(3-(6-hydroxy-3-amidinophenyl)prop-2-en-1-yl)benzenamine;

4-(N'-(methylsulfonyl)piperidin-4-yl)oxy-3-trifluoromethyl-N-((1-methylethyl)carbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(2-(ethoxycarbonyl)ethylcarbonyl)-N-(3-(3-amidinophenyl)prop-2-en-1-yl)benzenamine;

4-(N'-(methyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(acetyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(ethoxycarbonyl)piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-(nitro)-N-(aminocarbonylmethyl)-N-(3-(3-amidinophenyl)prop-2-en-1-yl)benzenamine;

4-(N'-(ethoxycarbonylmethyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-((1,2-di(ethoxycarbonyl)ethyl)aminocarbonyl)-N-(3-(3-amidinophenyl)prop-2-en-1-yl)benzenamine;

4-(N'-(1-iminoethyl)piperidin-4-yl)oxy-3-trifluoromethyl-N-((1,2-di(carboxy)ethyl)aminocarbonyl)-N-(3-(3-amidinophenyl)prop-2-en-1-yl)benzenamine;

4-(piperidin-4-yl)oxy-3-carboxy-N-(2-(carboxy)ethylcarbonyl)-N-(3-(3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(3-amidinophenyl)prop-2-en-1-yl)benzenamine;

4-(N'-(acetyl)piperidin-4-yl)oxy-3-trifluoromethyl-N-((1,2-di(ethoxycarbonyl)ethyl)aminocarbonyl)-N-(3-(3-amidinophenyl)prop-2-en-1-yl)benzenamine;

4-(N'-(acetyl)piperidin-4-yl)oxy-3-trifluoromethyl-N-((3,4-di(ethoxycarbonyl)phenyl)carbonyl)-N-(- 3-(3-amidinophenyl)prop-2-en-1-yl)benzenamine;

4-(N'-(carboxymethyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(acetyl)piperidin-4-yl)oxy-3-trifluoromethyl-N-((1,2-di(carboxy)ethyl)aminocarbonyl)-N-(3-(3-amidinophenyl)prop-2-en-1-yl)benzenamine;

4-(N'-iminoethyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(methyl)piperidin-4-yl)oxy-3-trifluoromethyl-N-((1,2-di(carboxy)ethyl)aminocarbonyl)-N-(3-(3-amidinophenyl)prop-2-en-1-yl)benzenamine;

4-(N'-(acetyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(1-iminoethyl)piperidin-4-yl)oxy-3-trifluoromethyl-N-((3,4-di(ethoxycarbonyl)phenyl)carbonyl)-N-(3-(3-amidinophenyl)prop-2-en-1-yl)benzenamine;

4-(N'-(methyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(methyl)piperidin-4-yl)oxy-3-trifluoromethyl-N-((3,4-di(ethoxycarbonyl)phenyl)carbonyl)-N-(3-(3-amidinophenyl)prop-2-en-1-yl)benzenamine;

4-(N'-(carboxymethyl)piperidin-4-yl)oxy-3-trifluoromethyl-N-(2-(carboxy)ethylcarbonyl)-N-(3-(3-amidinophenyl)prop-2-en-1-yl)benzenamine;

4-(N'-(carboxymethyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(carboxymethyl)piperidin-4-yl)oxy-3-trifluoromethyl-N-(3-(3-amidinophenyl)prop-2-en-1-yl)benzenamine;

4-(piperidin-4-yl)oxy-3-(ethoxycarbonyl)-N-(3-(3-amidinophenyl)prop-2-en-1-yl)-N-(3-)(3-amidinophenyl)prop-2-en-1-yl)benzenamine;

4-(piperidin-4-yl)oxy-3-trifluoromethyl-N-(3-(6-benzyloxy-3-amidinophenyl)prop-2-en-1-yl)-N-(3-(6-benzyloxy-3-amidinophenyl)prop-2-en-1-yl)benzenamine;

4-(N'-(1-iminoethyl)piperidin-4-yl)oxy-3-(nitro)-N-(2-methyl-3-(3-amidinophenyl)prop-2-en-1-yl)benzenamine;

4-(piperidin-4-yl)oxy-N-(2-methyl-3-(6-hydroxy-3-amidinophenyl)prop-2-en-1-yl)benzenamine;

4-(piperidin-4-yl)oxy-N-(2-methyl-3-(6-benzyloxy-3-amidinophenyl)prop-2-en-1-yl)benzenamine;

4-(N'-(1-iminoethyl)piperidin-4-yl)oxy-N-(2-methyl-3-(6-hydroxy-3-amidinophenyl)prop-2-en-1-yl)benzenamine;

4-(N'-(acetyl)piperidin-4-yl)oxy-N-(2-methyl-3-(6-hydroxy-3-amidinophenyl)prop-2-en-1-yl)benzenamine;

4-(N'-(1-iminoethyl)piperidin-4-yl)oxy-N-(2-methyl-3-(6-benzyloxy-3-amidinophenyl)prop-2-en-1-yl)benzenamine;

4-(piperidin-4-yl)oxy-3-carboxy-N-(2-(carboxy)ethylcarbonyl)-N-(2-methyl-3-(3-(3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(2-methyl-3-(6-hydroxy-3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(2-methyl-3-(3-amidinophenyl)prop-2-en-1-yl)benzenamine;

4-(N'-(carboxymethyl)piperidin-4-yl)oxy-3-trifluoromethyl-N-(2-(carboxy)ethylcarbonyl)-N-(2-methyl-3-(6-hydroxy-3-amidinophenyl)prop-2-en-1-yl)benzenamine;

4-(piperidin-4-yl)oxy-N-(2-methyl-3-(6-hydroxy-3-amidinophenyl)prop-1-yl)benzenamine;

4-(N'-(1-iminoethyl)piperidin-4-1yl)oxy-N-(2-methyl-3-(6-hydroxy-3-amidinophenyl)prop-1-yl)benzenamine;

4-(N'-(actyl)piperidin-4-yl)oxy-3-trifluoromethyl-N-(2-(ethoxycarbonyl)ethylcarbonyl)-N-(2-methyl-3-(6-hydroxy-3-amidinophenyl)prop-1-yl)benzenamine;

4-(N'-(acetyl)piperidin-4-yl)oxy-3-trifluoromethyl-N-(2-(carboxy)ethylcarbonyl)-N-(2-methyl-3-(6-hydroxy-3-amidinophenyl)prop-1-yl)benzenamine;

4-(N'-(1-iminoethyl)piperidin-4-yl)oxy-3-nitro-N-(3-(3-amidinophenyl)benzyl)benzenamine;

4-(N'-(acetyl)piperidin-4-yl)oxy-3-methoxy-N-(3-(3-amidinophenyl)benzyl)benzenamine;

4-(N'-(1-iminoethyl)piperidin-4-yl)oxy-N-(3-(3-amidinophenyl)benzyl)benzenamine;

4-(piperidin-4-yl)oxy-3-(ethoxycarbonyl)-N-(3-(3-amidinophenyl)benzyl)benzenamine;

4-(N'-(1-iminoethyl)piperidin-4-yl)oxy-3-(ethoxycarbonyl)-N-(3-(3-amidinophenyl)benzyl)benzenamine;

4-(N'-(1-iminoethyl)piperidin-4-yl)oxy-3-carboxy-N-(3-(3-amidinophenyl)benzyl)benzenamine;

4-(piperidin-4-yl)oxy-3-(ethoxycarbonyl)-N-(ethoxycarbonylmethyl)-N-(3-(3-amidinophenyl)benzyl)benzenamine;

4-(N'-(1-iminoethyl)piperidin-4-yl)oxy-3-(ethoxycarbonyl)-N-(ethoxycarbonylmethyl)-N-(3-(3-amidinophenyl)benzyl)benzenamine;

4-(N'-(1-iminoethyl)piperidin-4-yl)oxy-3-carboxy-N-(carboxymethyl)-N-(3-(3-amidinophenyl)benzyl)benzenamine;

4-(N'-(1-iminoethyl)piperidin-4-yl)oxy-3-trifluoromethyl-N-(3-(3-amidinophenyl)benzyl)benzenamine;

4-(piperidin-4-yl)oxy-3-trifluoromethyl-N-(3-(3-amidinophenyl)benzyl)benzenamine;

4-(N'-(1-iminoethyl)piperidin-4-yl)oxy-3-trifluoromethyl-N-(ethoxycarbonylmethyl)-N-(3-(3-amidinophenyl)benzyl)benzenamine;

4-(N'-(1-iminoethyl)piperidin-4-yl)oxy-3-(ethoxycarbonyl)-N-(3-(3-amidinophenyl)benzyl)-N-(3-(3-amidinophenyl)benzyl)benzenamine;

4-(N'-(1-iminoethyl)piperidin-4-yl)oxy-3-carboxy-N-(3-(3-amidinophenyl)benzyl)-N-(3-(3-amidinophenyl)benzyl)benzenamine;

4-(tetrahydropyran-4-yl)oxy-3-trifluoromethyl-N-(3-(6-hydroxy-3-amidinophenyl)prop-2-en-1-yl)benzenamine;

4-(thian-4-yl)oxy-3-trifluoromethyl-N-(3-(6-hydroxy-3-amidinophenyl)prop-2-en-1-yl)benzenamine.

EXAMPLE 10

This example illustrates the preparation of representative pharmaceutical compositions for oral administration containing a compound of the invention, or a pharmaceutically acceptable salt thereof:

| A. | Ingredients | % wt./wt. |
|---|---|---|
| | Compound of the invention | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Compound of the invention | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Compound of the invention | 0.1g |
| | Propylene glycol | 20.0g |
| | Polyethylene glycol 400 | 20.0g |
| | Polysorbate 80 | 1.0g |
| | Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 11

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

EXAMPLE 12

This example illustrates the preparation of a representative pharmaceutical composition in suppository form containing a compound of the invention, or a pharmaceutically acceptable salt thereof:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 13

This example illustrates the preparation of a representative pharmaceutical formulation for insufflation containing a compound of the invention, or a pharmaceutically acceptable salt thereof:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 14

This example illustrates the preparation of a representative pharmaceutical formulation in nebulized form containing a compound of the invention, or a pharmaceutically acceptable salt thereof:

| Ingredients | % wt./wt. |
| --- | --- |
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 15

This example illustrates the preparation of a representative pharmaceutical formulation in aerosol form containing a compound of the invention, or a pharmaceutically acceptable salt thereof:

| Ingredients | % wt./wt. |
| --- | --- |
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 16

In Vitro Assay For Factor Xa and Thrombin

This assay demonstrates the activity of the compounds of the invention towards factor Xa, thrombin and tissue plasminogen activator. The activities were determined as an initial rate of cleavage of the peptide p-nitroanilide by the enzyme. The cleavage product, p-nitroaniline, absorbs at 405 nm with a molar extinction coefficient of 9920 $M^{-1}cm^{-1}$.

Reagents and Solutions

Dimethyl sulfoxide (DMSO) (Baker analyzed grade).
Assay buffer:
  50 mM TrisHCl, 150 mM NaCl, 2.5 mM $CaCl_2$, and 0.1% polyethylene glycol 6000, pH 7.5.

Enzymes (Enzyme Research Lab.)
1. Human factor Xa stock solution: 0.281 mg/mL in assay buffer, stored at −80° C. (working solution (2×): 106 ng/mL or 2 nM in assay buffer, prepare prior to use).
2. Human thrombin stock solution: Concentration as specified by the supplier, stored at −80° C. (working solution (2×): 1200 ng/mL or 32 nM in assay buffer, prepare prior to use).
3. Human tissue plasminogen activator (tPA) (Two chains, Sigma or American Diagnostica Inc.) stock solution: Concentration as specified by the supplier, stored at −80° C. (working solution (2×): 1361 ng/mL or 20 nM in assay buffer, prepare prior to use).

Chromogenic Substrates (Pharmacia Hepar Inc.)
1. S2222 (FXa assay) stock solution: 6 mM in deionized $H_2O$, store at 4° C. (working solution (4×): 656 $\mu$M in assay buffer).
2. S2302 (Thrombin assay) stock solution: 10 mM in deionized $H_2O$, stored at 4° C. (working solution (4×): 1200 $\mu$M in assay buffer).
3. S2288 (tPA assay) stock solution: 10 mM in deionized $H_2O$, stored at 4° C. (working solution (4×): 1484 $\mu$M in assay buffer for Sigma tPA, or 1120 $\mu$M for American Diagnostica tPA).

Standard inhibitor compound stock solution:
  5 mM in DMSO, stored at −20° C.
Test compounds (compounds of the invention) stock solutions:
  10 mM in DMSO, stored at −20° C.

Assay Procedure

Assays were performed in 96-well microtiter plates in a total volume of 200 $\mu$l. Assay components were in final concentration of 50 mM TrisHCl, 150 mM NaCl, 2.5 mM $CaCl_2$, 0.1% polyethylene glycol 6000, pH 7.5, in the absence or presence of the standard inhibitor or the test compounds and enzyme and substrate at following concentrations: (1) 1 nM factor Xa (0.1 nM or 0.2 nM factor Xa for compounds with $K_i$Xa in low picomolar range) and 164 $\mu$M S2222; (2) 16 nM thrombin and 300 $\mu$M S2302; and (3) 10 nM tPA and 371 $\mu$M or 280 $\mu$M S2288. Concentrations of the standard inhibitor compound in the assay were from 5 $\mu$M to 0.021 $\mu$M in 1 to 3 dilution. Concentration of the test compounds in the assay typically were from 10 $\mu$M to 0.041 $\mu$M in 1 to 3 dilution. For potent test compounds, the concentrations used in the factor Xa assay were further diluted 100 fold (100 nM to 0.41 nM) or 1000 fold (10 nM to 0.041 nM). All substrate concentrations used are equal to their $K_m$ values under the present assay conditions. Assays were performed at ambient temperature.

The first step in the assay was the preparation of 10 mM test compound stock solutions in DMSO (for potent test compounds, 10 mM stock solutions were further diluted to 0.1 or 0.01 $\mu$M for the factor Xa assay), followed by the preparation of test compound working solutions (4×) by a serial dilutions of 10 mM stock solutions with Biomek 1000 in 96 deep well plates as follows:

(a) Prepare a 40 $\mu$M working solution by diluting the 10 mM stock 1 to 250 in assay buffer in 2 steps: 1 to 100, and 1 to 2.5.
(b) Make another five serial dilutions (1:3) of the 40 $\mu$M solution (600 $\mu$L for each concentration). A total of six diluted test compound solutions were used in the assay. Standard inhibitor compound (5 mM stock) or DMSO (control) went through the same dilution steps as those described above for test compounds.

The next step in the assay was to dispense 50 $\mu$L of the test compound working solutions (4×) (from 40 $\mu$M to 0.164 $\mu$M) in duplicate to microtiter plates with Biomek. To this was added 100 $\mu$L of enzyme working solution (2×) with Biomek. The resulting solutions were incubated at ambient temperature for 10 minutes.

To the solutions was added 50 $\mu$L of substrate working solution (4×) with Biomek.

The enzyme kinetics were measured at 405 nm at 10 seconds intervals for five minutes in a THERMOmax plate reader at ambient temperature. When a lower concentration of factor Xa was needed in the factor Xa assay, the enzyme kinetics were measured for fifteen minutes (0.2 nM factor Xa) or thirty minutes (0.1 nM factor Xa) at ambient temperature.

Calculation of $K_i$ of the Test Compounds

Enzyme initial rates were calculated as mOD/min based on the first two minutes readings. The $IC_{50}$ values were determined by fitting the data to the log-logit equation (linear) or the Morrison equation (non-linear) with an EXCEL spread-sheet. $K_i$ values were then obtained by dividing the $IC_{50}$ by 2. Routinely, $K_i$ (factor Xa) values less than 3 nM were calculated from the Morrison equation.

Compounds of the invention, when tested in this assay, demonstrated the selective ability to inhibit human factor Xa and human thrombin.

EXAMPLE 17

In Vitro Assay for Human Prothrombinase

This assay demonstrates the ability of the compounds of the invention to inhibit prothrombinase. Prothrombinase (PTase) catalyzes the activation of prothrombin to yield fragment 1.2 plus thrombin with meizothrombin as the intermediate. This assay is an end point assay. Activity of the prothrombinase is measured by activity of thrombin (one of the reaction products) or by the amount of thrombin formed/time based on a thrombin standard curve (nM vs mOD/min). For determination of $IC_{50}$ (PTase) of the compounds of the invention, PTase activity was expressed by thrombin activity (mOD/min).

Materials

Enzymes:
1. Human factor Va (Haematologic Technologies Inc., Cat# HCVA-0110) working solution: 1.0 mg/mL in 50% glycerol, 2 mM $CaCl_2$, stored at −20° C.
2. Human factor Xa (Enzyme Res. Lab. cat# HFXa1011) working solution: 0.281 mg/mL in assay buffer (without BSA), stored at −80° C.
3. Human prothrombin (FII) (Enzyme Res. Lab., Cat# HP1002) working solution:
    Diluted FII to 4.85 mg/mL in assay buffer (without BSA), stored at −80° C.
    Phospholipid (PCPS) vesicles:
    PCPS vesicles (80% PC, 20% PS) were prepared by modification of the method reported by Barenholz et al., *Biochemistry* (1977), Vol. 16, pp. 2806–2810.
    Phosphatidyl serine (Avanti Polar Lipids, Inc., Cat#840032):
    10 mg/mL in chloroform, purified from brain, stored −20° C. under nitrogen or argon.
    Phosphatidyl Choline (Avanti Polar Lipids, Inc., Cat# 850457):
    50 mg/ml in chloroform, synthetic 16:0–18:1 Palmitoyl-Oleoyl, stored at −20° C. under nitrogen or argon.
    Spectrozyme-TH (American Diagnostica Inc., Cat# 238L, 50 μmoles, stored at ambient temperature) working solution: Dissolved 50 μmoles in 10 mL $dH_2O$.
    BSA (Sigma Chem Co., Cat# A-7888, Fraction V, RIA grade).
    Assay buffer: 50 mM TrisHCl, pH 7.5, 150 mM NaCl, 2.5 mM $CaCl_2$, 0.1% PEG 6000 (BDH), 0.05% BSA (Sigma, Fr.V, RIA grade).

For one plate assay, prepare the following working solutions:
1. Prothrombinase complex:
    (a) 100 μM PCPS (27.5 μL of PCPS stock (4.36 mM) diluted to final 1200 μL with assay buffer.
    (b) 25 nM Human factor Va: 5.08 μL of Va stock(1 mg/mL) was diluted to final 1200 μL with assay buffer.
    (c) 5 pM Human factor Xa: Dilute factor Xa stock (0.281 mg/mL) 1:1,220,000 with assay buffer. Prepare at least 1200 μL.
    Combine equal volumes (1100 μL) of each component in the order of PCPS, Va and Xa. Use immediately or store in ice (bring to ambient temperature before use).
2. 6 μM Human prothrombin (FII): dilute 124 μL of FII stock (4.85 mg/mL) to final 1400 μL with assay buffer.
3. 20 mM EDTA/Assay buffer: 0.8 mL of 0.5 M EDTA (pH 8.5) plus 19.2 mL assay buffer.
4. 0.2 mM Spectrozyme-TH/EDTA buffer: 0.44 mL of SPTH stock (5 mM) plus 10.56 mL of 20 mM EDTA/assay buffer.
5. Test compounds (compounds of the invention):
    Prepare a working solution (5×) from 10 mM stock (DMSO) and make a series of 1:3 dilution. Compounds were assayed at 6 concentrations in duplicate.

Assay Conditions and Procedure

Prothrombinase reaction was performed in final 50 μL of mixture containing PTase (20 μM PCPS, 5 nM hFVa, and 1 pM hFXa), 1.2 μM human factor II and varied concentration of the test compounds (5 μM to 0.021 μM or lower concentration range). Reaction was started by addition of PTase and incubated for 6 minutes at ambient temperature. Reaction was stopped by addition of EDTA/buffer to final 10 mM. Activity of thrombin (product) was then measured in the presence of 0.1 mM of Spectrozyme-TH as substrate at 405 nm for 5 minutes (10 seconds intervals) at ambient temperature in a THEROmax microplate reader. Reactions were performed in 96-well microtiter plates.

In the first step of the assay, 10 μL of diluted test compound (5×) or buffer was added to the plates in duplicate. Then 10 μL of prothrombin (hFII) (5×) was added to each well. Next 30 μL PTase was added to each well, mix for about 30 seconds. The plates were then incubated at ambient temperature for 6 minutes.

In the next step, 50 μL of 20 mM EDTA (in assay buffer) was added to each well to stop the reaction. The resulting solutions were then mixed for about 10 seconds. Then 100 μL of 0.2 mM spectrozyme was added to each well. The thrombin reaction rate was then measured at 405 nm for 5 minutes at 10 seconds intervals in a Molecular Devices microplate reader.

Calculations

Thrombin reaction rate was expressed as mOD/min. using OD readings from the five minute reaction. $IC_{50}$ values were calculated with the log-logit curve fit program.

The compounds of the invention demonstrated the ability to inhibit pro-thrombinase when tested in this assay.

EXAMPLE 18

In Vivo Assay

The following assay demonstrates the ability of the compounds to act as anti-coagulants.

Male rats (250–330 g) were anesthetized with sodium pentobarbital (90 mg/kg, i.p.) and prepared for surgery. The left carotid artery was cannulated for the measurement of blood pressure as well as for taking blood samples to monitor clotting variables (prothrombin time (PT) and activated partial thromboplastin time (aPTT)). The tail vein was cannulated for the purpose of administering the test compounds (i.e., the compounds of the invention and standards) and the thromboplastin infusion. The abdomen was opened via a mid-line incision and the abdominal vena cava was isolated for 2–3 cm distal to the renal vein. All venous branches in this 2–3 cm segment of the abdominal vena cava were ligated. Following all surgery, the animals were allowed to stabilize prior to beginning the experiment. Test compounds were administered as an intravenous bolus (t=0). Three minutes later (t=3), a 5-minute infusion of thromboplastin was begun. Two minutes into the infusion (t=5), the abdominal vena cava was ligated at both the proximal and distal ends. The vessel was left in place for 60 minutes, after which it was excised from the animal, slit open, the clot (if any) carefully removed, and weighed. Statistical analysis on the results was performed using a Wilcoxin-matched-pairs signed rank test.

The compounds of the invention, when tested in this assay, demonstrated the ability to inhibit the clotting of the blood.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula (I):

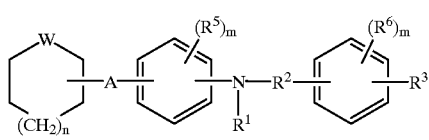

wherein:

A is —O— or —N($R^7$)—;

W is —N($R^4$)—, —S— or —O—;

each m is independently 0, 1, 2, 3 or 4;

n is 0 or 1;

$R^1$ is hydrogen, alkyl, alkylcarbonyl, phenylalylidenyl (wherein the phenyl group is optionally substituted by alkyl, halo, alkoxy, aralkoxy, —C(NH)—$NH_2$, —C(NH)N(H)O$R^7$, —C(NH)N(H)C(O)O$R^9$, —C(NH)N(H)C(O)$R^9$, —C(NH)N(H)S(O)$_2R^9$, or —C(NH)N(H)C(O)N(H)$R^7$), alkoxycarbonylalkyl, carboxyalkyl, aminocarbonylalkyl, monoalkylaminocarbonylalkyl, dialkylaminocarbonylalkyl, alkoxycarbonyl, phenylcarbonyl (wherein the phenyl group is optionally substituted by carboxy or alkoxycarbonyl), carboxyalkylcarbonyl, alkoxycarbonylalkylcarbonyl, aminocarbonylalkylcarbonyl, benzyl (wherein the phenyl group is optionally substituted by alkyl, halo, alkoxy, aralkoxy, —C(NH)—$NH_2$, —C(NH)N(H)O$R^7$, —C(NH)N(H)C(O)O$R^9$, —C(NH)N(H)C(O)$R^9$, —C(NH)N(H)S(O)$_2R^9$, or —C(NH)N(H)C(O)N(H) $R^7$), mono[dialkoxycarbonyl]alkylaminocarbonyl, mono[dicarboxy]alkylaminocarbonyl, alkylsulfonyl, arylsulfonyl or dialkylaminosulfonyl;

$R^2$ is —[C($R^7$)$_2$]$_m$—, —[C($R^7$)$_2$]$_m$—C(O)—N($R^8$)—, or —[C($R^7$)$_2$]$_m$—[C($R^8$)]=CH—;

or $R^2$ is

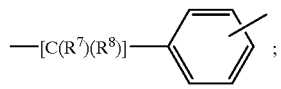

$R^3$ is —C(NH)$NH_2$, —C(NH)N(H)O$R^7$, —C(NH)N(H)C(O)O$R^9$, —C(NH)N(H)C(O)$R^9$, —C(NH)N(H)S(O)$_2R^9$, or —C(NH)N(H)C(O)N(H)$R^7$;

$R^4$ is hydrogen, alkyl, alkylcarbonyl, aminocarbonyl, monoalkylaminocarbonyl, dialkylaminocarbonyl, aminosulfonyl, alkoxycarbonyl, carboxyalkyl, alkoxycarbonylalkyl, or —C(NH)$CH_3$;

each $R^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl;

$R^6$ is hydrogen, alkyl, hydroxy, alkoxy, aralkoxy (wherein the aryl group is optionally substituted by alkyl, halo or alkoxy);

each $R^7$ and $R^8$ is independently hydrogen, alkyl, aryl, or aralkyl; and each $R^9$ is alkyl or aralkyl;

as a single stereoisomer or a mixture thereof; or a pharmaceutically acceptable salt thereof.

2. The compound of claim 1 wherein

A is —O—;

W is —N($R^4$)—;

each m is independently 0, 1 or 2;

n is 1;

$R^2$ is —[C($R^7$)$_2$]$_m$—C(O)—N($R^8$)—; and $R^3$ is —C(NH)$NH_2$.

3. The compound of claim 2 selected from the group consisting of the following:

4-(N"-(1-iminoethyl)piperidin-4-yl)oxy-N-(N'-(3-amidinophenyl)aminocarbonyl)methylbenzenamine;

4-(piperidin-4-yl)oxy-N-(N'-(6-hydroxy-3-amidinophenyl)aminocarbonyl)methylbenzenamine;

4-(N"-(1-iminoethyl)piperidin-4-yl)oxy-N-(N'-(6-hydroxy-3-amidinophenyl)aminocarbonyl)methylbenzenamine;

4-(N"-(acetyl)piperidin-4-yl)oxy-N-(N'-(6-hydroxy-3-amidinophenyl)aminocarbonyl)methylbenzenamine;

4-(N"-(1-iminoethyl)piperidin-4-yl)oxy-N-(aminocarbonylmethyl)-N-((N'-(3-amidinophenyl)amino)carbonyl)methylbenzenamine;

4-(N"-(1-iminoethyl)piperidin-4-yl)oxy-N-(1-(N'-(3-amidinophenyl)aminocarbonyl)ethyl)benzenamine;

4-(N"-(1-iminoethyl)piperidin-4-yl)oxy-N-(ethoxycarbonylmethyl)-N-((N'-(3-amidinophenyl)amino)carbonyl)methylbenzenamine;

4-(N"-(1-iminoethyl)piperidin-4-yl)oxy-N-(methyl)-N-((N'-(3-amidinophenyl)amino)carbonyl)methylbenzenamine;

4-(N"-(1-iminoethyl)piperidin-4-y)oxy-N-(ethoxycarbonylmethyl)-N-(N'-(6-hydroxy-3-amidinophenyl)aminocarbonyl)-methylbenzenamine;

4-(N"-(1-iminoethyl)piperidin-4-yl)oxy-N-(methyl)-N-(N'-(6-hydroxy-3-amidinophenyl)aminocarbonyl)-methylbenzenamine;

4-(piperidin-4-yl)oxy-3-trifluoromethyl-N-(N'-(6-hydroxy-3-amidinophenyl)aminocarbonyl)methylbenzenamine;

4-(N"-(1-iminoethyl)piperidin-4-yl)oxy-3-carboxy-N-(N'-(6-hydroxy-3-amidinophenyl)aminocarbonyl) methylbenzenamine;

4-(N"-(1-iminoethyl)piperidin-4-yl)oxy-3-trifluoromethyl-N-(2-(carboxy)ethylcarbonyl)-N-(N'-(3-amidinophenyl) aminocarbonyl)methylbenzenamine;

4-(N"-(1-iminoethyl)piperidin-4-yl)oxy-3-trifluoromethyl-N-(2-(carboxy)ethylcarbonyl)-N-(N'-(6-hydroxy-3-amidinophenyl)aminocarbonyl)methylbenzenamine;

4-(N"-(methyl)piperidin-4-yl)oxy-N-(N'-(6-hydroxy-3-amidinophenyl)aminocarbonyl)methylbenzenamine;

4-(N"-(methyl)piperidin-4-yl)oxy-3-trifluoromethyl-N-(N'-(6-hydroxy-3-amidinophenyl)aminocarbonyl) methylbenzenamine;

4-(N"-(methyl)piperidin-4-yl)oxy-N-(1-methylethyl)-N-(N'-(6-benzyloxy-3-amidinophenyl)aminocarbonyl) methylbenzenamine;

4-(N"-(methyl)piperidin-4-yl)oxy-N-(-methylethyl)-N-(N'-(6-hydroxy-3-amidinophenyl)aminocarbonyl) methylbenzenamine;

4-(N"-(methyl)piperidin-4-yl)oxy-3-trifluoromethyl-N-(1-methylethyl)-N-(N'-(6-hydroxy-3-amidinophenyl) aminocarbonyl)methylbenzenamine; and 4-(N''-(methyl)piperidin-4-yl)oxy-3-trifluoromethyl-N-(N'-(6-hydroxy-3-amidinophenyl)aminocarbonyl) methylbenzenamine.

4. The compound of claim 1 wherein

A is —O—;
W is —N(R$^4$)—;
each m is independently 0, 1 or 2;
n is 1;
R$^2$ is —[C(R$^7$)$_2$]$_m$—; and
R$^3$ is —C(NH)NH$_2$.

5. The compound of claim 4 selected from the group consisting of the following:

4-(piperidin-4-yl)oxy-N-(3-(6-hydroxy-3-amidinophenyl) propyl)benzenamine;
4-(N'-(1-iminoethyl)piperidin-4-yl)oxy-3-trifluoromethyl-N-(2-(carboxy)ethylcarbonyl)-N-(3-(6-hydroxy-3-amidinophenyl)propyl)benzenamine;
4-(N'-methylpiperidin-4-yl)oxy-N-(3-(6-hydroxy-3-amidinophenyl)propyl)benzenamine;
4-(piperidin-4-yl)oxy-3-trifluoromethyl-N-(3-(6-hydroxy-3-amidinophenyl)propyl)benzenamine;
4-(N'-(1-iminoethyl)piperidin-4-yl)oxy-3-trifluoromethyl-N-(3-(6-hydroxy-3-amidinophenyl)propyl)benzenamine;
4-(piperidin-4-yl)oxy-N-(2-methyl-3-(6-hydroxy-3-amidinophenyl)prop-1-yl)benzenamine;
4-(N'-(1-iminoethyl)piperidin-4-yl)oxy-N-(2-methyl-3-(6-hydroxy-3-amidinophenyl)prop-1-yl)benzenamine;
4-(N'-(acetyl)piperidin-4-yl)oxy-3-trifluoromethyl-N-(2-(ethoxycarbonyl)ethylcarbonyl)-N-(2-methyl-3-(6-hydroxy-3-amidinophenyl)prop-1-yl)benzenamine; and
4-(N'-(acetyl)piperidin-4-yl)oxy-3-trifluoromethyl-N-(2-(carboxy)ethylcarbonyl)-N-(2-methyl-3-(6-hydroxy-3-amidinophenyl)prop-1-yl)benzenamine.

6. The compound of claim 1 wherein

A is —O—;
W is —N(R$^4$)—;
each m is independently 0, 1 or 2;
n is 1;
R$^2$ is —[C(R$^7$)$_2$]$_m$—[C(R$^8$)]=CH—;
R$^3$ is —C(NH)NH$_2$; and
R$^3$ is hydrogen.

7. The compound of claim 6 selected from the group consisting of the following:

4-(N'-(1-iminoethyl)piperidin-4-yl)oxy-3-nitro-N-(3-(3-amidinophenyl)prop-2-en-1-yl)benzenamine;
4-(N'-(1-iminoethyl)piperidin-4-yl)oxy-N-(3-(3-amidinophenyl)prop-2-en-1-yl)benzenamine;
4-(N'-(1-iminoethyl)piperidin-4-yl)oxy-N-(3-(3-amidinophenyl)prop-2-en-1-yl)-N-(3-( 3-amidinophenyl)prop-2-en-1-yl)benzenamine;
4-(N'-(1-iminoethyl)piperidin-4-yl)oxy-3-nitro-N-(carboxymethyl)-N-(3-(3-amidinophenyl)prop-2-en-1-yl)benzenamine;
4-(N'-(1-iminoethyl)piperidin-4-yl)oxy-3-trifluoromethyl-N-(3-(3-amidinophenyl)prop-2-en-1-yl)benzenamine;
4-(N'-(1-iminoethyl)piperidin-4-yl)oxy-3-ethoxycarbonyl-N-(3-(3-amidinophenyl)prop-2-en-1-yl)benzenamine;
4-(N'-(1-iminoethyl)piperidin-4-yl)oxy-3-ethoxycarbonyl-N-(3-(3-amidinophenyl)prop-2-en-1-yl)-N-(3(3-amidinophenyl)prop-2-en-1-yl)benzenamine;
4-(N'-(1-iminoethyl)piperidin-4-yl)oxy-3-fluoro-N-(3-(3-amidinophenyl)prop-2-en-1-yl)benzenamine;
4-(N'-(1-iminoethyl)piperidin-4-yl)oxy-N-(2-(ethoxycarbonyl)propyl)-N-(3-(3-amidinophenyl)prop-2-en-1-yl)benzenamine;
4-(piperidin-4-yl)oxy-3-(ethoxycarbonyl)-N-(3-(3-amidinophenyl)prop-2-en-1-yl)benzenamine;
4-(piperidin-4-yl)oxy-3-(ethoxycarbonyl)-N-(3-(3-amidinophenyl)prop-2-en-1-yl)-N-(3-(3-amidinophenyl) prop-2-en-1-yl)benzenamine;
4-(N'-(1-iminoethyl)piperidin-4-yl)oxy-3-ethoxycarbonyl-N-(ethoxycarbonylmethyl)-N-(3-(3-amidinophenyl)prop-2-en-1-yl)benzenamine;
4-(piperidin-4-yl)oxy-3-trifluoromethyl-N-(3-(6-hydroxy-3-amidinophenyl)prop-2-en-1-yl)benzenamine;
4-(N'-(1-iminoethyl)piperidin-4-yl)oxy-3,5-difluoro-N-(3-(3-amidinophenyl)prop-2-en-1-yl)benzenamine;
4-(N'-(acetylpiperidin-4-yl)oxy-3-trifluoromethyl-N-(3-(6-hydroxy-3-amidinophenyl)prop-2-en-1-yl)benzenamine;
4-(N'-(1-iminoethyl)piperidin-4-yl)oxy-3-trifluoromethyl-N-(3-(6-hydroxy-3-amidinophenyl)prop-2-en-1-yl) benzenamine;
4-(piperidin-4-yl)oxy-3-trifluoromethyl-N-(3-(6-benzyloxy-3-amidinophenyl)prop-2-en-1-yl) benzenamine;
4-(piperidin-4-yl)oxy-N-(3-(6-hydroxy-3-amidinophenyl) prop-2-en-1-yl)benzenamine;
4-(N'-(1-iminoethyl)piperidin-4-yl)oxy-3,5-difluoro-N-(3-(3-amidinophenyl)prop-2-en-1-yl)benzenamine;
4-(N'-(1-iminoethyl)piperidin-4-yl)oxy-N-(1-methylethyl)-N-(3-(3-amidinophenyl)prop-2-en-1-yl)benzenamine;
4-(N'-(1-iminoethyl)piperidin-4-yl)oxy-N-(3-(6-hydroxy-3-amidinophenyl)prop-2-en-1-yl)benzenamine;
4-(N'-(1-iminoethyl)piperidin-4-yl)oxy-3-fluoro-N-(methoxycarbonylmethyl)-N-(3-(3-amidinophenyl)prop-2-en-1-yl)benzenamine;
4-(N'-(1-iminoethyl)piperidin-4-yl)oxy-3-trifluoromethyl-N-(methoxycarbonylmethyl)-N-(3-(3-amidinophenyl) prop-2-en-1-yl)benzenamine;
4-(N'-(1-iminoethyl)piperidin-4-yl)oxy-3-trifluoromethyl-N-(methyl)-N-(3-(3-amidinophenyl)prop-2-en-1-yl) benzenamine;
4-(N'-(1-iminoethyl)piperidin-4-yl)oxy-3-trifluoromethyl-N-(aminocarbonylmethyl)-N-(3-(3-amidinophenyl)prop-2-en-1-yl)benzenamine;
4-(N'-(1-iminoethyl)piperidin-4-yl)oxy-3-fluoro-N-(aminocarbonylmethyl)-N-(3-(3-amidinophenyl)prop-2-en-1-yl)benzenamine;
4-(N'-(1-iminoethyl)piperidin-4-yl)oxy-3-nitro-N-(2-(carboxy)ethylcarbonyl)-N-(3-(3-amidinophenyl)prop-2-en-1-yl)benzenamine;
4-(piperidin-4-yl)oxy-3-carboxy-N-(3-(3-amidinophenyl) prop-2-en-1-yl)benzenamine;
4-(piperidin-4-yl)oxy-3-methoxycarbonyl-N-(3(3-amidinophenyl)prop-2-en-1-yl)benzenamine;
4-(N'-(1-iminoethyl)piperidin-4-yl)oxy-3-carboxy-N-(3-(3-amidinophenyl)prop-2-en-1-yl)benzenamine;
4-(N'-(1-iminoethyl)piperdin-4-yl)oxy-3-methoxycarbonyl-N-(3-(3-amidinophenyl)prop-2-en-1-yl)benzenamine;
4-(N'-(methyl)piperidin-4-yl)oxy-3-trifluoromethyl-N-(3-(6-hydroxy-3-amidinophenyl)prop-2-en-1-yl) benzenamine;
4-(N'-(1-iminoethyl)piperidin-4-yl)oxy-3-trifluoromethyl-N-acetyl-N-(3-(6-hydroxy-3-amidinophenyl)prop-2-en-1-yl)benzenamine;
4-(N'-(methyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;
4-(N'-(1-iminoethyl)piperidin-4-yl)oxy-3-carboxy-N-((-methylethyl)carbonyl)-N-(3-(6-hydroxy-3-amidinophenyl)prop-2-en-1-yl)benzenamine;
4-(N'-(1-iminoethyl)piperdin-4-yl)oxy-3-carboxy-N-(2-(carboxy)ethylcarbonyl)-N-(3-(6-hydroxy-3-amidinophenyl)prop-2-en-1-yl)benzenamine;

4-(piperidin-4-yl)oxy-3-trifluoromethyl-N-(benzyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-((1-methylethyl)carbonyl)-N-(3-(6-hydroxy-3-amidinophenyl)prop-2-en-1-yl)benzenamine;

4-(N'-(1-iminoethyl)piperidin-4-yl)oxy-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(benzyl)-N-(3-(6-hydroxy-3-amidinophenyl)prop-2-en-1-yl)benzenamine;

4-(piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(piperidin-4-yl)oxy-3-trifluoromethyl-N-acetyl-N-(3-(6-hydroxy-3-amidinophenyl)prop-2-en-1-yl)benzenamine;

4(N'-(1-iminoethyl)piperidin-4-yl)oxy-3-trifluoromethyl-N-(2-(carboxy)ethylcarbonyl)-N-(3-(6-hydroxy-3-amidinophenyl)prop-2-en -1-yl)benzenamine;

4-(N'-(acetyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(methyl)piperidin-4-yl)oxy-3-trifluoromethyl-N-(2-(methoxycarbonyl)ethylcarbonyl)-N-(3-(6-hydroxy-3-amidinophenyl)prop-2-en-1-yl)benzenamine;

4-(N'-(methyl)piperidin-4-yl)oxy-3-trifluoromethyl-N-acetyl-N-(3-(6-hydroxy-3-amidinophenyl)prop-2-en-1-yl)benzenamine;

4-(N'-(1-iminoethyl)piperidin-4-yl)oxy-3-trifluoromethyl-N-(methoxycarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(benzyl)-N-(3-(6-hydroxy-3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(3-amidinophenyl)prop-2-en-1-yl)benzenamine;

4-(N'-(1-iminoethyl)piperidin-4-yl)oxy-3-carboxy-N-((1-methylethyl)carbonyl)-N-(3-(3-amidinophenyl)prop-2-en-1-yl)benzenamine;

4-(N'-(aminocarbonyl)piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-(methoxycarbonyl)-N-(2-(methoxycarbonyl)ethylcarbonyl)-N-(3-(6-hydroxy-3-amidinophenyl)prop-2-en-1-yl)benzenamine;

4-(N'-(1-iminoethyl)piperidin-4-yl)oxy-3-carboxy-N-(2-13 (aminocarbonyl)ethylcarbonyl)-N-(3-(6-hydroxy-3-amidinophenyl)prop-2-en-1-yl)benzenamine;

4-(N'-(methylsulfonyl)piperidin-4-yl)oxy-3-trifluoromethyl-N-(3-(6-hydroxy-3-amidinophenyl)prop-2-en-1-yl)benzenamine;

4-(N'-(methylsulfonyl)piperidin-4-yl)oxy-3-trifluoromethyl-N-((1-methylethyl)carbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(2-(ethoxycarbonyl)ethylcarbonyl)-N-(3-(3-amidinophenyl)prop-2-en-1-yl)benzenamine;

4-(N'-(methyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(acetyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(ethoxycarbonyl)piperidin-4-yl)oxy-3-trifluoromethyl-N-(3-(6-hydroxy-3-amidinophenyl)prop-2-en-1-yl)benzenamine;

4-(N'-(1-iminoethyl)piperidin-4-yl)oxy-3-(nitro)-N-(aminocarbonylmethyl)-N-(3-(3-amidinophenyl)prop-2-en-1-yl)benzenamine;

4-(N'-(ethoxycarbonylmethyl)piperidin-4-yl)oxy-3-trifluoromethyl-N-(2-(ethoxycarbonyl)ethylcarbonyl)-N-(3-(6-hydroxy-3-amidinophenyl)prop-2-en-1-yl)benzenamine;

4-(N'-(1-iminoethyl)piperidin-4-yl)oxy-3-trifluoromethyl-N-((1,2-di(ethoxycarbonyl)ethyl)aminocarbonyl)-N-(3-(3-amidinophenyl)prop-2-en-1-yl)benzenamine;

4-(N'-(1-iminoethyl)piperidin-4-yl)oxy-3-trifluoromethyl-N-((1,2-di(carboxy)ethyl)aminocarbonyl)-N-(3-(3-amidinophenyl)prop-2-en-1-yl)benzenamine;

4-(piperidin-4-yl)oxy-3-carboxy-N-(2-(carboxy)ethylcarbonyl)-N-(3-(3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(6-hydroxy-3-amidinophenyl)prop-2-en-1-yl)benzenamine;

4-(N'-(1-iminoethyl)piperidin-4-yl)oxy-3-carboxy-N-(2-(carboxy)ethylcarbonyl)-N-(3-(3-amidinophenyl)prop-2-en-1-yl)benzenamine;

4-(N'-(acetyl)piperidin-4-yl)oxy-3-trifluoromethyl-N-((1,2-di(ethoxycarbonyl)ethyl)aminocarbonyl)-N-(3-(3-amidinophenyl)prop-2-en-1-yl)benzenamine;

4-(N'-(acetyl)piperidin-4-yl)oxy-3-trifluoromethyl-N-((3,4-di(ethoxycarbonyl)phenyl)carbonyl)-N-(3-(3-amidinophenyl)prop-2-en-1-yl)benzenamine;

4-(N'-(carboxymethyl)piperidin-4-yl)oxy-3-trifluoromethyl-N-(2-(carboxy)ethylcarbonyl)-N-(3-(6-hydroxy-3-amidinophenyl)prop-2-en-1-yl)benzenamine;

4-(N'-(acetyl)piperidin-4-yl)oxy-3-trifluoromethyl-N-((1,2-di(carboxy)ethyl)aminocarbonyl)-N-(3-(3-amidinophenyl)prop-2-en-1-yl)benzenamine;

4-(N'-(1-iminoethyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(methyl)piperidin-4-yl)oxy-3-trifluoromethyl-N-((1,2-di(carboxy)ethyl)aminocarbonyl)-N-(3-(3-amidinophenyl)prop-2-en-1-yl)benzenamine;

4-(N'-(acetyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(1-iminoethyl)piperidin-4-yl)oxy-3-trifluoromethyl-N-((3,4-di(ethoxycarbonyl)phenyl)carbonyl)-N-(3-(3-amidinophenyl)prop-2-en-1-yl)benzenamine;

4-(N'-(methyl)piperidin-4-yl)oxy-3-trifluoromethyl-N-((3,4-dicarboxy)phenyl)carbonyl)-N-(3-(3-amidinophenyl)prop-2-en-1-yl)benzenamine;

4-(N'-(methyl)piperidin-4-yl)oxy-3-trifluoromethyl-N-((3,4-di(ethoxycarbonyl)phenyl)carbonyl)-N-(3-(3-amidinophenyl)prop-2-en-1-yl)benzenamine;

4-(N'-(carboxymethyl)piperidin-4-yl)oxy-3-trifluoromethyl-N-(2-(carboxy)ethylcarbonyl)-N-(3-(3-amidinophenyl)prop-2-en-1-yl)benzenamine;

4-(N'-(carboxymethyl)piperidin-4-yl)oxy-3-trifluoromethyl-N-((3,4-di(carboxy)phenyl)carbonyl)-N-(3-(3-amidinophenyl)prop-2-en-1-yl)benzenamine;

4-(N'-(carboxymethyl)piperidin-4-yl)oxy-3-trifluoromethyl-N-(3-(3-amidinophenyl)prop-2-en-1-yl)benzenamine;

4-(piperidin-4-yl)oxy-3-(ethoxycarbonyl)-N-(3-(3-amidinophenyl)prop-2-en-1-yl)-N-(3-(3-amidinophenyl)prop-2-en-1-yl)benzenamine; and 4-(piperidin-4-yl)oxy-3-trifluoromethyl-N-(3-(6-benzyloxy-3-amidinophenyl)prop-2-en-1-yl)-N-(3-(6-benzyloxy-3-amidinophenyl)prop2-en-1-yl)benzenamine.

8. The compound of claim 1 wherein
A is —O—;
W is —N($R^4$)—;
each m is independently 0, 1 or 2;
n is 1;
$R^2$ is —[C($R^7$)$_2$]$_m$—[C($R^8$)]═CH—;
$R^3$ is —C(NH)NH$_2$; and
$R^8$ is methyl.

9. The compound of claim 8 selected from the group consisting of the following:
4-(N'-(1-iminoethyl)piperidin-4-yl)oxy-3-(nitro)-N-(2-methyl-3-(3-amidinophenyl)prop-2-en-1-yl)benzenamine;
4-(piperidin-4-yl)oxy-N-(2-methyl-3-(6-hydroxy-3-amidinophenyl)prop-2-en-1-yl)benzenamine ;
4-(piperidin-4-yl)oxy-N-(2-methyl-3-(6-benzyloxy-3-amidinophenyl)prop-2-en-1-yl)benzenamine;
4-(N'-(1-iminoethyl)piperidin-4-yl)oxy-N-(2-methyl-3-(6-hydroxy-3-amidinophenyl)prop-2-en-1-yl)benzenamine;
4-(N'-(acetyl)piperidin-4-yl)oxy-N-(2-methyl-3-(6-hydroxy-3-amidinophenyl)prop-2-en-1-yl)benzenamine;
4-(N'-(1-iminoethyl)piperidin-4-yl)oxy-N-(2-methyl-3-(6-benzyloxy-3-amidinophenyl)prop-2-en-1-yl)benzenamine;
4-(piperidin-4-yl)oxy-3-carboxy-N-(2-(carboxy)ethylcarbonyl)-N-(2-methyl-3-(3-amidinophenyl)prop-2-en-1-yl)benzenamine;
4-(N'-(1-iminoethyl)piperidin-4-yl)oxy-3-carboxy-N-(2-(carboxy)ethylcarbonyl)-N-(2-methyl-3-(6-hydroxy-3-amidinophenyl)prop-2-en-1-yl)benzenamine;
4-(N'-(1-iminoethyl)piperidin-4-yl)oxy-3-carboxy-N-(2-(carboxy)ethylcarbonyl)-N-(2-methyl-3-(3-amidinophenyl)prop-2-en-1-yl)benzenamine; and
4-(N'-(carboxymethyl)piperidin-4-yl)oxy-3-trifluoromethyl-N-(2-(carboxy)ethylcarbonyl)-N-(2-methyl-3-(6-hydroxy-3-amidinophenyl)prop-2-en-1-yl)benzenamine.

10. The compound of claim 1 wherein
A is —O—;
W is —N($R^4$)—;
each m is independently 0, 1 or 2;
n is 1;
$R^2$ is —[C($R^7$)($R^8$)]—⟨phenyl⟩ ;

and $R^3$ is —C(NH)NH$_2$.

11. The compound of claim 1 wherein
A is —O—;
W is —O— or —S—;
each m is independently 0, 1 or 2;
n is 1;
$R^2$ is —[C($R^7$)$_2$]$_m$—[C($R^8$)]═CH—; and
$R^3$ is —C(NH)NH$_2$.

12. The compound of claim 11 selected from the group consisting of the following:
4-(N'-(1-iminoethyl)piperidin-4-yl)oxy-3-nitro-N-(3-(3-amidinophenyl)benzyl)benzenamine;
4-(N'-(acetyl)piperidin-4-yl)oxy-3-methoxy-N-(3-(3-amidinophenyl)benzyl)benzenamine;
4-(N-'-(1-iminoethyl)piperidin-4-yl)oxy-N-(3-(3-amidinophenyl)benzyl)benzenamine;
4-(piperidin-4-yl)oxy-3-(ethoxycarbonyl)-N-(3-(3-amidinophenyl)benzyl)benzenamine;
4-(N'-(1-iminoethyl)piperidin-4-yl)oxy-3-(ethoxycarbonyl)-N-(3-(3-amidinophenyl)benzyl)benzenamine;
4-(N'-(1-iminoethyl)piperidin-4-yl)oxy-3-carboxy-N-(3-(3-amidinophenyl)benzyl)benzenamine;
4-(piperidin-4-yl)oxy-3-(ethoxycarbonyl)-N-(ethoxycarbonylmethyl)-N-(3-(3-amidinophenyl)benzyl)benzenamine;
4-(N'-(1-iminoethyl)piperidin-4-yl)oxy-3-(ethoxycarbonyl)-N-(ethoxycarbonylmethyl)-N-(3-(3-amidinophenyl)benzyl)benzenamine;
4-(N'-(1-iminoethyl)piperidin-4-yl)oxy-3-carboxy-N-(carboxymethyl)-N-(3-(3-amidinophenyl)benzyl)benzenamine;
4-(N'-(1-iminoethyl)piperidin-4-yl)oxy-3-trifluoromethyl-N-(3-(3-amidinophenyl)benzyl)benzenamine;
4-(piperidin-4-yl)oxy-3-trifluoromethyl-N-(3-(3-amidinophenyl)benzyl)benzenamine;
4-(N'-(1-iminoethyl)piperidin-4-yl)oxy-3-trifluoromethyl-N-(ethoxycarbonylmethyl)-N-(3-(3-amidinophenyl)benzyl)benzenamine;
4-(N'-(1-iminoethyl)piperidin-4-yl)oxy-3-(ethoxycarbonyl)-N-(3-(3-amidinophenyl)benzyl)-N-(3-(3-amidinophenyl)benzyl)benzenamine; and
4-(N'-(1-iminoethyl)piperidin-4-yl)oxy-3-carboxy-N-(3-(3-amidinophenyl)benzyl)-N-(3-(3-amidinophenyl)benzyl)benzenamine.

13. The compound of claim 11 selected from the group consisting of the following:
4-(tetrahydropyran4-yl)oxy-3-trifluoromethyl-N-(3-(6-hydroxy-3-amidinophenyl)prop-2-en-1-yl)benzenamine; and
4-(thian-4-yl)oxy-3-trifluoromethyl-N-(3-(6-hydroxy-3-amidinophenyl)prop-2-en-1-yl)benzenamine.

14. A pharmaceutical composition useful in treating a human having a disease-state characterized by thrombotic activity, which composition comprises a therapeutically effective amount of a compound of formula (I):

(I)

[structure]

wherein:
A is —O— or —N($R^7$)—;
W is —N($R^4$)—, —S— or —O—;
each m is independently 0, 1, 2, 3 or 4;
n is 0 or 1;
$R^1$ is hydrogen, alkyl, alkylcarbonyl, phenylalylidenyl (wherein the phenyl group is optionally substituted by alkyl, halo, alkoxy, aralkoxy, —C(NH)—NH$_2$, —C(NH)N(H)O$R^7$, —C(NH)N(H)C(O)O$R^8$, —C(NH)N(H)C(O)$R^9$, —C(NH)N(H)S(O)$_2R^9$, or —C(NH)N(H)C(O)N(H)$R^7$), alkoxycarbonylalkyl, carboxyalkyl, aminocarbonylalkyl, monoalkylaminocarbonylalkyl, dialkylaminocarbonylalkyl, alkoxycarbonyl, phenylcarbonyl (wherein the phenyl group is optionally substituted by carboxy or alkoxycarbonyl), carboxyalkylcarbonyl, alkoxycarbonylalkylcarbonyl, aminocarbonylalkylcarbonyl, benzyl (wherein the phenyl group is optionally substituted by alkyl, halo, alkoxy, aralkoxy, —C(NH)—NH$_2$, —C(NH)N(H)OR$^7$, —C(NH)N(H)C(O)OR$^9$, —C(NH)N(H)C(O)R$^9$, —C(NH)N(H)S(O)$_2$R$^9$, or —C(NH)N(H)C(O)N(H)R$^7$), monoalkylaminocarbonyl, monoalkylaminocarbonyl, alkylsulfonyl, arylsulfonyl or dialkylaminosulfonyl;

R$^2$ is —[C(R$^7$)$_2$]$_m$—, —[C(R$^7$)$_2$]$_m$—C(O)—N(R$^8$)—, or —[C(R$^7$)$_2$]$_m$—[C(R$^8$)]=CH—;

or R$^2$ is

—[C(R$^7$)(R$^8$)]—⟨phenyl⟩ ;

R$^3$ is —C(NH)NH$_2$, —C(NH)N(H)OR$^7$, —C(NH)N(H)C(O)OR$^9$, —C(NH)N(H)C(O)R$^9$, C(NH)N(H)S(O)$_2$R$^9$, or —C(NH)N(H)C(O)N(H)R$^7$;

R$^4$ is hydrogen, alkyl, alkylcarbonyl, aminocarbonyl, monoalkylaminocarbonyl, dialkylaminocarbonyl, aminosulfonyl, alkoxycarbonyl, carboxyalkyl, alkoxycarbonylalkyl, or —C(NH)CH$_3$.

each R$^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl;

R$^6$ is hydrogen, alkyl, hydroxy, alkoxy, aralkoxy (wherein the aryl group is optionally substituted by alkyl, halo or alkoxy);

each R$^7$ and R$^8$ is independently hydrogen, alkyl, aryl, or aralkyl; and each R$^9$ is alkyl or aralkyl;

as a single stereoisomer or a mixture thereof; or a pharmaceutically acceptable salt thereof, and a pharmaceutically acceptable excipient.

15. A method of treating a human having a disease-state characterized by thrombotic activity, which method comprises administering to a human in need thereof a therapeutically effective amount of a compound of formula (I):

(I)

wherein:

A is —O— or —N(R$^7$)—;

W is —N(R$^4$)—, —S— or —O—;

each m is independently 0, 1, 2, 3 or 4;

n is 0 or 1;

R$^1$ is hydrogen, alkyl, alkylcarbonyl, phenylalylidenyl (wherein the phenyl group is optionally substituted by alkyl, halo, alkoxy, aralkoxy, —C(NH)—NH$_2$, —C(NH)N(H)OR$^7$, —C(NH)N(H)C(O)OR$^9$, —C(NH)N(H)C(O)R$^9$, —C(NH)N(H)S(O)$_2$R$^9$, or —C(NH)N(H)C(O)N(H)R$^7$), alkoxycarbonylalkyl, carboxyalkyl, aminocarbonylalkyl, monoalkylaminocarbonylalkyl, dialkylaminocarbonylalkyl, alkoxycarbonyl, phenylcarbonyl (wherein the phenyl group is optionally substituted by carboxy or alkoxycarbonyl), carboxyalkylcarbonyl, alkoxycarbonylalkylcarbonyl, aminocarbonylalkylcarbonyl, benzyl (wherein the phenyl group is optionally substituted by alkyl, halo, alkoxy, aralkoxy, —C(NH)—NH$_2$, —C(NH)N(H)OR$^7$, —C(NH)N(H)C(O)OR$^9$, —C(NH)N(H)C(O)R$^9$, —C(NH)N(H)S(O)$_2$R$^9$, or —C(NH)N(H)C(O)N(H)R$^7$), monoalkylaminocarbonyl, monoalkylaminocarbonyl, alkylsulfonyl, arylsulfonyl or dialkylaminosulfonyl;

R$^2$ is —[C(R$^7$)$_2$]$_m$—, —[C(R$^7$)$_2$]$_m$—C(O)—N(R$^8$)—, or —[C(R$^7$)$_2$]$_m$—[C(R$^8$)]=CH—;

or R$^2$ is

—[C(R$^7$)(R$^8$)]—⟨phenyl⟩ ;

R$^3$ is —C(NH)NH$_2$, —C(NH)N(H)OR$^7$, —C(NH)N(H)C(O)OR$^9$, —C(NH)N(H)C(O)R$^9$, —C(NH)N(H)S(O)$_2$R$^9$, —C(NH)N(H)C(O)N(H)R$^7$;

R$^4$ is hydrogen, alkyl, alkylcarbonyl, aminocarbonyl, monoalkylaminocarbonyl, dialkylaminocarbonyl, aminosulfonyl, alkoxycarbonyl, carboxyalkyl, alkoxycarbonylalkyl, or —C(NH)CH$_3$;

each R$^5$ is independently hydrogen, alkyl, halo, haloalkyl, nitro, hydroxy, alkoxy, carboxy, alkoxycarbonyl, amino, monoalkylamino, dialkylamino, aminocarbonyl, monoalkylaminocarbonyl, or dialkylaminocarbonyl;

R$^6$ is hydrogen, alkyl, hydroxy, alkoxy, aralkoxy (wherein the aryl group is optionally substituted by alkyl, halo or alkoxy);

each R$^7$ and R$^8$ is independently hydrogen, alkyl, aryl, or aralkyl; and each R$^9$ is alkyl or aralkyl;

as a single stereoisomer or a mixture thereof; or a pharmaceutically acceptable salt thereof.

* * * * *